US009951311B2

(12) United States Patent
Gu et al.

(10) Patent No.: US 9,951,311 B2
(45) Date of Patent: Apr. 24, 2018

(54) AGENTS AND METHODS TO ELICIT ANTI-TUMOR IMMUNE RESPONSE

(71) Applicants: THE TRUSTEES OF COLUMBIA UNIVERSITY IN THE CITY OF NEW YORK, New York, NY (US); The United States of America as represented by the Secretary of the Department of Health and Human Services, Washington, DC (US)

(72) Inventors: Hua Gu, New York, NY (US); Richard Hodes, Bethesda, MD (US); Jeffrey J. Chiang, Herndon, VA (US); Ihnkyung Jang, Jupiter, FL (US)

(73) Assignees: THE TRUSTEES OF COLUMBIA UNIVERSITY IN THE CITY OF NEW YORK, New York, NY (US); THE UNITED STATES OF AMERICA, AS REPRESENTED BY THE SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 34 days.

(21) Appl. No.: 15/089,016

(22) Filed: Apr. 1, 2016

(65) Prior Publication Data
US 2016/0312183 A1    Oct. 27, 2016

Related U.S. Application Data

(62) Division of application No. 12/441,335, filed as application No. PCT/US2007/019824 on Sep. 13, 2007, now Pat. No. 9,334,522.

(60) Provisional application No. 60/844,240, filed on Sep. 13, 2006.

(51) Int. Cl.
A61K 39/00    (2006.01)
A61K 48/00    (2006.01)
C12N 15/113   (2010.01)
C12N 5/0783   (2010.01)
C12Q 1/25     (2006.01)
G01N 33/50    (2006.01)

(52) U.S. Cl.
CPC ......... *C12N 5/0638* (2013.01); *C12N 5/0636* (2013.01); *C12N 15/113* (2013.01); *C12Q 1/25* (2013.01); *G01N 33/5011* (2013.01); *A61K 2039/5158* (2013.01); *A61K 2039/57* (2013.01); *C12N 2310/14* (2013.01); *C12N 2501/998* (2013.01); *G01N 2333/70514* (2013.01); *G01N 2333/70517* (2013.01); *G01N 2333/70539* (2013.01); *G01N 2333/9015* (2013.01); *G01N 2500/10* (2013.01)

(58) Field of Classification Search
USPC ............ 435/6.1, 91.1, 91.31, 455, 7.1, 375; 514/44, 1, 2; 536/23.1, 24.5; 424/277; 604/522
See application file for complete search history.

(56) References Cited

U.S. PATENT DOCUMENTS

| 8,809,288 B2 | 8/2014 | Baier et al. | |
|---|---|---|---|
| 2002/0051980 A1* | 5/2002 | Witte | C07K 14/705 435/6.16 |
| 2004/0115216 A1 | 6/2004 | Schneck et al. | |
| 2006/0292119 A1 | 12/2006 | Chen et al. | |
| 2007/0054355 A1 | 3/2007 | Reiss et al. | |
| 2007/0087988 A1 | 4/2007 | Sawasdikosol et al. | |
| 2007/0106065 A1 | 5/2007 | Kearney et al. | |
| 2010/0135910 A1 | 6/2010 | Rao et al. | |

FOREIGN PATENT DOCUMENTS

WO    WO-04/099388    11/2004

OTHER PUBLICATIONS

Krawczyk et al, Immunity, vol. 13, pp. 463-473 (2000).*
Allison JP, Hurwitz AA, Leach DR. 1995. Manipulation of costimulatory singlas to enhance antitumor T-cell responses. *Curr Opin Immunol* 7: 682-6.
Bachmaier K, Krawczyk C, Kozieradzki I, Kong YY, Sasaki T, Oliveira-dos-Santos A, Mariathasan S, Bouchard D, Wakeham A, Itie A, Le J, Ohashi PS, Sarosi I, Nishina H, Lipkowitz S, Penniger JM. 2000. Negative regulation of lumphocyte activation and auto-immunity by the molecular adaptor Cbl-b. *Nature* 403:211-6.
Barlow, C., S. Hirotsune, R. Paylor, M. Liyanage, M. Eckhaus, F. Collins, Y. Shiloh, J.N. Crawley, T. Ried, D. Tagle, and A. Wynshaw-Boris. 1996. Atm-deficient mice: a paradigm of ataxia telangiectasa. *Cell* 86:159-171.
Barton, G M, et al. Retroviral delivery of small interfering RNA into primary cells. Proc. Natl. Acad. Sci. USA 2002; 99:14943-14945.
Bertolino, et al., "Death by neglect as a deletional nechanism of peripheral tolerance," Int. Immunol., vol. 11, No. 8, pp. 1225-1237 (1999).

(Continued)

*Primary Examiner* — Jane Zara
(74) *Attorney, Agent, or Firm* — Wilmer Cutler Pickering Hale and Dorr LLP

(57) ABSTRACT

The invention provides an isolated, purified population of human cells comprising CD8+ T cells with reduced Cbl-b activity. The invention provides uses of such cells in methods for inducing or enhancing an anti-tumor immune response in a subject. These methods comprise: (a) providing a cell population, from a subject or from another source, which comprises CD8+ T cells, (b) reducing Cbl-b activity in the CD8+ T-cells, (c) administering the cells of step (b) to the subject. The invention provides methods for making CD8+ T cells that do not require stimulation through a co-receptor in order for the cell to become activated or proliferated in response to contact via its T cell receptor. Such methods are based upon reducing function of Cbl-b. The invention also provides methods for identifying agents which affect Cbl-b expression or activity.

11 Claims, 36 Drawing Sheets

(56) References Cited

OTHER PUBLICATIONS

Bertolino, P., et al., "Antigen-Specific Primary Activation of CD8+ T Cells Within the Liver," The Journal of Immunology, vol. 166, pp. 5430-5438 (2001).
Berzofsky JA, Ahlers JD, Belyakov IM. 2001. Strategies for designing and optimizing new generation vaccines. Natl Rev Immunol 1:209-19.
Boon T, Certottini JC, Van den Eynde B, van der Bruggen P, Van Pel A. 1994. Tumor antigens recognized by T lymphocytes. Annu Rev Immunol 12:337-65.
Boon T, van der Bruggen P. 1996. Human tumor antigens recognized by T lymphocytes. J Exp Med 183:725-9.
Brummelkamp TR, Bernards R, Agami R. 2002. A system for stable expression of short interfering RNAs in mammalian cells. Science 296:550-3.
Ceredig R, Allan JE, Tabi Z, Lynch F, Doherty PC. 1987. Phenotypic analysis of the inflammatory exudate in murine lymphocytic choriomeningitis. J Exp Med 165:1539-51.
Chambers CA, Kuhns MS, Egen JG, Allison JP. 2001. CTLA-4 mediated inhibition in regulation of T cell responses: mechanisms and manipulation in tumor immunotherapy. Annu Rev Immunol 19:565-94.
Chen L, Ashe S, Brady WA, Hellstrom I, Hellstrom KE, Ledbetter JA, McGowan P, Linsley PS. 1992. Costimulation of antitumor immunity by the B7 counterreceptor for the T lymphocyte molecules CD28 and CTLA-4. Cell 71:1093-102.
Chen L, McGowan P, Ashe S, Johnston J, Li Y, Hellstrom I, Hellstrom KE. Tumor immunogenicity determines the effect of B7 costimulation on T cell-mediated tumor immunity. J Exp Med 179:523-32.
Chiang et al., "Ablation of Cbl-b provides protection against transplanted and spontaneous tumors," The Journal of Clinical Investigation, vol. 117, pp. 1029-1036 (Apr. 2007).
Chiang YJ, Kole HK, Brown K, Naramura M, Fukuhara S, Hu RJ, Jang IK, Gutkind JS, Shevach E, Gu H. 2000. Cbl-b regulates the CD28 dependence of T-cell activation. Nature 403:216-20.
Dudley ME, Rosenberg SA. 2003. Adoptive-cell-transfer therapy for the treatment of patients with cancer. Nat Rev Cancer 3:666-75.
Dudley ME, Wunderlich JR, Robbins PF, Yang JC, Hwu P, Schwartzentruber DJ, Topalian SL, Sherry R, Restifo NP, Hubicki AM, Robinson MR, Raffeld M, Duray P, Seipp CA, Rogers-Freezer L, Morton KE, Mavroukakis SA, White DE, Rosenberg SA. 2002. Cancer regression and autoimmunity in patients after clonal repopulation with antitumor lymphocytes. Science 298:850-4.
Elbashir et al., "Duplexes of 21-nucleotide RNAs mediate RNA interference in cultured mammalian cells," 2001, Nature 411:494-498.
European Search Report Issued by the European Patent Office for Application No. 07838099.5 dated May 28, 2014 (4 pgs.).
Extended European Search Report dated Apr. 12, 2010, for European Patent Application No. 07838099.5.
Fang D, Liu YC. 2001. Proteolysis-independent regulation of P13K by Cbl-b-mediated ubiquitination in T cells. Nat Immunol 2:870-5.
Finkelstein SE, Heimann DM, Klebanoff CA, Antony PA, Gattinoni L, Hinrichs CS, Hwang LN, Palmer DC, Spiess PJ, Surman DR, Wrzesiniski C, Yu Z, Rosenberg SA, Restifo NP. 2004. Bedside to bench and back again: how animal models are guiding the development of new immunotherapies for cancer. J Leukoc Biol 76:333-7.
Freemont PS. 2000. RING for destruction? Curr Biol 10:R84-7.
Gorer, P.A. 1950. Studies in antibody response of mice to tumor inoculation. Br J Cancer 4:372-379.
Greenberg PD. 1991. Adoptive T cell therapy of tumors: mechanisms operative in the recognition and elimination of tumor cells. Adv Immunol 49:281-355.
Groh V, Wu J, Yee C, Spies T. 2002. Tumour-derived soluble MIC ligands impair expression of NKG2D and T-cell activation. Nature 419:734-8.

Hanson HL, Donermeyer DL, Ikeda H, White JM, Shankaran V, Old LJ, Shiku H, Schreiber RD, Allen PM. 2000. Eradication of established tumors by CD8+ T cell adoptive immunotherapy. Immunity 13:265-76.
Helmich, B.K., and R.W. Dutton. 2001. The role of adoptively transferred CD8 T cells and host cells in the control of the growth of the EG7 thymoma: factors that determine the relative effectiveness and homing properties of Tc1 and Tc2 effectors. J Immunol 166:6500-6508.
Hinrichs, et al., "Programming CD8+ T cells for effective immunotherapy," Curr. Opin. Immunol., vol. 18, No. 3, pp. 363-370, 12 pages (2006).
Hogquist KA, Jameson SC, Heath WR, Howard JL, Bevan MJ, Carbone FR. 1994. T cell receptor antagonist peptides induce positive selection. Cell 76:17-27.
Houghton AN, Gold JS, Blachere NE. 2001. Immunity against cancer: lessons learned from melanoma. Curr Opin Immunol 13:134-40.
International Search Report and Written Opinion dated Jun. 3, 2008 for International Application No. PCT/US07/19824 filed Sep. 13, 2007.
Jacque et al., "Modulation of HIV-1 replication by RNA interference," 2002, Nature 418:435-438.
Janeway C. 1989. Immunogenicity signals 1,2,3 . . . and 0. Immunol Today 10:283-6.
Janeway, Jr., C. A. and Bottomly, K., "Signals and Signs for Lymphocyte Responses," Cell, vol. 76, pp. 275-285 (Jan. 28, 1994).
Jeon, M.S., A. Atfield, K. Venuprasad, C. Krawczyk, R. Sarao, C. Elly, C. Yang, S. Arya, K. Bachmaier, L. Su, D. Bouchard, R. Jones, M. Gronski, P. Ohashi, T. Wada, D. Bloom, C.G. Fathman, Y.C. Liu, and J.M. Penninger. 2004. Essential role of the E3 ubiquitin ligase Cbl-b in T cell anergy induction. Immunity 21:167-177.
Joazeiro CA, Wing SS, Huang H, Leverson JD, Hunter T, Liu YC. 1999. The tyrosine kinase negative regulator c-Cbl as a RING-type, E2-dependent ubiquitin-protein ligase. Science 286:309-12.
Keane MM, Ettenberg SA, Nau MM, Banerjee P, Cuello M, Penninger J, Lipkowitz S. 1999. cbl-3: a new mammalian cbl family protein. Oncogene 18:3365-75.
Keane MM, Rivero-Lezcano OM, Mitchell JA, Robbins KC, Lipkowitz S. 1995. Cloning and characterization of cbl-b: a SH3 binding protein with homology to the c-cbl proto-oncogene. Oncogene 10:2367-77.
Kedl RM, Rees WA, Hildeman DA, Schaefer B, Mitchell T, Kappler J, Marrack P. 2000. T cells compete for access to antigen-bearing antigen-presenting cells. J Exp Med 192:1105-13.
Kelly JM, Sterry SJ, Cose S, Turner SJ, Fecondo J, Rodda S, Fink PJ, Carbone FR. 1993. Identification of conserved T cell receptor CDR3 residues contacting known exposed peptide side chains from a major histocompatibility complex class I-bound determinant. Eur J Immunol 23:3318-26.
Kronenberg, M., and A. Rudensky. 2005. Regulation of immunity by self-reactive T cells. Nature 435:598-604.
Lafferty KJ, Prowse SJ, Simeonovic CJ, Warren HS. 1983. Immunobiology of tissue transplantation: a return to the passenger leukocyte concept. Annu Rev Immunol 1:143-73.
Ledbetter JA, Rouse RV, Micklem HS, Herzenberg LA. 1980. T cell subsets defined by expression of Lyt-1,2,3 and Thy-1 antigens. Two-parameter immunofluorescence and cytotoxicity analysis with monoclonal antibodies modifies current views. J Exp Med 152:280-95.
Ledbetter, J. A., "CD28 ligation in T-cell activation: evidence for two signal transduction pathways," blood, vol. 75, pp. 1531-1539 (1990).
Lee et al., "Expression of small interfering RNAs targeted against HIV-1 rev transcripts in human cells," 2002, Nat Biotechnol 20:500-505.
Lee PP, Yee C, Savage PA, Fong L, Brockstedt D, Weber JS, Johnson D, Swetter S, Thompson J, Greenberg PD, Roederer M, Davis MM. 1999. Characterization of circulating T cells specific for tumor-associated antigens in melanoma patients. Nat Med 5:677-85.
Levkowitz G, Waterman H, Ettenberg SA, Katz M, Tsygankov AY, Alroy I, Lavi S, Iwai K, Reiss Y, Ciechanover A, Lipkowitz S,

(56) References Cited

OTHER PUBLICATIONS

Yarden Y. 1999. Ubiquitin ligase activity and tyrosine phosphorylation underlie suppression of growth factor signaling by c-Cbl/Sli-1. *Mol Cell* 4:1029-40.
Lewis, D L, et al. Efficient delivery of siRNA for inhibition of gene expression in postnatal mice. Nat. Genet. 2002; 32:107-108.
Liebowitz, et al., "Costimulatory approaches to adoptive immunotherapy," Curr. Opin. Oncol., vol. 10, No. 6, pp. 533-541 (1998).
Linsley PS, Brady W, Grosmaire L, Aruffo A, Damle NK, Ledbetter JA. 1991. Binding of the B cell activation antigen B7 to CD28 costimulates T cell proliferation and interleukin 2 mRNA accumulation. *J Exp Med* 173:721-30.
Liu X, Bai XF, Wen J, Gao JX, Liu J, Lu P, Wang Y, Zheng P, Liu Y. 2001. B7H costimulates clonal expansion of, and cognate destruction of tumor cells by, CD8(+) T lymphocytes in vivo. *J Exp Med* 194:1339-48.
Liu YC, Gu H. 2002. Cbl and Cbl-b in T-cell regulation. *Trends Immunol* 23:140-3.
Loeser and al., "Sponstaneous tumor rejection by cbl-b-deficient CD8+ T cells," JEM, vol. 204, pp. 879-891 (Apr. 2007).
Lupher ML, Jr., Andoniou CE, Bonita D, Miyake S, Band H. 1998. The c-Cbl oncoprotein. *Int J Biochem Cell Biol* 30:439-44.
McManus et al., "Gene silencing in mammalas by small interfering RNAs," 2002, Nat Rev Genet 3:737-747.
McManus et al., "Small interfering RNA-Mediated gene silencing in T Lymphocytes," J. Immunol. 169:5754-5760 (2000).
Melief CJ. 1992. Tumor eradication by adoptive transfer of cytotoxic T lymphocytes. *Adv Cancer Res* 58:143-75.
Miura-Shimura Y, Duan L, Rao NL, Reddi AL, Shimura H, Rottapel R, Druker BJ, Tsygankov A, Band V, Band H. 2003. Cbl-mediated ubiquitinylation and negative regulation of Vav. *J Biol Chem* 278:38495-504.
Miyagishi et al., "U6 promoter-driven siRNAs with four uridine 3' overhangs efficiently suppress targeted gene expression in mammalian cells," 2002, Nat Biotechnol. 20:497-500.
Moore, M.W., F.R. Carbone, and M.J. Bevan. 1988. Introduction of soluble protein into the class I pathway of antigen processing and presentation. *Cell* 54:777-785.
Morisaki T, Matsumoto K, Onishi H, Kuroki H, Baba E, Tasaki A, Kubo M, Nakamura M, Inaba S, Yamaguchi K, Tanaka M, Katano M. 2003. Dendritic cell-based combined immunotherapy with autologous tumor-pulsed dendritic cell vaccine and activated T cells for cancer patients: rationale, current progress, and perspectives. *Hum Cell* 16:175-82.
Mueller DL, Jenkins MK, Schwartz RH. 1989. Clonal expansion versus functional clonal inactivation: a costimulatory signalling pathway determines the outcome of T cell antigen receptor occupancy. *Annu Rev Immunol* 7:445-80.
Murphy MA, Schnall RG, Venter DJ, Barnett L, Bertoncello I, Thien CB, Langdon WY, Bowtell DD. 1998. Tissue hyperplasia and enhanced T-cell signalling via ZAP-70 in c-Cbl-deficient mice. *Mol Cell Biol* 18:4872-82.
Naramura M, Hu RJ, Gu H. 1998. Mice with a fluorescent marker for interleukin 2 gene activation. *Immunity* 9:209-16.
Naramura M, Jang IK, Kole H, Huang F, Haines D, Gu H. 2002. c-Cbl and Cbl-b regulate T cell responsiveness by promoting ligand-induced TCR down-modulation. *Nat Immunol* 3:1192-9.
Naramura M, Kole HK, Hu RJ, Gu H. 1998. Altered thymic positive selection and intracellular signals in Cbl-deficient mice. *Proc Natl Acad Sci U S A* 95:15547-52.
Nestle FO, Alijagic S, Gilliet M, Sun Y, Grabbe S, Dummer R, Burg G, Schadendorf D. 1998. Vaccination of melanoma patients with peptide—or tumor lysate-pulsed dendritic cells. *Nat Med* 4:328-32.
Novina et al., "siRNA-directed inhibition of HIV-1 infection," 2002, Nat Med 8:681-686.
Ochsenbein AF, Klenerman P, Karrer U, Ludewig B, Pericin M, Hengartner H, Zinkernagel RM. 1999. Immune surveillance against a solid tumor fails because of immunological ignorance. *Proc Natl Acad Sci U S A* 96:2233-8.
Overwijk WW, Theoret MR, Finkelstein SE, Surman DR, de Jong LA, Vyth-Dreese FA, Dellemijn TA, Antony PA, Spiess PJ, Palmer DC, Heimann DM, Klebanoff CA, Yu Z, Hwang LN, Feigenbaum L, Kruisbeek AM, Rosenberg SA, Restifo NP. 2003. Tumor regression and autoimmunity after reversal of a functionally tolerant state of self-reactive CD8+ T cells. *J Exp Med* 198:569-80.
Paddison et al., "Short hairpin RNAs (shRNAs) induce sequence-specific silencing in mammalian cells," 2002, Genes Dev. 16:948-958.
Pardoll DM. 1998. Cancer vaccines. *Nat Med* 4:525-31.
Paul, C P, et al. Effective expression of small interfering RNA in human cells. Nat. Biotechnol. 2002; 20:505-508.
Perdrizet GA, Ross SR, Stauss HJ, Singh S, Koeppen H, Schreiber H. 1990. Animals bearing malignant grafts reject normal grafts that express through gene transfer the same antigen. *J Exp Med* 171:1205-20.
Ramarathinam L, Castle M, Wu Y, Liu Y. 1994. T cell costimulation by B7/BB1 induces CD8 T cell-dependent tumor rejection: an important role of B7/BB1 in the induction, recruitment, and effector function of antitumor T cells. *J Exp Med* 179:1205-14.
Randall et al., "Clearance of replicating hepatitis C virus replicon RNAs in cell culture by small interfering RNA," 2003, Proc Natl Acad Sci USA 100:235-240.
Rangachari m., " Negative regulation of T cell receptor signals," Curr. Opin. Pharmacol., 4(4):415-422 (Aug. 2004).
Rao N, Dodge I, Band H. 2002. The Cbl family of ubiquitin ligases: critical negative regulators of tyrosine kinase signaling in the immune system. *J Leukoc Biol* 71:753-63.
Regnier DC, Kozak CA, Kingsley DM, Jenkins NA, Copeland NG, Langdon WY, Morse HC, 3rd. 1989. Identification of two murine loci homologous to the v-cbl oncogene. *J Virol* 63:3678-82.
Restifo NP, Esquivel F, Asher AL, Stotter H, Barth RJ, Bennink JR, Mule JJ, Yewdell JW, Rosenberg SA. 1991. Defective presentation of endogenous antigens by a murine sarcoma. Implications for the failure of an anti-tumor immune response. *J Immunol* 147:1453-9.
Roes J, Rajewsky K. 1991. Cell autonomous expression of IgD is not essential for the maturation of conventional B cells. *Int Immunol* 3:1367-71.
Rosenberg SA, Yang JC, Restifo NP. 2004. Cancer immunotherapy: moving beyond current vaccines. *Nat Med* 10:909-15.
Rosenberg SA. 2001. Progress in human tumour immunology and immunotherapy. *Nature* 411:380-4.
Rosenberg, S.A. 1999. A new era of cancer immunotherapy: converting theory to performance. *CA Cancer J Clin* 49:70-73, 65.
Rubinson DA, Dillon CP, Kwiatkowski AV, Sievers C, Yang L, Kopinja J, Rooney DL, Ihrig MM, McManus MT, Gertler FB, Scott ML, Van Parijs L. 2003. A lentivirus-based system to functionally silence genes in primary mammalian cells, stem cells and transgenic mice by RNA interference. *Nat Genet* 33:401-6.
Sarma S, Guo Y, Guilloux Y, Lee C, Bai XF, Liu Y. 1999. Cytotoxic T lymphocytes to an unmutated tumor rejection antigen P1A: normal development but restrained effector function in vivo. *J Exp Med* 189:811-20.
Schuler G, Schuler-Thurner B, Steinman RM. 2003. The use of dendritic cells in cancer immunotherapy. *Curr Opin Immunol* 15:138-47.
Schwartz RH. 1992. Costimulation of T lymphocytes: the role of CD28, CTLA-4, and B7/BB1 in interleukin-2 production and immunotherapy. *Cell* 71:1065-8.
Schwartz, Ronald H., "Models of T Cell Anergy: Is There a Common Molecular Mechanism?," The Journal of Experimental Medicines, vol. 184, pp. 1-8 (Jul. 1996).
Singer O, Yanai A, Verma IM. 2004. Silence of the genes. *Proc Nati Acad Sci U S A* 101:5313-4.
Singh S, Ross SR, Acena M, Rowley DA, Schreiber H. 1992. Stroma is critical for preventing or permitting immunological destruction of antigenic cancer cells. *J Exp Med* 175:139-46.
Somasundaram, R., L. Jacob, R. Swoboda, L. Caputo, H. Song, S. Basak, D. Monos, D. Peritt, F. Marincola, D. Cai, B. Birebent, E. Bloome, J. Kim, K. Berencsi, M. Mastrangelo, and D. Herlyn. 2002. Inhibition of cytolytic T lymphocyte proliferation by autologous

(56) References Cited

OTHER PUBLICATIONS

CD4+/CD25+ regulatory T cells in a colorectal carcinoma patient is mediated by transforming growth factor-beta. *Cancer Res* 62:5267-5272.

Song, E, et al. RNA interference targeting Fas protects mice from fulminant hepatitis. Nat. Med. 2003; 9:347-351.

Sorensen, D R, et al. Gene silencing by systemic delivery of synthetic siRNAs in adult mice. J Mol Biol. 2003; 327:761-766.

Speiser DE, Miranda R, Zakarian A, Bachmann MF, McKall-Faienza K, Odermatt B, Hanahan D, Zinkernagel RM, Ohashi PS. 1997. Self antigens expressed by solid tumors Do not efficiently stimulate naive or activated T cells: implications for immunotherapy. *J Exp Med* 186:645-53.

Steinman RM. 2001. Dendritic cells and the control of immunity: enhancing the efficiency of antigen presentation. *Mt Sinai J Med* 68:106-66.

Stewart, D. J. et al., "A phase II study of 5-fluorouracil plus folinic acid in malignant gliomas in adults," J. Neurooncol., vol. 23, No. 3, pp. 249-252 (1995).

Sui et al., "A DNA vector-based RNAi technology to suppress gene expression in mammalian cells," 2002, PNAS 99(6):5515-5520.

Terabe M, Matsui S, Noben-Trauth N, Chen H, Watson C, Donaldson DD, Carbone DP, Paul WE, Berzofsky JA. 2000. NKT cell-mediated repression of tumor immunosurveillance by IL-13 and the IL-4R-STAT6 pathway. *Nat Immunol* 1:515-20.

Thien CB, Langdon WY. 2001. Cbl: many adaptations to regulate protein tyrosine kinases. *Nat Rev Mol Cell Biol* 2:294-307.

Townsend SE, Allison JP. 1993. Tumor rejection after direct costimulation of CD8+ T cells by B7—transfected melanoma cells. *Science* 259:368-70.

Tsygankov AY, Teckchandani AM, Feshchenko EA, Swaminathan G. 2001. Beyond the RING: CBL proteins as multivalent adapters. *Oncogene* 20:6382-402.

Umlauf SW, Beverly B, Lantz O, Schwartz RH. 1995. Regulation of interleukin 2 gene expression by CD28 costimulation in mouse T-cell clones: both nuclear and cytoplasmic RNAs are regulated with complex kinetics. *Mol Cell Biol* 15:3197-205.

Vesosky and Hurwitz, "Modulation of costimulation to enhance tumor innunity," Cancer Immunol. Immunother., vol. 52, pp. 663-669 (2003).

Wallin JJ, Liang L, Bakardjiev A, Sha WC. 2001. Enhancement of CD8+ T cell responses by ICOS/B7h costimulation. *J Immunol* 167:132-9.

Wang, B., et al., "Multiple Paths for Activation of Naive CD8+ T Cells: CD4-Independent Help," The Journal of Immunology, vol. 167, pp. 1283-189 (2001).

Ward and Kaufman, "Targeting Costimulatory Pathways for Tumor Immunotherapy," Int. Rev. Immunol., vol. 26, No. 3-4, pp. 161-196 (2007).

Weaver CT, Unanue ER. 1990. The costimulatory function of antigen-presenting cells. *Immunol Today* 11:49-55.

Wianny & Zernicka-Goetz, "Specific interference with gene function by double-stranded RNA in early mouse development," 2000, Nature Cell Biology 2:70-75.

Wick M, Dubey P, Koeppen H, Siegel CT, Fields PE, Chen L, Bluestone JA, Schreiber H. 1997. Antigenic cancer cells grow progressively in immune hosts without evidence for T cell exhaustion or systemic anergy. *J Exp Med* 186:229-38.

Wilson et al., 2003, "RNA interference blocks gene expression and RNA synthesis from hepatitis C replicons propagated in human liver cells," Proc Natl Acad Sci USA 100:2783-2788.

Wohlfert, et al., "Cutting Edge: Deficiency in the E3 Ubiquitin Ligase Cbl-b Results in a Multifunctional Defect in T Cell TGF-β Sensitivity In Vitro and In Vivo," J. Immunol., vol. 176, No. 3, pp. 1316-1320 (2006).

Xia, H, et al. siRNA-mediated gene silencing in vitro and in vivo. Nat. Biotechnol. 2002; 20:1006-1010.

Yu P, Lee Y, Liu W, Chin RK, Wang J, Wang Y, Schietinger A, Philip M, Schreiber H, Fu YX. 2004. Priming of naive T cells inside tumors leads to eradication of established tumors. *Nat Immunol* 5:141-9.

Yu P, Spiotto MT, Lee Y, Schreiber H, Fu YX. 2003. Complementary role of CD4+ T cells and secondary lymphoid tissues for cross-presentation of tumor antigen to CD8+ T cells. *J Exp Med* 197:985-95.

Yu, X., R. Abe, and R.J. Hodes. 1998. The role of B7-CD28 co-stimulation in tumor rejection. *Int Immunol* 10:791-797.

Zhang et al, "A direct interaction between the adaptor protein Cbl-b and the kinase Zap-70 inducs a positive signal in T cells," Current Biology, vol. 9, pp. 203-206 (1999).

Zhang et al. "Negative Regulation of T cell Antigen Receptor-mediated Crk-L-C3G signaling and cell Adhesion by Cbl-b," The journal of Bioloical Chemistry, vol. 278, pp. 23978-23983 (2003).

Zheng N, Wang P, Jeffrey PD, Pavletich NP. 2000. Structure of a c-Cbl-UbcH7 complex: RING domain function in ubiquitin-protein ligases. *Cell* 102:533-9.

Zou YR, Sunshine MJ, Taniuchi I, Hatam F, Killeen N, Littman DR. 2001. Epigenetic silencing of CD4 in T cells committed to the cytotoxic lineage. *Nat Genet* 29:332-6.

Viola et al., "T Lymphocyte Costimulation Mediated by Reorganization of Membrane Microdomains," Science, 283, pp. 680-682 (1999).

\* cited by examiner

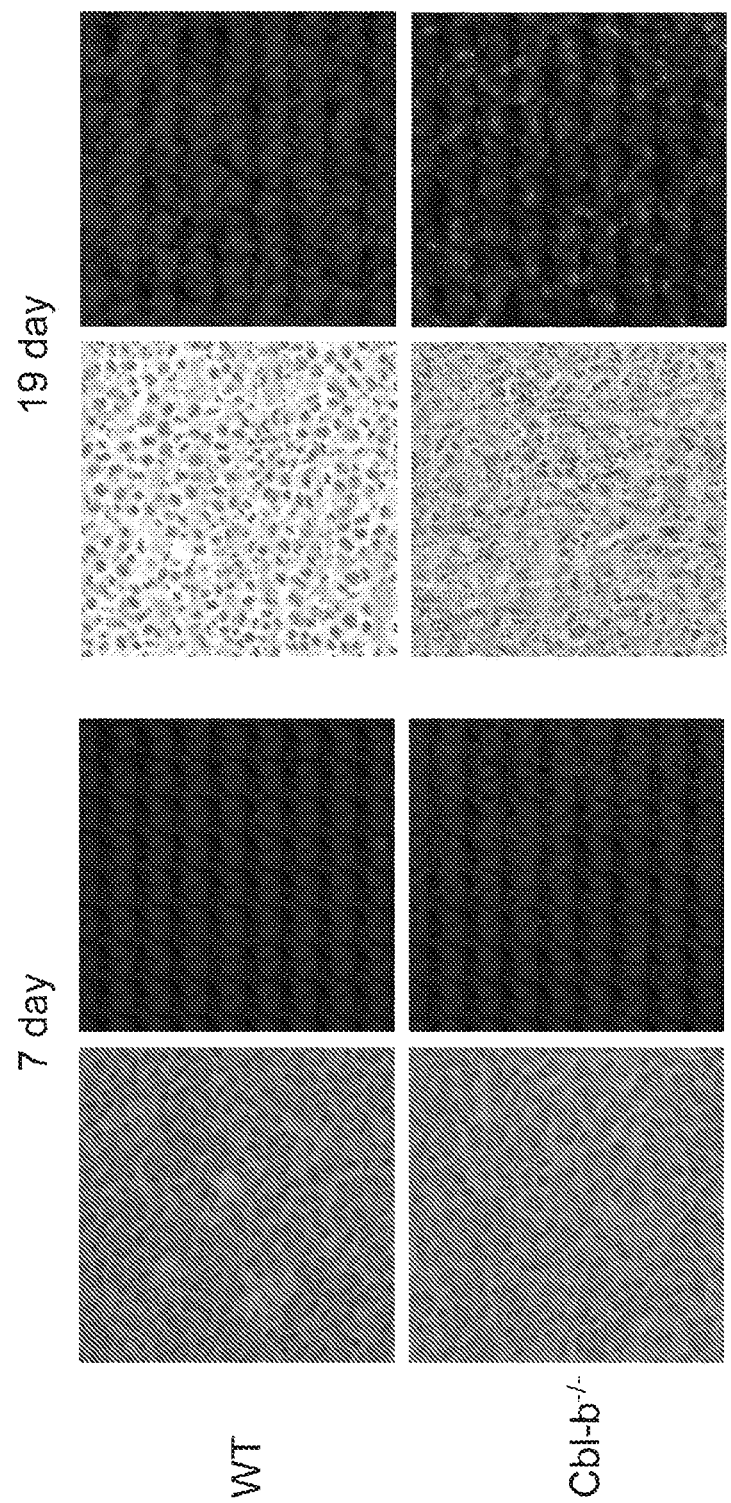

a b

SEQUENCE LISTING

```
<160> NUMBER OF SEQ ID NOS: 2

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
caggagtatg agacagaag                                                   19

<210> SEQ ID NO 2
<211> LENGTH: 8
<212> TYPE: PRT
<213> ORGANISM: Gallus gallus

<400> SEQUENCE: 2

Ser Ile Ile Asn Phe Glu Lys Leu
1               5
```

AGENTS AND METHODS TO ELICIT ANTI-TUMOR IMMUNE RESPONSE

This application is a divisional application of U.S. patent application Ser. No. 12/441,335, filed Jul. 29, 2011, which is a U.S. National Phase Application under 35 U.S.C. 371 of International Patent Application No. PCT/US2007/019824, filed Sep. 13, 2007, which claims the benefit of priority of U.S. Application Ser. No. 60/844,240, filed Sep. 13, 2016, each of which is incorporated by reference herewith in its entirety.

This invention was made with government support by NIH intramural research program. As such the United States Government has certain rights.

The text of all patent applications, published patent applications, issued and granted patents, and all references cited in this application are hereby incorporated by reference.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

All patents, patent applications and publications cited herein are hereby incorporated by reference in their entirety. The disclosures of these publications in their entireties are hereby incorporated by reference into this application in order to more fully describe the state of the art as known to those skilled therein as of the date of the invention described and claimed herein.

SEQUENCE LISTING

The instant application contains a Sequence Listing which has been submitted electronically in ASCII format and is hereby incorporated by reference in its entirety. Said ASCII copy, created on May 10, 2016, is named 19240.639US3_SL.txt and is 898 bytes in size.

BACKGROUND

Many clinical and experimental tumors express tumor antigens that can be recognized by CTL infiltrates. Numerous lines of evidence indicate that tumor-infiltrating CTLs can be activated and expanded by appropriate vaccination. However, despite T-cell recognition, most antigenic tumors are not rejected in the host. The mechanisms that disable CTL-mediated tumor rejection include low immunogenicity of the tumors such as MHC down-regulation and weak TCR-MHC-peptide interaction, active suppression of T-cell responsiveness by tumor itself, including tumor-derived transforming growth factor-beta (TGF-beta) and soluble MHC class-I-related molecules (MIC), prevention of T cell infiltration by tumor barrier composed of infiltrating stroma, as well as immunoregulatory mechanisms of the host immune system, such as suppression by CTLA-4, $CD4^+$ $CD25^+$ regulatory T cells, and IL13 produced by $CD4^+$ NK T cells. In addition, ample evidence also indicates that lack of appropriate recognition of tumor cells by tumor-specific CTLs in both priming and effector phases can contribute to the silence of an anti-tumor immune response.

Signals for Productive T-Cell Responses: The Two Signal Theory

Two signals are required for T cells to respond to antigens presented by antigen-presenting cells (APCs) or target cells such as tumor cells. Engagement of the T-cell antigen receptor (TCR) with antigen (peptide-MHC complexes) provides the initial signal. The second signal, termed costimulation, is initiated by interaction between co-receptors such as CD28 on T cells and the corresponding ligands such as B7s expressed by APCs. While stimulation of T cells by the professional APCs bearing both antigen and costimulatory ligands leads to T-cell proliferation and cytokine production, engagement of the TCR with antigens in the absence of costimulation results in T-cell unresponsiveness, a state termed anergy. One major obstacle in tumor immune surveillance is that most tumor cells do not express costimulatory ligands, such as B7s. Therefore, T cells that recognize these tumor cells usually cannot be fully activated and develop into effector cells, resulting in the failure of host immune surveillance against these tumors.

Modulation of TCR and Costimulatory Signals May Reverse the Silent State of Tumor-Specific Cytotoxic-T Cells Immune responses against immunogenic tumors are primarily mediated by T cells including $CD8^+$ CTLs and $CD4^+$ helper T cells. The tumor mass often has large numbers of CTL infiltrates. However, these CTLs are mostly non-responsive to tumors, as they are unable to exert the cytotoxicity to tumor burdens. Experiments have shown that in vitro priming of these infiltrates through TCR in the presence of exogenous IL-2 could activate these cells to proliferate and develop into CTL effectors. However, when these CTLs are adoptively transferred into tumor-bearing animals, they often fail to eradicate the established tumors, unless an appropriate vaccine, which alters the avidity between the TCR and MHC-peptide complex, as well as a large quantity of interleukin-2 (IL-2) are administrated simultaneously, indicating that the enhanced TCR signaling is essential to overcome the non responsiveness of tumor specific CTLs. Additionally, it has been shown that enforced expression of B7 on tumor cells can induce strong CTL responses, which eventually results in eradication of the inoculated tumors. An effective tumor rejection has also been achieved when other costimulatory signaling pathways, such as ICOS (inducible costimulatory molecule), are activated by the corresponding-ligand B7HH/B7RP-expressing tumor cells. Thus, modulation of TCR and costimulatory signals can be a potentially powerful therapeutic approach against cancer.

Although enforced expression of costimulatory ligands in tumor cells may induce strong CTL response against the antigen-expressing tumors, application of this approach in clinic therapy is hampered by the lack of efficient tool to deliver the costimulatory molecules specifically into tumor cells in vivo. An alternative approach to induce tumor-specific CTL responses is to use professional APCs such as dendritic cells to present tumor antigens. However, one limitation of this approach is that tumors of weak immunogenicity, which are less susceptible to the effector function of CTLs, may need costimulatory signals to augment CTL function. In addition, since professional APCs may present self-antigens to a broad spectrum of T cells, adoptive transfer of tumor antigen-loaded professional APCs might result in development of systemic autoimmune diseases. Tumor immunotherapy is a promising approach that in a number of experimental animal models, as well as in some clinical trials, leads to the regression of established primary and metastatic cancer. However, currently available approaches remain less successful than desired. A major obstacle that has yet to be overcome derives from the observation that generation of effective CTL responses against antigenic tumors requires costimulatory signals, and that many tumors do not express the necessary costimulatory ligands. As a result, T cells recognizing these tumors are often non-responsive in vivo.

Immune responses against immunogenic tumors are mediated by CD8$^+$-cytotoxic T lymphocytes (CTLs). Despite T cell recognition, most tumors are not rejected in the host. The mechanisms that may prevent CTL-mediated tumor rejection include inhibition of T-cell responsiveness by tumor-derived factors, such as transforming growth factor-β (TGF-β) and soluble MHC class-I-related molecules secreted by tumor cells, as well as negative regulation of the host immune system, including suppressive CTLA-4 signaling, the effect of CD25$^+$ regulatory T cells, and suppression by IL-13 produced by CD4$^+$ NK T cells. In addition to these mechanisms of active suppression, lack of effective recognition of tumors by T cells may disable an anti-tumor immune response, for example in the absence of TCR and/or costimulatory signals. Thus there remains a need for identifying agents and methods that allow and/or enhance anti-tumor immune responses in the absence of co-stimulatory signals.

SUMMARY OF THE INVENTION

In certain aspects, the invention provides methods for making a CD8$^+$ T cell that does not require stimulation through a co-receptor in order for the cell to become activated or proliferated in response to contact via its T cell receptor. Such methods are based upon reducing/eliminating function of Cbl-b, reducing/eliminating gene expression of Cbl-b, or knocking out the Cbl-b gene itself.

The invention provides a method for stimulating, expanding, proliferating or inducing CD8$^+$ T cells in a manner that does not require co-receptor co-stimulation, the method comprising, or in certain embodiments the methods consisting essentially of: (a) providing CD8$^+$ T-cells, and (b) reducing Cbl-b activity in the CD8$^+$ T-cells, thereby stimulating, expanding, proliferating, or inducing CD8$^+$ T cells in a manner where CD28 was not costimulated. Cbl-b levels and activity can be reduced by any suitable method known in the art, including but not limited to the methods described herein, for example by delivering an inhibitory RNA of SEQ ID NO:1 into the CD8$^+$ T cells.

The invention provides an isolated, purified population of human cells comprising CD8$^+$ T cells with reduced Cbl-b activity. In certain aspects, the population comprises about 20%, 25%, 30%, 35%, 40%, 45%, 50%, 55%, 60%, 65%, 70%, 75%, 80%, 85%, 90%, 95%, 99% CD8$^+$ T cells. The invention provides an isolated, purified population of human cells consisting essentially of CD8$^+$ T cells with reduced Cbl-b activity. In certain aspects, the CD8+ T cells are isolated from tumor infiltrates from a subject suffering from a tumor, and are modified so as to reduce the level of Cbl-b in the CD8+ T cells.

The invention provides a method for inducing an anti-tumor immune response in a subject, the method comprising: (a) providing a cell population (whether from the subject or from another source) which comprises CD8$^+$ T cells, (b) reducing Cbl-b activity in the CD8$^+$ T-cells, (c) administering the cells of step (b) to the subject. The invention provides a method for inducing or enhancing an anti-tumor immune response in a subject, the method comprising: (a) providing a cell population which comprises CD8$^+$ T cells, with reduced Cbl-b activity in the CD8$^+$ T-cells, (b) administering the cells of step (a) to the subject. In certain aspects, the population comprising the CD8$^+$ T-cells is isolated from tumor infiltrates from a subject. In certain aspects, the population comprises about 20%, 25%, 30%, 35%, 40%, 45%, 50%, 55%, 60%, 65%, 70%, 75%, 80%, 85%, 90%, 95%, 99% CD8$^+$ T cells. In certain aspects, the purified population of cells consists essentially of CD8$^+$ T cells with reduced Cbl-b activity. In certain aspects, the induced or enhanced anti-tumor immune response is a tumor antigen specific immune response. In certain aspects, the induced or enhanced anti-tumor immune response is at least mediated by CD8$^+$ T cells that have a T Cell Receptor (TCR) that is specific to an antigen or antigens of the tumor.

In certain aspect, the cell population is derived from a clonal cell line expressing a predetermined T-Cell Receptor (TCR). In another aspect, the TCR recognizes a tumor antigen. In certain aspects, the CD8$^+$ T-cells are provided from a CD8$^+$ T cell clone. In certain aspects, the CD8$^+$ T cell clone comprises a TCR transgene. In certain aspects, the transgene is specific to a tumor antigen. In certain aspects, the tumor antigen is a tumor specific antigen The invention provides a method for inducing an anti-tumor immune response in a subject suffering from a tumor, the method comprising: (a) isolating from the subject a cell population comprising CD8$^+$ T cells, (b) reducing Cbl-b activity in the CD8$^+$ T cells or ablating Cbl-b in the CD8$^+$ T cells, and (c) administering the cells of step (b) to the subject. In certain aspects, the population comprising the CD8$^+$ T-cells is isolated from tumor infiltrates from a subject. In certain aspects, the population comprises about 20%, 25%, 30%, 35%, 40%, 45%, 50%, 55%, 60%, 65%, 70%, 75%, 80%, 85%, 90%, 95%, 99% CD8$^+$ T cells. In certain aspects, the purified population of cells consists essentially of CD8$^+$ T cells with reduced Cbl-b activity.

In certain aspects, the methods comprise an optional step of stimulating the population comprising CD8$^+$ T cells to proliferate. In other aspects, the methods comprise an optional step of stimulating the population of CD8$^+$ T cells to proliferate in the presence of tumor cells isolated from the subject, so as to increase the number of tumor specific CD8$^+$ T cells, including CD8$^+$ Cbl-b functionally deficient/ablated T cells. In other aspects, the methods comprise an optional step of separating the CD8$^+$ T cells from the cell population and stimulation the CD8$^+$ T cells with tumor cells isolated from the subject so as to increase the number of tumor specific CD8$^+$ T cells. In certain aspects, the methods comprise an additional optional step comprising contacting the tumor specific CD8$^+$ T cells with an anti-CD3 antibody, or IL-2, or a combination thereof, to further increase the number of tumor specific CD8$^+$ T cells, including CD8$^+$ Cbl-b functionally deficient/ablated T cells. The optional steps can be performed before or after the step of reducing Cbl-b activity. In certain aspects, the CD8$^+$ T-cells are isolated from tumor infiltrates. In certain aspects, the CD8$^+$ T-cells are polyclonal. In certain aspects, CD8$^+$ T-cells are isolated from peripheral blood or lymph organs. In certain aspects, proliferation of the CD8$^+$ T-cells is stimulated with anti-CD3 antibody, or exposure to IL-2, or a combination thereof.

In certain aspects, reducing or ablating Cbl-b activity is achieved by one or more: (i) contacting the CD8$^+$ T-cells with a chemical agent which inhibits Cbl-b expression or activity, (ii) introducing iRNA of SEQ ID NO: 1 (5'-CAGGAGTATGAGACAGAAG-3'), which targets Cbl-b in the CD8$^+$ T-cells, (iii) knocking out the gene encoding Cbl-b, or any suitable method, (iv) introducing a dominant negative form of Cbl-b. In certain aspects, the iRNA molecules, or the dominant negative Cbl-b forms can be expressed by retroviral vectors which can comprise a fluorescent marker, for example but not limited to a GFP or any of its variants, thereby allowing to distinguish and/or isolate cells, including CD8+ T cells, which have reduced/ablated Cbl-b activity. In certain aspects, the methods comprise an optional step of specifically separating CD8+ T cells, which have reduced/ablated Cbl-b activity. In certain aspects, the methods comprise an additional optional step of stimulating the population comprising the separated CD8+ T Cbl-b deficient cells to proliferate.

The invention provides a method for identifying an agent which affects Cbl-b expression or activity, the method comprising: (a) stimulating a cell with an anti-CD3 antibody in the absence of co-stimulation (such as co-stimulation with an anti-CD28 antibody), (b) contacting the cell with a candidate agent, (c) measuring levels of cell stimulation or proliferation, wherein an agent which leads to cell stimulation or proliferation is indicative of an agent which downregulates Cbl-b activity or expression. In certain aspects, cell stimulation is measured by level of cytokine expression. In certain aspects, contacting the cell with an agent can be done before, after, or during stimulating the cell with an anti-CD3 antibody in the absence of co-stimulation with anti-CD28 antibody. In certain aspects, the cell which is contacted with an agent is a CD8+T-cell, or CD4+T-cell, or a combination thereof.

The invention provides a screening method for identifying an agent that affects Cbl-b activity, the method comprising: (a) contacting a source of Cbl-b with an agent, (b) determining whether the agent (i) decreases Cbl-b activity, or (ii) affects TCR-induced naïve T cell proliferation, or TCR-downmodulation, or TGF-beta suppression of T cell proliferation. In this method, if the agent decreases TCR-induced TCR-downmodulation, enhances TCR-induced naïve T cell proliferation, or abolishes TGF-beta suppression, then this is indicative that the agent may decrease Cbl-b activity. In certain aspects, the method can further comprise a step of determining whether the agent binds to Cbl-b. In certain aspects, the source is: a cell comprising Cbl-b protein, a cellular extract comprising Cbl-b protein, a recombinant Cbl-b protein, a purified Cbl-b protein, isolated Cbl-b protein, or a synthetic Cbl-b polypeptide.

The invention provides a method for treating a tumor in a subject, the method comprising administering an agent, including an agent as identified by the screening methods of the invention, which inhibits Cbl-b activity, wherein the agent induces an anti-tumor immune response. In one aspect, the agent induces or enhances a CD8+ T cell anti-tumor response. In one aspect, the CD8+ T cell anti-tumor response is tumor antigen specific. In certain aspects, the agent comprises iRNA molecule, for example iRNA of SEQ ID NO: 1 (5'-CAGGAGTATGAGACAGAAG-3').

In certain aspects, the subject treated by any of the methods of the invention suffers from any of the following types of tumors: melanoma, lymphoma, for example spontaneous lymphomas developed by ATM patients, or any solid tumors expressing MHC-I with an antigen that can be recognized by CTLs. In certain aspects, the subject is an animal which can develop tumors, such as human, canine, feline, rodent, and the like.

A significant challenge to efforts aimed at inducing effective anti-tumor immune response is that CD8+ T cells, which play a prominent role in these responses, may be unable to respond to tumors that lack costimulatory signals, often resulting in tolerance or anergy of tumor-specific T cells. The invention provides that the in vitro or in vivo activation of Cbl-b-deficient CD8+ T cells (for example, but not limited to Cbl-b$^{-/-}$ CD8+ T cells), does not depend on CD28 costimulation. For example, in vivo Cbl-b$^{-/-}$ mice, but not wildtype controls, efficiently reject inoculated E.G7 and EL4 lymphomas that do not express B7 ligands. The invention also shows that introduction of Cbl$^{-/-}$ mutation into ATM$^{-/-}$ mice markedly reduces the incidence of spontaneous thymic lymphomas that occur in ATM$^{-/-}$ mice. Immunohistological study shows that E.G7 tumors from Cbl-b$^{-/-}$ but not wildtype mice contain massively infiltrating CD8+ T cells. Thus in certain aspects, the invention provides that adoptive transfer of purified Cbl-b$^{-/-}$ CD8+ T cells but not wildtype CD8+ T cells, leads to efficient eradication of established tumors. The invention provides that ablation of Cbl-b in CD8+ T cells can be used in a method for eliciting immune responses against tumors.

In certain aspects, the invention provides methods for inducing anti-tumor response by adoptive transfer to a subject of CD8+ T-cells with reduced Cbl-b activity. In non-limiting examples, Cbl-b$^{-/-}$ CD8+ T cells may be broadly effective against a large class of somatic tumors, the majority of which do not express costimulatory ligands. The ability of Cbl-b$^{-/-}$ CD8+ T cells to produce substantial cytokine responses and to function independent of CD28 costimulation and CD4+ T cell help might avoid the need to administer large amounts of cytokines or to immunize patients with vaccines designed to enhance costimulatory signaling and helper T cell responses. In certain aspects, the clinical use of tumor-infiltrating lymphocytes (TIL) in adoptive immunotherapy, could be enhanced by ablation of Cbl-b. Ablation of Cbl-b function can be achieved by any suitable method known in the art, for example but not limited to RNAi or expression of a dominant negative form of the cbl-b gene.

The invention provides methods for inducing immune response against a tumor in a subject, including but not limited to methods of adoptive transfer, which do not require co-administration of exogenous cytokines and/or vaccine components to the subject.

BRIEF DESCRIPTION OF THE FIGURES

FIG. 1*a* shows IL-2 and IFN-γ production. Purified CD8+ T cells from wildtype (WT) and Cbl-b$^{-/-}$ mice were stimulated with either plate-bound anti-CD3 or plate-bound anti-CD3+ soluble anti-CD28 antibodies. IL-2 and IFN-γ producing cells were visualized by intracellular staining and analyzed by flow cytometry. Shown are contour plots of intracellular staining for IL-2 and IFN-γ expression in CD8+ T cells. Percentages of IL-2 and IFN-γ producing cells are indicated in the plots. FIG. 1*b* shows TCR-induced proliferative response. Purified CD8+ T cells from wildtype and Cbl-b$^{-/-}$ mouse lymph nodes and spleens were stimulated with various concentrations of anti-CD3 antibodies in the presence or absence of anti-CD28 antibodies. Cell proliferation was determined by $^3$[H]-thymidine incorporation and expressed as mean+/−SD for triplicate samples. Shown are representatives of more than three independent experiments. FIG. 1*c, d* shows resistance of Cblb$^{-/-}$ CD8+ T cells to TGF-β suppression. Histograms (FIG. 1*c*) show CSFE intensities of labeled Cblb$^{-/-}$ and WT CD8+ T cells after 3 days of anti-CD3 and anti-CD28 stimulation. Cells were cultured in the absence or presence of different concentrations of TGF-β as indicated in the figure. Contour plots (FIG. 1*d*) show the IFN-γ production in the absence or presence of TGF-β. Percentages of IFN-γ+ cells are indicated in the plots.

FIG. 2*a* shows Growth rates of inoculated E.G7 tumors. $10^6$ E.G7 cells were inoculated into the flanks of wildtype (WT) or Cbl-b$^{-/-}$ mice by s.c. injection. Tumor growth was documented as total volume of tumor size. Shown at the top are the growth rates of E.G7 tumors in one representative experiment. Each curve represents one individual mouse. The bottom bars represent the percentages of mice with tumor growth by the end of the 7$^{th}$ week after tumor inoculation. FIG. 2b and FIG. 2c show growth rates of EL4 tumors. Low-dose ($5\times10^4$ cells/mouse) and high-dose ($2.5\times10^5$ cells/mouse) EL4 cells were injected s.c. into the flanks of five WT and 5 Cbl-b$^{-/-}$ mice, respectively. The diagrams showed respectively representative results of 4 or 2 independent experiments inoculated with either low-dose (FIG. 2b) or high-dose tumors (FIG. 2c). Each curve represents one individual mouse. FIG. 2d shows percentages of surviving mice (WT, n=13; Cbl-b$^{-/-}$, n=29) during the course of tumor growth. When the tumor volume reached approximately 5,000 mm$^3$, the mice were euthanized and recorded as dead. FIG. 2e shows Rejection of EL4 tumors by Cbl-b$^{-/-}$CD28$^{-/-}$ mice. EL4 cells ($5\times10^4$ cells/mouse) were injected, and tumor growth was monitored as described in B. The number of mice with tumor growths is indicated at the top of each column.

FIGS. 3A-3F show that tumor rejection in Cbl-b$^{-/-}$ mice is mediated by Cbl-b$^{-/-}$ CD8$^+$ T cells. FIG. 3a shows immunohistology of tumor-infiltrating CD8$^+$ cells. Shown are sections of tumors stained with H&E (left) or anti-CD8 antibody (right). CD8$^+$ cells are FITC positive (green) cells. Tumors were from wildtype (WT) and Cbl-b$^{-/-}$ mice at 7th or 19th day post inoculation. FIG. 3b shows Flow cytometric analysis of tumor infiltrates. Tumor infiltrates were prepared from tumors from wildtype (WT) or Cbl-b$^{-/-}$ mice. These cells were stained with anti-TCRβ, anti-CD8, and anti-CD44 antibodies and analyzed on LSR II. Shown at the top left are contour plots of CD8 and TCRβ expression on tumor-infiltrating cells. The percentages of CD8$^+$ TCRβ$^+$ cells are indicated in the plots. The percentages of CD8$^+$ TCRβ$^+$ T cells in total tumor infiltrates are summarized and shown as bars (top right). Histograms (bottom) show the levels of TCRβ and CD44 expression on the infiltrating CD8$^+$ T cells. FIG. 3c Eradication of established E.G7 tumors by adoptively transferred Cbl-b$^{-/-}$ CD8$^+$ T cells. $10^6$ E.G7 cells were inoculated into C57BL/6 mice by s.c. injection. Seven days after the inoculation, $3\times10^6$ purified wildtype (WT) or Cbl-b$^{-/-}$ CD8$^+$ T cells were transferred into the tumor-bearing mice by i.v. injection. Shown are the tumor volumes at different time points after the CD8$^+$ T cell transfer. The curves represent the size of tumors in individual mice. Solid bars (bottom) represent percentages of mice with tumor. Total numbers of mice included in these experiments are indicated in the plot. FIG. 3d shows flow cytometric analysis of tumor infiltrates. Tumor infiltrates were prepared from tumors from WT or Cbl-b$^{-/-}$ mice. These cells were stained with anti-TCRβ, anti-CD8, anti-CD4, and anti-CD44 antibodies and analyzed on LSR II. Foxp3$^+$ (Treg) cells were identified by intracellular staining with an anti-Foxp3 antibody according to manufacture protocol. Shown at the top left are contour plots of CD8 and TCRβ expression on tumor-infiltrating cells from 1 of 3 independent experiments. The percentages of CD8$^+$ TCRβ$^+$ cells are indicated in the plots. The percentages of CD8$^+$ TCRβ$^+$, CD4$^+$, and Treg infiltrates in total tumor infiltrates are summarized and shown as bars. *P<0.001, **P<0.005. Histograms show the levels of TCRβ and CD44 expression on the infiltrating CD8$^+$ T cells. FIG. 3e shows eradication of established E.G7 tumors by adoptively transferred Cbl-b$^{-/-}$ or Cbl-b$^{-/-}$ OT1 CD8$^+$ T cells. 106 E.G7 cells were inoculated into C57BL/6 mice by s.c. injection. Seven days after the inoculation, $3\times10^6$ purified WT or Cbl-b$^{-/-}$ CD8$^+$ T cells (top) or WT OT1 or Cbl-b$^{-/-}$ OT1 CD8$^+$ T cells (bottom) were transferred into the tumor-bearing mice by i.v. injection. Shown at the left are the tumor volumes at different time points after the CD8$^+$ T cell transfer. Genotypes of the donor cells are indicated on the top of each plot. Results are from 1 of 5 or more independent experiments. FIG. 3f shows percentages of surviving recipient mice (WT, n=11; Cbl-b$^{-/-}$, n=13) that received WT or Cbl-b$^{-/-}$ CD8$^+$ T cells. When the tumor volume reached approximately 5,000 mm$^3$, the mice were euthanized and recorded as dead.

FIG. 6a shows In vitro T-cell proliferation and IL-2 production. Splenic CD4$^+$ T cells from Cbl-b$^{-/-}$ and wildtype mice were purified using a CD4$^+$ T-cell purification kit (Accurate). Purified CD4$^+$ T cells ($10^5$ cells/well, 96 well plate) were stimulated with either plate-bound anti-CD3 antibody (2C11, 5 μg/ml) alone, or with anti-CD3 (plate-bound) and anti-CD28 (soluble) antibodies (37.51, 2 μg/ml). Cell proliferation and IL-2 secretion were determined according to a published protocol (56, 60). FIG. 6b shows Cbl-b$^{-/-}$ mutation rescues T-dependent-antibody response in CD28$^{-/-}$ mice. For T-cell proliferation assay (left), splenic CD4$^+$ T cells were purified and cell proliferation, after anti-CD3, anti-CD3 & anti-CD28 antibodies, or PMA & inomycin stimulation, were determined as described above. For T-dependent antibody responses (right), Cbl-b$^{-/-}$ CD28$^{-/-}$, CD28$^{-/-}$, and wild-type mice were immunized with 100 μg NP-KLH in alum adjuvant by i.p. injection. 10 days later, mice were bled, and titers of serum anti-NP antibodies of various Ig isotypes were determined by ELISA. Anti-NP antibody titers of various Ig isotypes in wild-type mice were arbitrarily shown as 100%. Data represented mean values of antibody titers from 5-8 mice (2-3 month-old) of each genotype.

FIG. 8a and FIG. 8b show rejection of E.G7 tumors by Cbl-b$^{-/-}$ mice. About $10^6$ cells per mouse were inoculated subcutaneously into female wildtype littermates (WT) and Cbl-b$^{-/-}$ mice (8-weeks-old) on day 0. The growth rates of the inoculated tumors were determined by the sizes of the tumors and plotted in diameter according to (36) (FIG. 8a). The death rates represented the percentage of mice that either died within 5 weeks after tumor inoculation or sacrificed when tumors size grew bigger than 20 mm in diameter (FIG. 8b). Results represent 10 C57BL/6 and 18 Cbl-b$^{-/-}$ mice. FIG. 8c and FIG. 8d show rejection of EL4 and B16 tumors by Cbl-b$^{-/-}$ mice. $2.5 \times 10^4$ EL4 or $1.0 \times 10^4$ B16 cells were inoculated into the flanks of C57BL/6 or Cbl-b$^{-/-}$ mice (8-10 weeks-old) by subcutaneous injection.

FIG. 9a shows depletion of T cells. Anti-CD4 and anti-CD8 antibodies (100 μs/mouse) were injected into Cbl-b$^{-/-}$ mice daily by iv injection for 3 consecutively days. 2 days after the last injection, mice were sacrificed, and splenic and lymph node cells were analyzed by FACS. Cells were stained with anti-CD3 (a T-cell marker) and anti-B220 (a B-cell marker) or with anti-CD4 and anti-CD8 antibodies, respectively. FIG. 9b shows growth of E.G7 tumors in T-cell-depleted Cbl-b$^{-/-}$ mice. About $10^6$ E.G7 cells were injected subcutaneously into the flanks of anti-CD4 and anti-CD8 antibody-treated (Anti-CD4,8) Cbl-b$^{-/-}$ (black) (n=3) and non-treated (NT) Cbl-b$^{-/-}$ (red) mice (n=5), respectively. The growth rate of tumors was documented weekly.

FIG. 10a shows immunohistological analysis of infiltrating leukocytes infiltrates in tumor tissues. Mice were sacrificed 20 days after tumor inoculation. Tumor tissues from wildtype (B6) and Cbl-b$^{-/-}$ (Cbl-b$^{-/-}$) mice were collected and imbedded in Tissue-Tek (Sakura). CD8$^+$ T cells (green) in the cryosections were stained with biotinated-anti-CD8 antibody followed by streptavidin-Alexa 488 (Molecular Probes). H&E: Hematoxylin and eosin staining. FIG. 10b shows flow cytometry analysis of tumor infiltrating CD8$^+$ T cells. Tumor tissues from C57BL/6 and Cbl-b$^{-/-}$ mice were collected on day 20 after tumor cell inoculation. Tissues were cut into small pieces (less then 2 mm in diameter) and digested with collagenase (1 μg/ml) at 37° C. for 30 min. After digestion, dead cells were removed by Ficoll centrifugation. Viable cells were collected from the interface, washed three times with DMEM medium containing 5% FCS, stained with anti-CD8α (PE-Cy7), anti-TCRβ (PE), anti-CD62L (FITC), and anti-CD44 (APC) antibodies, and then analyzed on a FACS LSR II. Shown on the top are CD8 and TCRβ staining of cells from tumors from C57BL/6 (B6) or Cbl-b$^{-/-}$ mice. Percentages of CD8$^+$ T cells (gated) are shown in the plots. The bottom histograms show respectively the expression of TCRβ, CD62L or CD44 on the gated CD8$^+$ T cells.

FIG. 12a shows histograms of CSFE intensity of the gated CD8$^+$ T cells. FIG. 12b Statistics of cell proliferation measured based on three independent CFSE labeling experiments. FIG. 12c Intracellular staining of IFN-gamma in CD8$^+$ T cells cultured in the absence or presence of TGF-beta.

FIG. 13a shows a schematic map of the hCD2-based retroviral vector for siRNA expression. The elements of a viral 5'-LTR, a H1 promoter (Pro (H1)), siRNA, an ubiquitin promoter (Pro (Ubi)), and a 3'-LTR are indicated. FIG. 13b shows a Western blot analysis of Cbl-b expression in transiently transfected 293T cells. The Cbl-b siRNA transfected 293T cells were lysed, Cbl-b in the lysates were western blotted and detected by an anti-Cbl-b antibody. Protein loading was quantified by an anti-actin antibody. FIG. 13c shows retroviral infection of cultured T cells. Lymph node T cells from wildtype C57BL/6 mice were activated in vitro and infected with an empty hCD2-based siRNA-expression retroviral vector as described in the text. Retrovirus infected cells were visualized by FACS after staining the cells with an anti-human CD2 antibody. The percentage of hCD2$^+$ cells is indicated in the histograms.

FIG. 16a shows a flow cytometric analysis of CFSE intensity of CD8+ T cells after three days of the stimulation. Dividing cells showed lower CFSE intensity as compared to non-stimulated cells. FIG. 16b shows TGF-beta dose-dependent suppression of T cell proliferation. Shown are the results of $^3$H-thymidine incorporation of Cbl-b−/− CD8+ T cell proliferation. FIG. 16c INF-gamma production. Shown are intracellular staining of IINF-gama production in WT and Cbl-b−/− CD8+ T cells in the presence or absence of TGF-beta suppression. Percentages of INF-gama positive cells are indicated in the plots.

DETAILED DESCRIPTION

Definitions

Figure 1A:
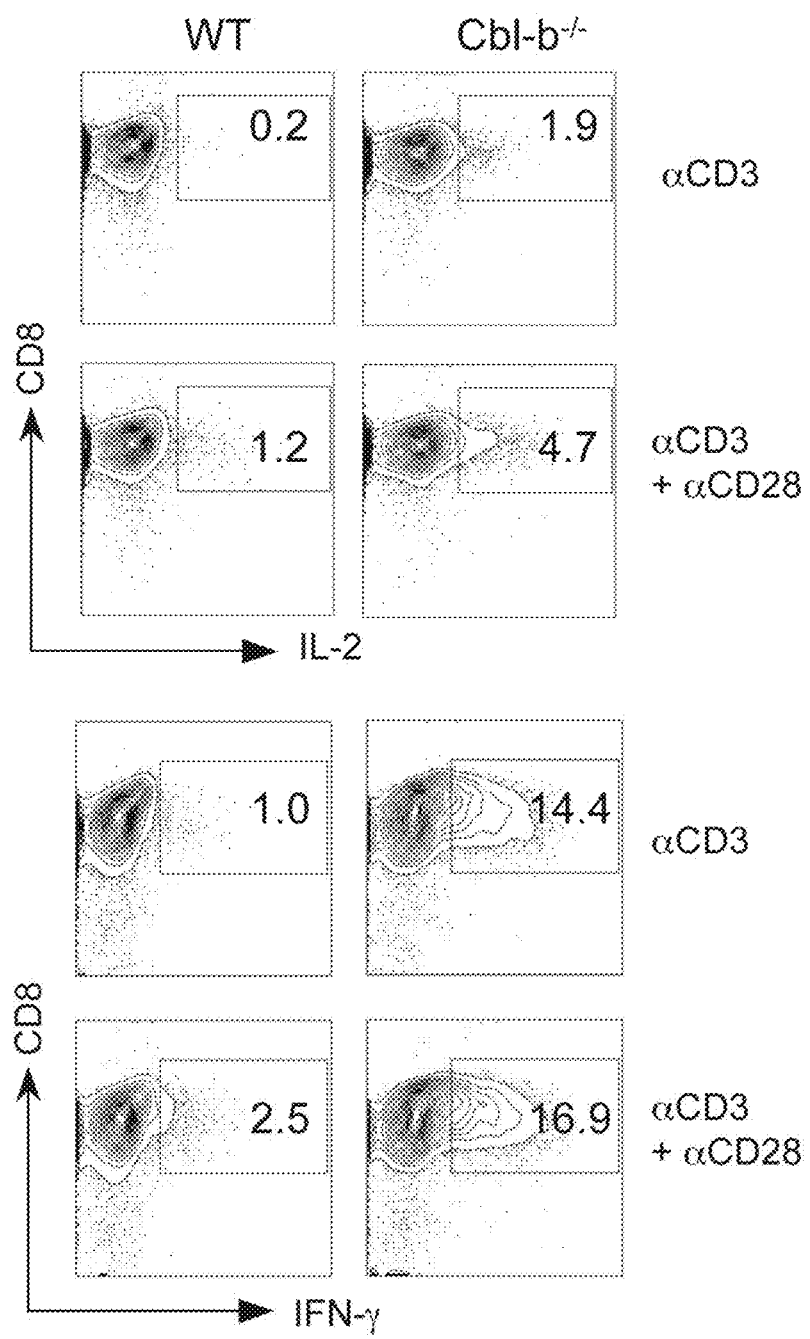
FIGS. 1A-1D show CD28-independent proliferation and cytokine production by Cbl-b$^{-/-}$ CD8+ T cells.

"Super killer T-cells" are CD8+ T cells which can mount an immune response in the absence of co-stimulatory signal.

The term "Cbl-b deficiency" is used interchangeably with the term "Cbl-b ablation" to indicate Cbl-b deficiency due to knock out of the cbl-b gene, and reduction in Cbl-b protein activity due to knock down of Cbl-b function by iRNA, or by expression of dominant negative form, including but not limited to dominant negative mutant, or by an agent which targets Cbl-b, or by any other suitable method.

Adoptive transfer of CD8+ T cells is a method for cellular immunotherapy which comprises administering specific effectors of immunity to a subject host organism, thus bypassing obstacles in the host organism that may prevent the generation of an effective immune response in vivo. Adoptive transfer can comprise removing a population comprising CD8+ T cells from a subject, enriching the population for CD8+ T cells either by isolation of CD8+ T cells or removal of other cell types from this population, optionally expanding the population of CD8+ T cells, and administering the enriched population of CD8+ T cells to a subject. Adoptive transfer can comprise administering a population of CD8+ T cells from a cell line, including a clonal cell line of CD8+ T cells. Adoptive transfer permits the use of large number of effector T cells, isolated from a subject, or derived from clones and/or lines with defined specificity and function.

The terms CD8+ T cells and CTLs are used interchangeably throughout the specification. It is well known in the art, that immune activation of CD8+ T cells generates a population of effector cells with lytic capability called cytotoxic T lymphocytes, or CTL. These effector cells have important roles in the recognition and elimination of malignant cells and pathogens. In general, CTLs are CD8+ and are therefore class I MHC restricted, although in rare instances CD4+ class II-restricted T cells have been shown to function as CTL. Since virtually all nucleated cells in the body express class I MHC molecules, CTL can recognize and eliminate almost any altered body cell. CD8+ T cells recognize antigen presented on HLA class I molecules of tumor cells through T cell receptors. The CTL-mediated immune response can be divided into two phases, reflecting different aspects of the cytotoxic T-cell response. The first phase involves the activation and differentiation of CD8+ T cells into functional effector CTLs. In the second phase, CTLs, recognize antigen—class I MHC complexes on specific target cells, initiating a sequence of events that culminates in target-cell destruction. Further detailed discussion of the process is found at Chapter 15 of the Second Edition of "Immunology" by Janis Kuby, W.H. Freeman and Company (1991).

While stimulation of T cells through TCR and costimulatory receptors, such as CD28, leads to T cell activation, triggering of T cells through the TCR alone results in a non-responsive state (anergy) of these cells (Schwartz, R. H. 1992.) The importance of costimulation for anti-tumor immune response has been demonstrated by experiments in which the enforced expression on tumor cells of B7 or ICOS/B7h, ligands for CD28, results in efficient eradication of inoculated tumors (Townsend, S. E., and J. P. Allison. 1993; Chen, et al., 1994; Wallin, et al., 2001; Liu, X., et al., 2001; Yu, X., R et. al., 1998) However, this approach to immunotherapy is practically difficult because of the lack of an efficient way to express a costimulatory molecule in all tumor cells. An alternative to this approach is the generation of T cells that can by-pass the requirement for CD28 costimulation during activation. Such an approach may allow direct activation of tumor-specific CTLs by tumor cells in the absence of costimulatory ligands, thus representing a powerful therapeutic tool against cancer.

In certain aspects, the invention provides methods that involve the use of CTLs which are deficient in Cbl-b function and have a TCR specific to a tumor antigen. Such CTLs can have for example a transgene that encodes a TCR specific to a tumor antigen. In certain aspects, such CTLs can be derived from a polyclonal population from tumor tissue (Ramarithanam et al., 2003). In one embodiment, tumor-specific Cbl-b$^{-/-}$ CTLs can thus be generated by knocking-down Cbl-b function using a Cbl-b siRNA or a dominant negative form of Cbl-b in CTLs derived from tumors.

Cbl-b Protein

Cbl proteins are RING-finger domain-containing E3 ubiquitin ligases involved in various membrane-receptor signaling events (Lupher, et al., 1999; Joazeiro et al., 1999; Liu, Y. C. 2004). Previous experiments have shown that Cbl-b, a member of the Cbl family of proteins, plays a critical role in peripheral T cell activation (Chiang, et al., 2000; Bachmaier, et al., 2000). Remarkably, Cbl-b$^{-/-}$ CD4$^+$ T cells have circumvented dependence on costimulatory signals for their activation, as they proliferate vigorously and secret large amounts of IL-2 upon TCR stimulation in the absence of CD28 costimulation. These results thus underscore the role of Cbl-b as a key regulator of CD28 costimulatory signaling and suggest that CTLs deficient in Cbl-b may respond to and mount an efficient response against tumors that lack costimulatory signals.

The Cbl proteins belong to a family of multi-adaptor molecules involved in various membrane-receptor signaling (46-48). In mammalian cells, there are three members of Cbl family proteins, c-Cbl, Cbl-b, and Cbl-3. Among these members, c-Cbl and Cbl-b are co-expressed in lymphocytes (49-51). Structurally, c-Cbl and Cbl-b share high sequence homology in the C-terminal region that contains a conserved PTB (phosphotyrosine-binding) domain and a ring-finger motif, the latter may associate with E2 ubiquitin-conjugating enzymes (52, 53). In the N-terminal portion, both c-Cbl and Cbl-b contain multiple proline-rich motifs, as well as several tyrosine residues that become phosphorylated upon activation by various receptors (52). The protein sequences of the N-terminal region between c-Cbl and Cbl-b are significantly different, suggesting that these two molecules may exert distinct functions through this region.

The importance of c-Cbl and Cbl-b in TCR signaling, T-cell development and activation has been demonstrated recently by several groups using gene-targeted mice (54-58). At least two studies have shown that c-Cbl deficiency (c-Cbl$^{-/-}$) significantly enhances TCR signaling in thymocytes, but not in peripheral T cells (54, 57). In contrast, analysis of Cbl-b deficient (Cbl-b$^{-/-}$) mice reveals that Cbl-b plays a critical role in peripheral T cell activation, but not in thymocyte development, as they may respond efficiently to low antigen stimulation (55, 56). Remarkably, Cbl-b$^{-/-}$ CD4$^+$ T cells have lost the dependence on costimulatory signals for the activation, as they proliferate vigorously and secret large amounts of IL-2 upon TCR stimulation in the absence of CD28 costimulation (55, 56). Importantly, Cbl-b$^{-/-}$ T cells are not anergized under the conditions that normally induce T cell anergy (non-responsiveness). As a result, Cbl-b$^{-/-}$ mice become susceptible to autoimmune diseases. These results therefore underscore Cbl-b as a key regulator for TCR and CD28 costimulatory signaling and T cell activation, and suggest that modulation of the Cbl-b pathway could be a powerful approach to generate the "super killer" T cells that are responsive to the stimulation by low affinity antigens and independent of CD28 costimulation.

There is no clear evidence showing that the biological function of Cbl proteins is linked to their ubiquitin ligase activity, even though Cbl promotes ubiquitination of several proteins. In certain embodiments, the invention provides methods to determine whether the contribution of Cbl-b to the double knock-out (dKO) phenotype is in fact due to ubiquitin ligase activity. In other aspects, the invention provides a retroviral vector carrying a ubiquitin-disabled Cbl-b. In other aspects, the invention provides ES cell clones with the designed ubiquitin-disabled Cbl-b KI mutation.

In certain embodiments the invention provides methods to determine the role of the ubiquitin ligase function of Cbl-b in anti-tumor T cell responses. In other embodiments, the invention provides methods to determine whether abolishment of the ubiquitination ligase function of Cbl-b, provides CD8+ T cells with the capacity to reject the various tumors. Identification of the domain of Cbl-b critical for its biological function is an important for the development of drugs that may suppress Cbl-b function. Cbl-b is an E3 ubiquitin ligase and promotes ubiquitination of several signaling proteins such as p85 PI-3 kinase and Vav in T cells, suggesting that Cbl-b regulates T cell anti-tumor response through ubiquitination function. In certain aspects, the invention provides that disruption of the ubiquitination function of Cbl-b is sufficient to render T cell responsiveness to tumor-antigen. The ubiquitination function of Cbl-b is a potential drug target to inactivate Cbl-b function. In certain aspects, the invention provides methods to determine whether the ubiquitin ligase function of Cbl-b is required for costimulation signals during T cell activation. In other aspects, the invention provides methods to determine whether inactivation of the ubiquitin ligase activity of Cbl-b renders T-cell responsiveness against tumors.

Cbl-b$^{-/-}$ CD8$^+$ T Cells do not Require Co-Stimulation

Previously it was shown that activation of Cbl-b$^{-/-}$ CD4$^+$ T cells is independent of CD28 costimulation (Chiang et al., 2000; Bachmaier et al, 2000). In certain aspects, the invention provides that Cbl-b$^{-/-}$ CD8$^+$ T cells respond efficiently to antigen stimulation even without CD28 costimulation. In certain embodiments, the invention provides that Cbl-b$^{-/-}$ CD8$^+$ T cells produce large amounts of interleukin-1 (IL-2) and interferon-gamma (IFN-gamma) upon stimulation by anti-CD3 antibody alone, indicating that the Cbl-b$^{-/-}$ CTLs can be fully activated by TCR triggering without CD28 costimulation and help from CD4$^+$ T cells. In certain aspects, the invention provides that Cbl-b$^{-/-}$ CD8$^+$ T cells by-pass dependence on CD28 signaling. In certain aspects, the invention provides that Cbl-b$^{-/-}$ CD8$^+$ T cells efficiently eradicate syngenic tumors. In certain aspects, the invention provides that Cbl-b$^{-/-}$ CD8$^+$ T cells are responsible for the eradication of tumors.

In certain aspects, the invention provides isolated Cbl-b$^{-/-}$ CD8$^+$ T cells. The invention provides that Cbl-b$^{-/-}$ T cells response in vitro is hyperactive, independent of costimulation, and not inhibited by TGF-beta. The invention further provides that Cbl-b$^{-/-}$ mice mount a normal immune response in vivo even in the absence of CD28. The invention also provides that Cbl-b regulates T cell responsiveness through an ubiquitination-dependent mechanism.

In certain aspects, the invention provides a clonal population of Cbl-b$^{-/-}$ CD8$^+$ T cells, wherein all of the T cells in the population have same TCR specificity. In one aspect, the clonal population comprises CTLs which are Cbl-b$^{-/-}$ and express a TCR specific to a tumor antigen. In certain aspects, the invention provides that Cbl-b$^{-/-}$ T cells mount an efficient anti-tumor response in vivo. In a non-limiting example, this is demonstrated by the inhibition of growth of E.G7, EL4 and B16 tumors in Cbl-b$^{-/-}$ mice. The majority of Cbl-b$^{-/-}$ mice either do not permit tumor growth at all or exhibit tumor regression within the same timeframe. Furthermore, there is massive infiltration of CD8$^+$ T cells in tumor tissues from Cbl-b$^{-/-}$ mice. In certain embodiments, the adoptive transfer of purified Cbl-b$^{-/-}$ CD8$^+$ T cells eradicates the established E.G7 tumors. The invention provides that tumor specific Cbl-b deficient CD8$^+$ T cells, for example but not limited to Cbl-b$^{-/-}$ CD8$^+$ T cells, can be used as "super killer" T cells for tumor therapy.

In certain aspects, the invention provides that Cbl-b$^{-/-}$ CD8$^+$ T cells are responsible for tumor rejection. Furthermore, Cbl-b$^{-/-}$ T cells are resistant to TGF-beta suppression, which suggests that Cbl-b$^{-/-}$ CD8$^+$ T cells may reject tumors through breaking down multiple hurdles that tumors usually use to prevent an anti-tumor immune response. In certain embodiments the invention provides methods to quantitatively determine whether Cbl-b$^{-/-}$ CTLs can mount immune responses against various tumors, and to quantitatively examine the efficiency of tumor-specific CD8$^+$ T cells required for tumor rejection, and the long-term effect of Cbl-b$^{-/-}$ CD8$^+$ T cells in the eradication of established tumor. The invention provides methods to examine whether Cbl-b$^{-/-}$ CTLs can eradicate tumors that prevent T cell response through TGF-beta, and tumor barrier. The invention also provides that Cbl-b$^{-/-}$ mice efficiently reject both strong and weak antigenic tumors, and adoptive transfer of Cbl-b$^{-/-}$ CD8$^+$ T cells eradicates established tumors. The invention also provides methods which determine the mechanisms by which Cbl-b$^{-/-}$ CTLs mount immune responses against immunogenic tumors. The invention also provides that ablation of Cbl-b in tumor-specific CTLs renders them responsive against various tumors.

The invention also provides that Cbl-b$^{-/-}$ CD8$^+$ T cells are resistant to TGF-beta suppression, a feature that can be helpful to overcome the negative effect of certain tumor environment. In other aspects, the invention provides that Cbl-b$^{-/-}$ CD8$^+$ T cells are resistant to TGF-beta suppression, suggesting that these cells can respond to tumors that are protected by TGF-beta produced by either tumor itself or immune cells such as CD4$^+$ CD25$^+$ regulatory T cells. Various embodiments demonstrate that Cbl-b$^{-/-}$ CD8$^+$ T cells can be used as "super killers" against various cancers. In certain aspects, the invention provides methods to determine the long-term effect of Cbl-b$^{-/-}$ CD8$^+$ T cells in tumor therapy by using well-studied transgenic systems, as well as various tumor models that prevent immune response through different mechanisms. Other methods can determine the immune memory against the tumor cells, wherein the long-term effect of the anti-tumor response in tumor-regressed mice can be analyzed.

In certain aspects, the invention provides that ablation of Cbl-b prevents spontaneous tumors in ATM$^{-/-}$ deficient cells, including ATM$^{-/-}$ mice. The invention further provides that germ-line ablation of Cbl-b in ATM$^{-/-}$ mice results in a marked reduction of spontaneous tumors, and a consequently increased life span. In certain aspects, the invention provides that systemic inhibition of Cbl-b function is an effective approach to reduce the incidence of tumors. The invention further provides that Cbl-b$^{-/-}$ mice are resistant to inoculated E.G7 and EL4 tumors, and Cbl-b$^{-/-}$ ATM$^{-/-}$ double mutant mice exhibit a significantly lower incidence of spontaneous lymphomas than do mice expressing Cbl-b. In other aspects, the invention provides that adoptive transfer of Cbl-b$^{-/-}$ CD8$^+$ T cells is sufficient to eradicate established E.G7 tumors in wild-type recipient mice.

Methods for Inducing Immune Response in the Absence of Co-Stimulation to Treat Tumors In certain aspects, the present invention provides methods for using Cbl-b deficient CTLs, including but not limited to Cbl-b$^{-/-}$ CTLs, as "super killer" T cells for cancer therapy. In certain embodiments Cbl-b$^{-/-}$ mice reject inoculated high and low immunogenic tumors, and Cbl-b$^{-/-}$ CD8$^+$ T cells are sufficient to mediate the anti-tumor immune response in tumor-bearing mice. The invention provides that Cbl-b-ablated CD8$^+$ T cells are effective tools in the treatment of cancers, including human cancer.

In certain aspects, the invention is directed to methods for using Cbl-b deficient CD8$^+$ T cells in tumor immunotherapy, including but not limited adoptive transfer methods, to induce anti-tumor immune response in a subject. In certain embodiments, the method comprises providing a population of cells, which comprises CD8$^+$ T cells with tumor specificity, reducing Cbl-b activity, and administering the CD8$^+$ T cells with reduced Cbl-b activity to a subject. The population of cells used in the methods of the invention comprises at least 40%, 50%, 60%, 70%, 75%, 80%, 85%, 86%, 87%, 88%, 89%, 90%, 91%, 92%, 93%, 94%, 95%, 96%, 97%, 98%, 99% CD8$^+$ T cells. In certain embodiments, the method comprises providing a population of cells, which consists essentially of CD8$^+$ T cells, reducing Cbl-b activity, and administering the CD8$^+$ T cells with reduced Cbl-b activity to a subject.

A potential limitation in adoptive methods is the need to generate and transfer by infusion to a subject a sufficient number of CD8$^+$ T cells. The number of CD8$^+$ T cells that can result in effective or sufficient immune response depends on multiple factors, such as tumor antigen burden, the replicative ability of the transferred cells, and the ability of the transferred cells to persist in the host. In certain aspects, the invention provides methods to determine the number of CD8$^+$ T cells necessary to induce immune response in a subject. In certain embodiments, the methods can transfer in a subject about 5×10$^5$ CD8$^+$ T cells, 1×10$^6$ CD8$^+$ T cells, 5×10$^6$ CD8$^+$ T cells, 1×10$^7$ CD8$^+$ T cells, 5×10$^6$ CD8$^+$ T cells. Other embodiments can include multiple transfers of CD8$^+$ T cells in a subject.

In certain embodiments, the population of cells which comprises CD8$^+$ T cells can be obtained from T cells from tumor infiltrates. Methods for obtaining, isolating and purifying T cells from tumor infiltrates are known in the art and are within the scope of the invention. Obtaining CD8$^+$ T cell from tumor infiltrates comprising T cells is advantageous because T cells in the tumor mass can recognize tumor antigen presented by tumor cells. However, most antigenic tumors are not rejected efficiently by these T cells. The critical mechanisms that prevent T-cell mediated tumor rejection include lack of proper signals from the TCR or costimulatory receptors from tumor cells and/or anergy or suppression of tumor-specific T cells by tumor environment or tumor itself. Thus, a challenging task in tumor immunotherapy is to develop strategies that may activate tumor-specific CTLs inside tumors with minimal or without a severe damage to the normal tissues. CD8$^+$ T cells derived from tumor infiltrates can be modified by reducing Cbl-b activity thus providing Cbl-b deficient CD8$^+$ T cells. The ability of Cbl-b$^{-/-}$ CD8$^+$ T cells to reject antigenic tumors provides a new avenue in tumor immunotherapy, wherein administering Cbl-b$^{-/-}$ CD8$^+$ T cells, derived from tumor infiltrates, can induce specific antitumor immune response.

In certain embodiments, the methods for using Cbl-b deficient CD8$^+$ T cells in tumor immunotherapy to induce anti-tumor immune response in a subject, comprise isolating, and/or purifying CD8+ T cells from tumor infiltrates from subjects. The method can optionally comprise a step of stimulating the expansion and proliferation of the isolated CD8$^+$ T cells. In certain embodiments, the step expansion and proliferation can be performed before Cbl-b activity is reduced. In other embodiments, the step of expansion and proliferation can be done after Cbl-b activity is reduced. Methods for inducing expansion and proliferation of CD8$^+$ T cells in a cell culture are well-known in the art. In certain embodiments, expansion and proliferation can be stimulated by treatment of cells with anti-CD3 antibody, and/or in the presence of IL-2.

In other aspects, the invention is directed to methods of using adoptive transfer of Cbl-b deficient $CD8^+$ T, such as Cbl-$b^{-/-}$ $CD8^+$ T cells, as a therapeutic tool for cancer treatment. For example, adoptive transfer of purified Cbl-$b^{-/-}$ $CD8^+$ T cells into E.G7 tumor-bearing wild-type mice eradicates the established tumor. In another example, Cbl-$b^{-/-}$ mice also reject physiological tumors such as EL4 and B16.

In certain aspects, the invention provides methods for inducing anti-tumor response in a subject by adoptive transfer of $CD8^+$ T-cells with reduced Cbl-b activity. The adoptive transfer approach has several advantages. In non-limiting examples, Cbl-$b^{-/-}$ $CD8^+$ T cells may be broadly effective against a large class of somatic tumors, the majority of which do not express costimulatory ligands. The ability of Cbl-$b^{-/-}$ $CD8^+$ T cells to produce substantial cytokine responses and to function independent of CD28 costimulation and $CD4^+$ T cell help might avoid the need to administer large amounts of cytokines or to immunize patients with vaccines designed to enhance costimulatory signaling and helper T cell responses. In certain embodiments, the clinical use of tumor-infiltrating lymphocytes (TIL) in adoptive immunotherapy, could be enhanced by ablation of Cbl-b. Ablation of Cbl-b function can be achieved by any suitable method known in the art, for example but not limited to RNAi or expression of dominant negative form of the cbl-b gene.

In a non-limiting example of an adoptive transfer method of the present invention, $CD8^+$ T cells are isolated and purified from tumor infiltrates from a subject suffering from a tumor. The levels of Cbl-b are reduced in these isolated and purified $CD8^+$ T cells, for example by stable transfection with a retroviral vector expressing siRNA which targets Cbl-b, to produce Cbl-b deficient $CD8^+$ T cells. In certain embodiments, the retroviral vector expressing the inhibitory RNA can comprise a fluorescent marker, such as but not limited to GFP or any of its variants. Such fluorescent marker can allow for detection of $CD8^+$ T cells, which have become Cbl-b deficient. The isolated and purified Cbl-b deficient $CD8^+$ T cells can be expanded ex vivo to a number of cells suitable for infusion to the subject suffering from tumor. In certain embodiments, the isolated and purified Cbl-b deficient $CD8^+$ T cells can be expanded and/or enriched for tumor specific $CD8^+$ T cells by exposure and stimulation with tumor cells derived from the subject's tumor.

The present invention contemplates various routes of administering CTLs in any of the methods of the present for the treatment of a subject suffering from a tumor. In certain aspects, CTLs can be administered by i.v. delivery. In other aspects, CTLs can be administered directly to a tumor site. In certain embodiments, multiple infusions of such Cbl-b deficient $CD8^+$ T cells are contemplated.

In vivo non-responsiveness of CTLs to tumors may involve active suppression of CTLs or lack of appropriate recognition of tumor cells by CTLs. In certain embodiments, costimulation-independent activation of Cbl-$b^{-/-}$ T cells is responsible for the observed anti-tumor response. In other embodiments, mechanisms other than CD28 independent $CD8^+$ T cell activation can contribute to the tumor rejection. In certain embodiments, massive infiltration of Cbl-$b^{-/-}$ $CD8^+$ T cells in tumor mass may result from altered cell adhesion and migration. In addition, it has been shown that Cbl-$b^{-/-}$ T cells may escape anergic fate under conditions that normally induce immune tolerance in vivo (Jeon, M. S. et al., 2004). Cbl-$b^{-/-}$ T cells may therefore be resistant to tolerance induction by tumor cells, consequently providing a better immune surveillance against newly transformed or inoculated tumor cells. Finally, it has been demonstrated that the CTL response against tumors can be inhibited by $CD25^+$ regulatory T cells ($T_{reg}$) (Somasundaram et al., 2002.) $CD25^+$ $T_{reg}$ may exert immune suppression through secretion of TGF-β (Kronenberg, M., and A. Rudensky. 2005). In certain embodiments, the invention provides that Cbl-$b^{-/-}$ T cells are less sensitive to TGF-β suppression. In certain embodiments, lack of immune suppression of Cbl-$b^{-/-}$ $CD8^+$ T cells by $CD4^+$ $T_{reg}$ could also be a factor leading to the enhanced anti-tumor immune responses.

Tumor immunotherapy is a promising approach that can result in regression of bulky, invasive immunogenic cancer in some patients. Current available approaches remain less successful than desired. A major obstacle that has yet to be overcome is to develop an effective approach that may initiate, amplify, and maintain CTL responses against tumors that lack costimulatory signals. In certain aspects, the present invention provides that Cbl-$b^{-/-}$ mice effectively reject inoculated tumors in the absence of prior immunization. Adoptive transfer of Cbl-$b^{-/-}$ $CD8^+$ T cells eradicates established E.G7 tumors, demonstrating that Cbl-$b^{-/-}$ CTLs alone are sufficient to mediate an effective anti-tumor response. Cbl-$b^{-/-}$ $CD8^+$ T cells are also resistant to TGF-beta suppression, which indicates a much broader role of Cbl-$b^{-/-}$ T cells in the rejection of tumors, which can prevent T cell response through other mechanisms such as TGF-beta production. In certain aspects, the invention provides methods for modulation of the Cbl-b pathway in tumor-specific CTLs, wherein such modulation can be used to generate tumor-specific CTLs which can be used in cancer immunotherapy.

In certain aspects, the invention provides methods to determine the mechanisms by which Cbl-$b^{-/-}$ mice mount anti-tumor responses. In other aspects, the invention provides methods for using Cbl-b deficient CTLs, for example but not limited to Cbl-$b^{-/-}$ CTLs, as a therapeutic tool to treat established tumors. In certain embodiments, the efficiency of tumor-specific Cbl-$b^{-/-}$ $CD8^+$ T cells in tumor rejection can be quantitated by various methods known in the art. In certain aspects, the invention provides that Cbl-$b^{-/-}$ $CD8^+$ T cells eradicate metastatic tumor and tumors with suppressive environment such as TGF-beta, tumor barrier, and NKT cells. In other aspects, the invention provides that knock-down (kd) of Cbl-b function in tumor-infiltrating CTLs by siRNA, a dominant negative form of Cbl-b, or any other suitable agents, leads to reduction in size, and/or eradication of established tumors. In other aspects, the invention provides that adoptive transfer of Cbl-b kd CTLs leads to reduction in size, and/or eradication of established tumors. In other aspects, the invention provides that Cbl-b kd CTLs eradicate metastatic tumor and tumors with suppressive environment such as TGF-beta, tumor barrier, and NKT cells.

Methods for Making Cbl-$b^{-/-}$ $CD8^+$ T Cells $CD8^+$ T cells used in the adoptive transfer method of the present invention can be isolated from various sources. In certain embodiments, $CD8^+$ T cells can be isolated from tumor infiltrates which comprise CTLs. In other embodiments, $CD8^+$ T cells can be isolated from peripheral blood, and/or lymph organs. In other embodiments, the source of CD8+ T cells can be a clonal cell line which express specific TCRs for tumor antigen. In certain embodiments, the clonal cell line preferably have matching class I MHC molecules to class I MHC molecule of a subject in adoptive transfer method.

Methods and conditions for isolating, purifying, stimulation and expanding naïve, memory or effector CTLs are well known in the art, and are contemplated by the methods for making population of CD8+ T cells for use in the methods of the invention. In certain embodiments, clonal CD8+ T cells expressing a specific TCR can be generated by repeated rounds of stimulation of purified CD8+ T cells with dendritic cells pulsed with a mutated tumor antigen.

The type of tumor antigen referred to in the invention may be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of large, protein-based antigens include the following: Differentiation antigens such as MART-1/MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS. These protein-based antigens and their sequences are known and available to those of skill in the art in the literature or commercially. Additional antigens, which in certain embodiments can be recognized by autologous or transgenic TCRs expressed by a clonal CD8+ T cell lines, can be found in U.S. Publication 2006/0153858.

Attenuation of Cbl-b activity, for example attenuation of Cbl-b activity in tumor-specific CTL infiltrates, promotes anti-tumor response. The invention contemplates a variety of methods for attenuating and/or ablating Cbl-b activity in CD8+ T cells. In certain embodiments, Cbl-b activity is attenuated in a transient manner. In other embodiments, Cbl-b activity is attenuated continuously and/or permanently. In certain embodiments, Cbl-b activity can be reduced, or eliminated by introduction of any agent which is an antagonist to Cbl-b activity such as but not limited to interfering RNA (iRNA) molecule(s). In certain embodiments, Cbl-b activity can be attenuated and/or ablated by the use of polynucleotide compounds, such as but not limited to antisense polynucleotides, ribozymes, RNA interference molecules, triple helix polynucleotides and the like, where the nucleotide sequence of such compounds are related to the nucleotide sequences of DNA and/or RNA of Cbl-b gene. In certain aspects, Cbl-b levels, or activity are reduced to about 20%, 25%, 30%, 35%, 40%, 45%, 50%, 55%, 60%, 65%, 70%, 75%, 80%, 85%, 90%, 95%, 99% of Cbl-b levels or activity in cells which are not treated with a Cbl-b antagonist, for example siRNA which targets Cbl-b.

Antisense nucleotide technology has been the most commonly described approach in protocols to achieve gene-specific interference. For antisense strategies, stoichiometric amounts of single-stranded nucleic acid complementary to the messenger RNA for the gene of interest can be introduced into the cell. Triple helical nucleic acid structures are also useful for engineered interference. This approach relies on the rare ability of certain nucleic acid populations to adopt a triple-stranded structure. Under physiological conditions, nucleic acids are virtually all single- or double-stranded, and rarely if ever form triple-stranded structures.

In certain embodiments, an RNA interference (RNAi) molecule is used to decrease or inhibit expression of the nucleic acid against which the RNAi is directed. RNAi refers to the use of interfering RNA (iRNA) molecules for example but not limited to double-stranded RNA (dsRNA) or small interfering RNA (siRNA) to suppress the expression of a gene comprising a related nucleotide sequence. RNAi is also referred to as post-transcriptional gene silencing (or PTGS).

RNAi regulates gene expression via a ubiquitous mechanism by degradation of target mRNA in a sequence-specific manner. McManus et al., 2002, Nat Rev Genet 3:737-747. In mammalian cells, interfering RNA (RNAi) can be triggered by 21- to 23-nucleotide duplexes of siRNA. Lee et al., 2002, Nat Biotechnol 20: 500-505; Paul et al., 2002, Nat Biotechnol. 20:505-508; Miyagishi et al., 2002, Nat Biotechnol. 20:497-500; Paddison et al., 2002, Genes Dev. 16: 948-958. The expression of siRNA or short hairpin RNA (shRNA) driven by U6 promoter effectively mediates target mRNA degradation in mammalian cells. Synthetic siRNA duplexes and plasmid-derived siRNAs can inhibit HIV-1 infection and replication by specifically degrading HIV genomic RNA. McManus et al., J. Immunol. 169:5754-5760; Jacque et al., 2002, Nature 418:435-438; Novina et al., 2002, Nat Med 8:681-686. Also, siRNA targeting HCV genomic RNA inhibits HCV replication. Randall et al., 2003, Proc Natl Acad Sci USA 100:235-240; Wilson et al., 2003, Proc Natl Acad Sci USA 100: 2783-2788. Fas targeted by siRNA protects the liver from fulminant hepatitis and fibrosis. Song et al., 2003, Nat Med 9:347-351.

Double-stranded (ds) RNA can be used to interfere with gene expression in many organisms including, but not limited to mammals. dsRNA is used as inhibitory RNA or RNAi of the function of a nucleic acid molecule of the invention to produce a phenotype that is the same as that of a null mutant of a nucleic acid molecule of the invention (Wianny & Zernicka-Goetz, 2000, Nature Cell Biology 2: 70-75).

Many methods have been developed to make siRNA, e.g., chemical synthesis or in vitro transcription. Once made, the siRNA can be introduced directly into a cell to mediate RNA interference (Elbashir et al., 2001, Nature 411: 494-498; Song, E, et al. RNA interference targeting Fas protects mice from fulminant hepatitis. Nat. Med. 2003; 9: 347-351; and Lewis, D L, et al. Efficient delivery of siRNA for inhibition of gene expression in postnatal mice. Nat. Genet. 2002; 32: 107-108). Alternatively, the siRNA can be encapsulated into liposomes to facilitate delivery into a cell (Sorensen, D R, et al. Gene silencing by systemic delivery of synthetic siRNAs in adult mice. J Mol Biol. 2003; 327: 761-766). The siRNAs can also be introduced into cells via transient transfection.

A number of expression vectors have also been developed to continually express siRNAs in transiently and stably transfected mammalian cells (Brummelkamp et al., 2002, Science 296: 550-553; Sui et al., 2002, PNAS 99(6): 5515-5520; Paul et al., 2002, Nature Biotechnol. 20: 505-508). Some of these vectors have been engineered to express small hairpin RNAs (shRNAs), which get processed in vivo into siRNA-like molecules capable of carrying out gene-specific silencing. In certain embodiments, an shRNA contains plasmid under the control of a promoter, preferably a U6 promoter (Paul, C P, et al. Effective expression of small interfering RNA in human cells. Nat. Biotechnol. 2002; 20: 505-508). Another type of siRNA expression vector encodes the sense and antisense siRNA strands under control of separate pol III promoters (Miyagishi and Taira, 2002, Nature Biotechnol. 20: 497-500). The siRNA strands from this vector, like the shRNAs of the other vectors, have 3' thymidine termination signals. The shRNA gene can be delivered via a suitable vector system, e.g., adenovirus, adeno-associated virus (AAV), or retrovirus (Xia, H, et al. siRNA-mediated gene silencing in vitro and in vivo. Nat. Biotechnol. 2002; 20: 1006-1010; and Barton, G M, et al. Retroviral delivery of small interfering RNA into primary cells. Proc. Natl. Acad. Sci. USA 2002; 99: 14943-14945). In certain embodiments, the invention contemplates use of RNAi vectors which permit stable transfection, and continuous attenuation of Cbl-b activity in CD8$^+$ T cells.

In certain embodiments, the RNA may comprise one or more strands of polymerized ribonucleotide. It may include modifications to either the phosphate-sugar backbone or the nucleoside. For example, the phosphodiester linkages of natural RNA may be modified to include at least one of a nitrogen or sulfur heteroatom. Modifications in RNA structure may be tailored to allow specific genetic inhibition while avoiding a general panic response in some organisms which is generated by dsRNA. Likewise, bases may be modified to block the activity of adenosine deaminase. RNA may be produced enzymatically or by partial/total organic synthesis; any modified ribonucleotide can be introduced by in vitro enzymatic or organic synthesis.

The double-stranded structure may be formed by a single self-complementary RNA strand or two complementary RNA strands. RNA duplex formation may be initiated either inside or outside the cell. The RNA may be introduced in an amount which allows delivery of at least one copy per cell. Higher doses (e.g., at least 5, 10, 100, 500 or 1000 copies per cell) of double-stranded material may yield more effective inhibition; lower doses may also be useful for specific applications. Inhibition is sequence-specific in that nucleotide sequences corresponding to the duplex region of the RNA are targeted for genetic inhibition. The RNA molecule may be at least 10, 12, 15, 20, 21, 22, 23, 24, 25 or 30 nucleotides in length.

In certain embodiments, RNA containing a nucleotide sequences identical to a portion of Cbl-b gene are suitable for attenuation and/or inhibition Cbl-b activity. In certain embodiments, RNA sequences with insertions, deletions, and single point mutations relative to the target Cbl-b sequence can be effective for inhibition. Thus, one hundred percent sequence identity between the RNA and the target Cbl-b sequence is not required to attenuate and/or inhibit Cbl-b activity. Sequence identity of about 99%, 98%, 97%, 96%, 95%, 94%, 93%, 92% or 91% is contemplated by the methods of the present invention.

RNA may be synthesized either in vivo or in vitro. Endogenous RNA polymerase of the cell may mediate transcription in vivo, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNA strand (or strands). Inhibition may be targeted by specific transcription in an organ, tissue, or cell type; stimulation of an environmental condition (e.g., infection, stress, temperature, chemical inducers); and/or engineering transcription at a developmental stage or age. The RNA strands may or may not be polyadenylated; the RNA strands may or may not be capable of being translated into a polypeptide by a cell's translational apparatus. RNA may be chemically or enzymatically synthesized by manual or automated reactions. The RNA may be synthesized by a cellular RNA polymerase or a bacteriophage RNA polymerase (e.g., T3, T7, SP6). Any suitable method for use and production of an expression construct that are known in the art is contemplated by the present invention as a method to attenuate and/or reduce Cbl-b activity.

In other embodiments, Cbl-b activity can be attenuated and/or eliminated by targeted gene knock out by mutations, including but not limited to exon deletions, in the genomic copy of Cbl-b. Methods for targeted gene knock-out are well known in the art and are contemplated by the present invention.

In certain embodiments, Cbl-b gene disruption can be induced by site-specific DNA double strand breaks (DSB) which can be created in the genomic sequence of Cbl-b. Site specific nucleases can be engineered as fusion proteins which carry a DNA binding domain, which recognizes a specific nucleic acid sequence in the Cbl-b gene, fused to a nuclease domain. Such site specific nucleases can create DSB at predetermined, specific nucleotide sequences. Repair of such DSB by endogenous DNA repair pathways generally results in an error, deletion or substitution of nucleotides, thus effectively leading to disruption of the target gene Cbl-b.

In other embodiment, Cbl-b activity can be attenuated and/or reduced by any agent which targets Cbl-b protein activity, including but not limited to Cbl-b Ub-ligase activity.

In other aspects, the invention provides a method for making Cbl-b−/− deficient CD8$^+$ T cells by ablation of Cbl-b in tumor-specific CTL infiltrates. Tumor tissues often contain large numbers of infiltrating leukocytes that are enriched for tumor-specific CTLs. These cells usually cannot respond to the tumors. The invention provides methods, which demonstrate that inactivation of Cbl-b in tumor-specific CTL infiltrates restore their responsiveness to tumors, because Cbl-b$^{-/-}$ T cells respond to weak antigen stimulation and do not depend on costimulation for activation. In certain embodiments, the methods can use siRNA or dominant negative form of Cbl-b to determine whether inhibition of Cbl-b function in tumor-infiltrating CTLs renders these CTLs the characters of Cbl-b$^{-/-}$ T cells. In other embodiments, the invention provides methods to determine whether Cbl-b-ablated tumor-specific CTL infiltrates efficiently eradicate the established tumors.

In certain aspects, the invention is directed to methods for making "super killer" CTLs that can be fully activated and exert effector function independent of the costimulation.

This method comprises down-regulating the activity of Cbl-b in CD8$^+$ T cells. In other aspects, the invention is directed to methods for using these "super killers" to elicit immune response against tumors. In certain embodiments, the invention is directed to methods for using these "super killers" in cancer immunotherapy. These methods allow direct activation of tumor-specific CTLs by tumor cells that are characterized with either strong or weak antigenicity, and do not express costimulatory ligands.

In other aspects, the methods for making CD8$^+$ T cells which do not require co-stimulation, also referred to as "super killer" CTLs, wherein CTLs can be isolated from tumor specific infiltrates. Tumor infiltrates are enriched for CTLs against tumor antigens, and immunotherapy using these CTLs could restrict the cytotoxicity to tumor cells without eliciting a broad autoimmunity. At present, a major challenge along this direction is the identification of molecular pathways that control costimulatory signals. Modulation of these pathways should be a powerful mean to uncouple the requirement of costimulation from TCR-induced T-cell activation, consequently allowing priming and effector function of tumor-specific CTLs independent of costimulation signals. Cytotoxicity of CTLs requires activation of CTLs. However, data provided herein indicate that transfer of non-activated Cbl-b–/– CTLs can also reject tumors, for example E.G7 tumor. These results show that ablation of Cbl-b enhances T cell activation.

Methods for Screening for Agents which Inhibit Cbl-b Activity

In certain aspects, the invention provides screening methods to identify agents, including but not limited to chemical compounds, which can attenuate and/or inhibit Cbl-b activity, including but not limited to Cbl-b Ub-ligase activity. In one embodiment, the screening method can use an assay to measure Cbl-b Ub-ligase activity to determine whether an agent affects Cbl-b activity. In other embodiments, the methods can use an assay to measure CD28-independent activation of CTLs, impaired TCR down-modulation induced by anti-TCR stimulation, or loss of TGF-beta suppression of CTL proliferation, or any combination thereof. Any one of these assays can be used to determine whether an agent modulate or impair Cbl-b function.

In certain embodiments, a method for identifying an agent which affects Cbl-b expression or activity comprises: stimulating a cell with an anti-CD3 antibody in the absence of co-stimulation with anti-CD28 antibody, contacting the cell with a candidate agent, measuring levels of cell stimulation or proliferation, wherein an agent which leads to cell stimulation or proliferation is indicative of an agent which down-regulates Cbl-b activity or expression. Non-limiting examples for suitable cells that can be used in the methods to identify an agent, which affect Cbl-b expression or activity, are CD4$^+$T AND CD8$^+$T CELLS. Assays for measuring T cell stimulation and proliferation are know in the art, and include but are not limited to assays that measured level of cytokine expression, for example but not limited to IL-2, INF-γ, and IL-10.

In certain embodiments, the invention provides methods for identifying an agent that affects Cbl-b activity, comprising: contacting a source of Cbl-b with an agent, determining whether the agent decreases Cbl-b activity. Assays that can be used to measure down-regulation of Cbl-b activity include, but are not limited to, determining levels of TCR-induced T cell proliferation, p85-ubiquitination, antigen-induced TCR-downmodulation, and TGF-beta suppression of cell proliferation, wherein an agent which enhances T cell proliferation in the presence or absence of TGF-beta, or decreases antigen-induced TCR downmodulation (Naramura, M, et al., 2004), or decreases ubiquitination of p85 (Fang, D., et al., 2001) is indicative of an agent which decreases Cbl-b activity. In certain embodiments, the methods for identifying an agent that affects Cbl-b activity can also comprise a step of determining whether the agent binds to Cbl-b.

In certain aspects, the invention provides that Cbl-b$^{-/-}$ T cells play an essential role in tumor rejection. In certain aspects, the invention provides that Cbl-b$^{-/-}$ mice, are resistant to tumor inoculation. In certain embodiments depletion or reduction of the number of T cells in Cbl-b$^{-/-}$ mice permits vigorous growth of the inoculated tumors. In other aspects, the invention provides that there are massive CD8$^+$ T infiltrates in tumor tissues of Cbl-b$^{-/-}$ mice. In other aspects, the invention provides that CD8$^+$ T cells from Cbl-b$^{-/-}$ mice are resistant to TGF-beta suppression and produce high levels of IL-2 and IFN-gamma upon TCR triggering even in the absence of CD28 costimulation. In other aspects, the invention provides that adoptive transfer of isolated or purified CD8$^+$ T cells into tumor-bearing mice is sufficient to eradicate the established E.G7 tumors. In other aspects, the invention provides that Cbl-b$^{-/-}$ CD8$^+$ T cells respond to tumor antigen stimulation and exert cytotoxic activity against tumor cells independent of costimulatory signals. Tumor-specific CTLs can be identified, isolated, and/or enriched from tumor tissues by any suitable method known in the art, for example by Fluorescent cell sorting, or by magnetic beads. Such procedures typically yield a population of cells which comprises at least about 85% to 89%, 90% to 95% of CTLs. Further enrichment by successive rounds of purification can yield a population of cells which comprises at least about 95%-99% of CTLs. In certain aspects, the invention provides a population of cells comprising about 10%, 15%, 20%, 25%, 30%, 35%, 40%, 45%, 50%, 55%, 60%, 65%, 70%, 75%, 80%, 85%, 90%, 95%, 99% of CTLs. In certain aspects, the invention provides methods for modulation of Cbl-b pathway in CD8$^+$T-cells, wherein in certain embodiments the CD8$^+$T-cells can be isolated from tumor infiltrates. The methods of the present invention can be used to generate "super killer" CTLs that can be used in cancer immunotherapy.

Examples and Hypothetical Examples

Mice and Cells. Cbl-b knockout (Cbl-b$^{-/-}$) and ATM knockout (ATM$^{-/-}$) mice were generated as previous described (Chiang, et al., 2000; Barlow, et al., 1996). Cbl-b$^{-/-}$ mice were backcrossed to C57BL/6 mice for 12 generations. C57BL/6, Cbl-b$^{-/-}$, ATM$^{-/-}$, Cbl-b$^{-/-}$ ATM$^{-/-}$ double knockout mice were maintained in specific pathogen-free condition in accordance with the guideline and protocols for animal care. EL4 (ATCC, Rockville, Md.) and E.G7 cells were maintained in RPMI 1640 supplemented with 10% fetal bovine serum, 100 units/ml penicillin, 100 µg/ml streptomycin, glutamine, and 2-mercaptoethanol.

In vitro T cell proliferation and Cytokine production assays. Total T cells or CD8$^+$ T cells were purified from spleen by MACS using a T cell or CD8$^+$ T cell enrichment kit (Miltenyi Biotech). For T-cell proliferation assay, purified CD8$^+$ T cells were stimulated with various concentrations of plate-bound anti-CD3ε and soluble anti-CD28 (5 µg/ml) for 72 hr. After pulsing cells with [$^3$H]-thymidine (1 µCi/ml) for the 12 hr, cells were harvested and [$^3$H]-thymidine uptake was determined using a β-counter. For intracellular IL-2 and IFN-γ staining, cells were stimulated for 12 hr with anti-CD3 or anti-CD3+anti-CD28 antibodies. After further incubation with Brefeldin A (5 μg/ml) for 6 hours, stimulated cells were surface-stained with anti-CD8 antibody, fixed and permeabilized in Cytofix/Cytoperm solution (BD PharMingen), and then stained intracellularly with anti-IL-2 and anti-IFN-γ antibodies. Stained cells were analyzed on an LSR II (BD Bioscience) using Flowjo software (TreeStar, Inc). Purified or fluorochrome-conjugated anti-CD3, anti-CD28, anti-CD4, anti-CD8, anti-IL-2, anti-IFN-γ, anti-TCRβ, anti-CD44, and anti-CD62L antibodies were from BD PharMingen. ELISA analysis of IL-2 production was performed according to a previous protocol (Chiang, et al., 2000).

Immuno-histochemistry and analyses of tumor-infiltrating lymphocytes. Seven and 19 days after tumor inoculation, tumor tissues were collected, frozen in Tissue-Tek OCT medium (Sakura Finetech), and cryosectioned. Sections were stained with either haematoxylin and eosin (H/E) or FITC-anti-CD8 antibody. Staining results were recorded by normal or fluorescence microscopy. To analyze tumor-infiltrates by flow cytometry, tumor-infiltrating lymphocytes were prepared from tumor tissues 14 days after inoculation. Tumor was excised from sacrificed mice, washed in PBS, and cut into pieces of 2-3 mm in size. The resulting tumor pieces were then digested at 37° C. with collagenase D (1.5 mg/ml, Sigma) in DMEM supplemented with 2% fetal bovine serum and 50 units/ml DNase I (Sigma). After digestion for 40 min, cells were passed through a 70 μm strainer and flow-through cell suspension was washed with PBS, stained with different combination of antibodies, and analyzed on an LSR II. Antibodies used for staining were anti-TCRβ, anti-CD8, anti-CD44, and anti-CD62L (BD PharMingen).

In vivo experiments. Tumor cells in log-phase growth were washed three times with and resuspended in PBS. After shaving the right flank, subcutaneous injection with indicated numbers of cells in 100 μl PBS was performed. Tumor growth was monitored weekly or twice a week using a caliper. For adoptive transfer, at day 7 after establishing tumor on C57BL/6 mice, mice were injected with $3 \times 10^6$ purified CD8$^+$ T cells isolated from lymph node cells of wildtype and Cbl-b$^{-/-}$ mice using a CD8$^+$ T cells enrichment kit (Miltenyi Biotech). Tumor growth was then monitored every three days using a caliper. Tumor growth in Cbl-b$^{-/-}$ ATM$^{-/-}$ mice was measured weekly. Tumor volumes were approximated by multiplying the measured length by the measured width by the calculated mean of the measured length and width values, as described previously (Helmich, B. K., and R. W. Dutton. 2001. The role of adoptively transferred CD8 T cells and host cells in the control of the growth of the EG7 thymoma: factors that determine the relative effectiveness and homing properties of Tc1 and Tc2 effectors. *J Immunol* 166:6500-6508).

Cytokine secretion and/or proliferation of purified CD8$^+$ T cells: Cytokine secretion and/or proliferation of purified CD8$^+$ T cells from wild-type and Cbl-b$^{-/-}$ mice was compared after stimulation through the TCR alone or costimulation through the TCR and costimulatory receptor CD28. Wild-type CD8$^+$ T cells generated limited IL-2 and IFN-γ responses after stimulation with anti-CD3 antibody alone (FIG. 1a). Wild-type CD8$^+$ T cells produced approximately 6 times more IL-2 and 2-3 times more IFN-γ when CD28 costimulation was provided. Stimulation of Cbl-b$^{-/-}$ CD8$^+$ T cells with anti-CD3 antibody alone elicited much higher levels of IL-2 and IFN-γ even when compared to the responses of wild-type cells costimulated by anti-CD3 and CD28 antibodies. Addition of costimulatory signaling by anti-CD28 antibody also slightly enhanced the IL-2 production by Cbl-b$^{-/-}$ CD8$^+$ T cells; however, the level of IFN-γ was not augmented (FIG. 1a).

Figure 1B:
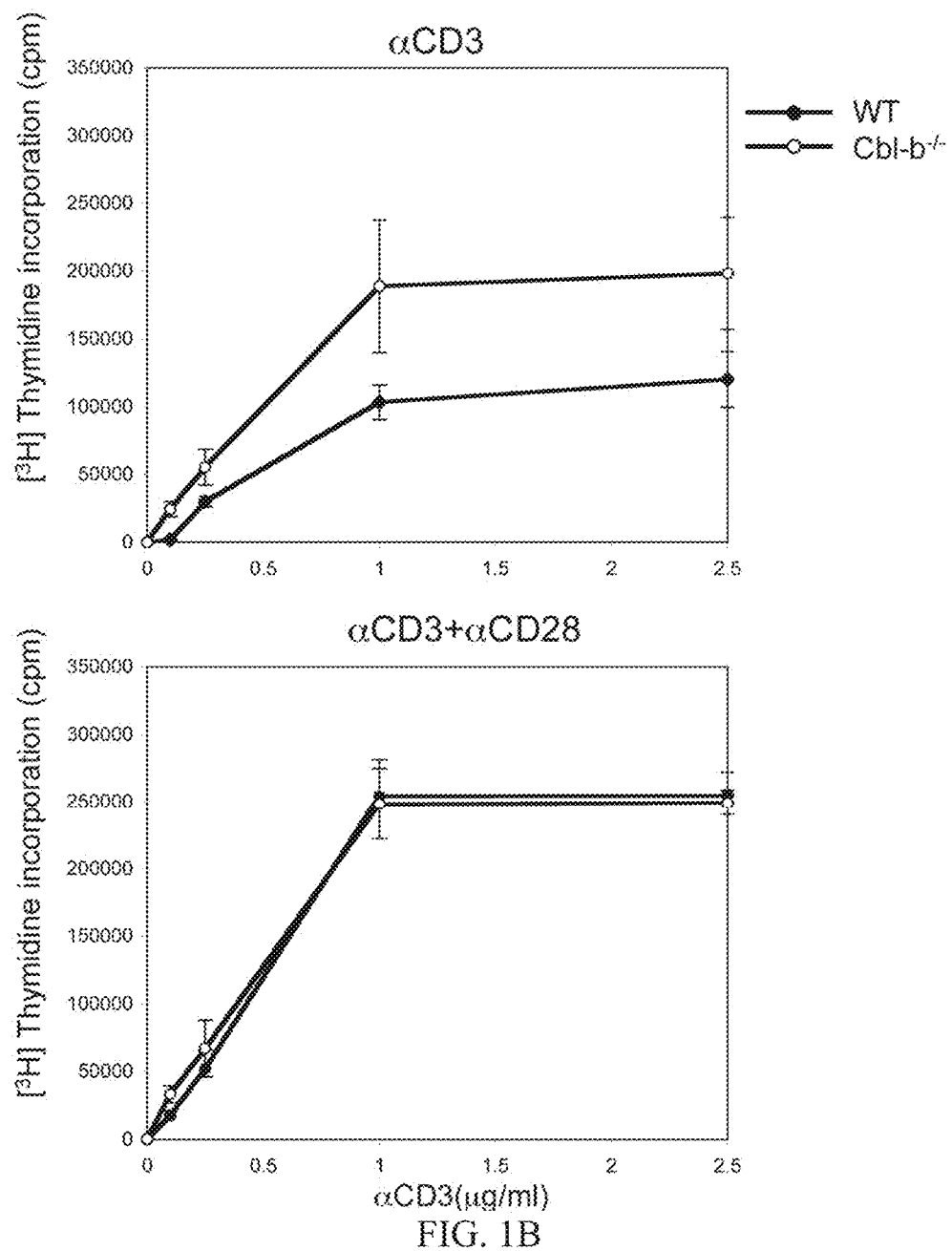
Figure 1C:
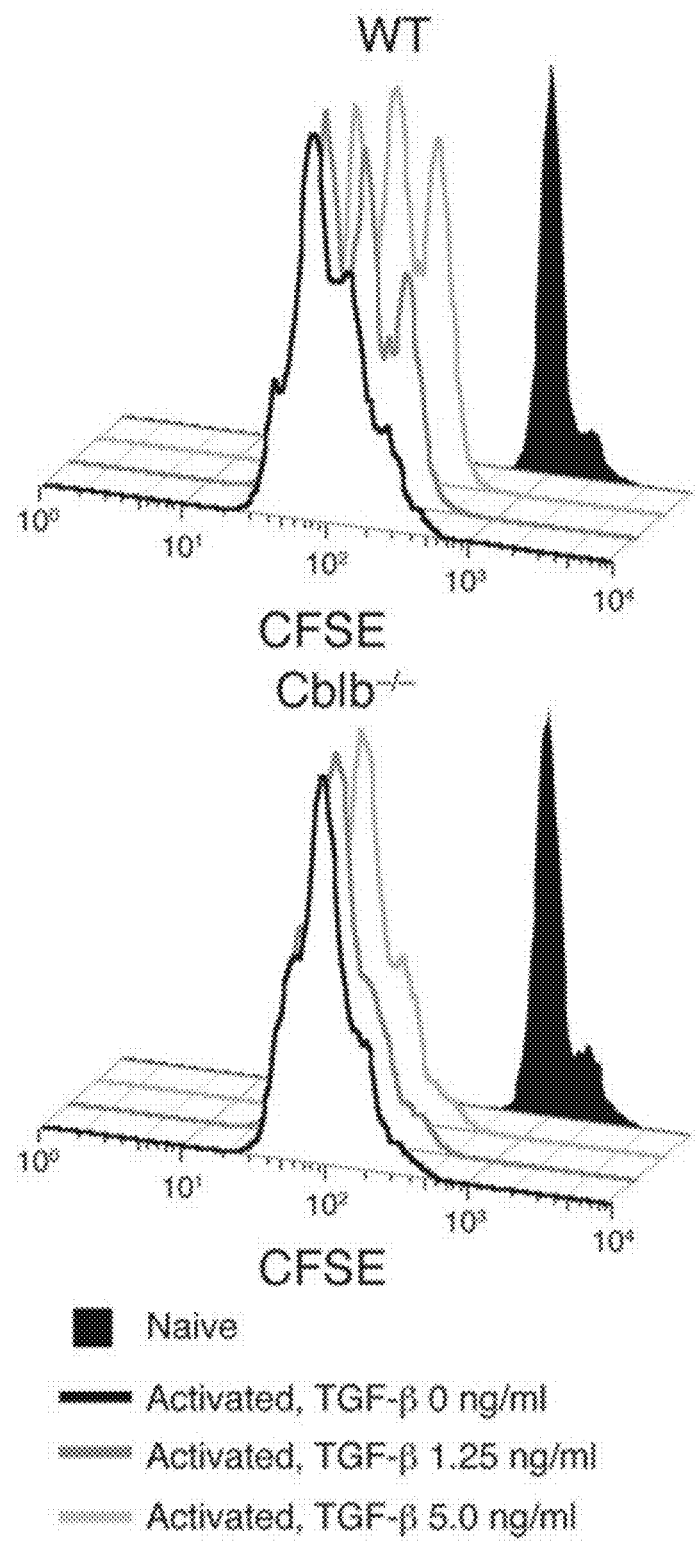
Figure 1D:
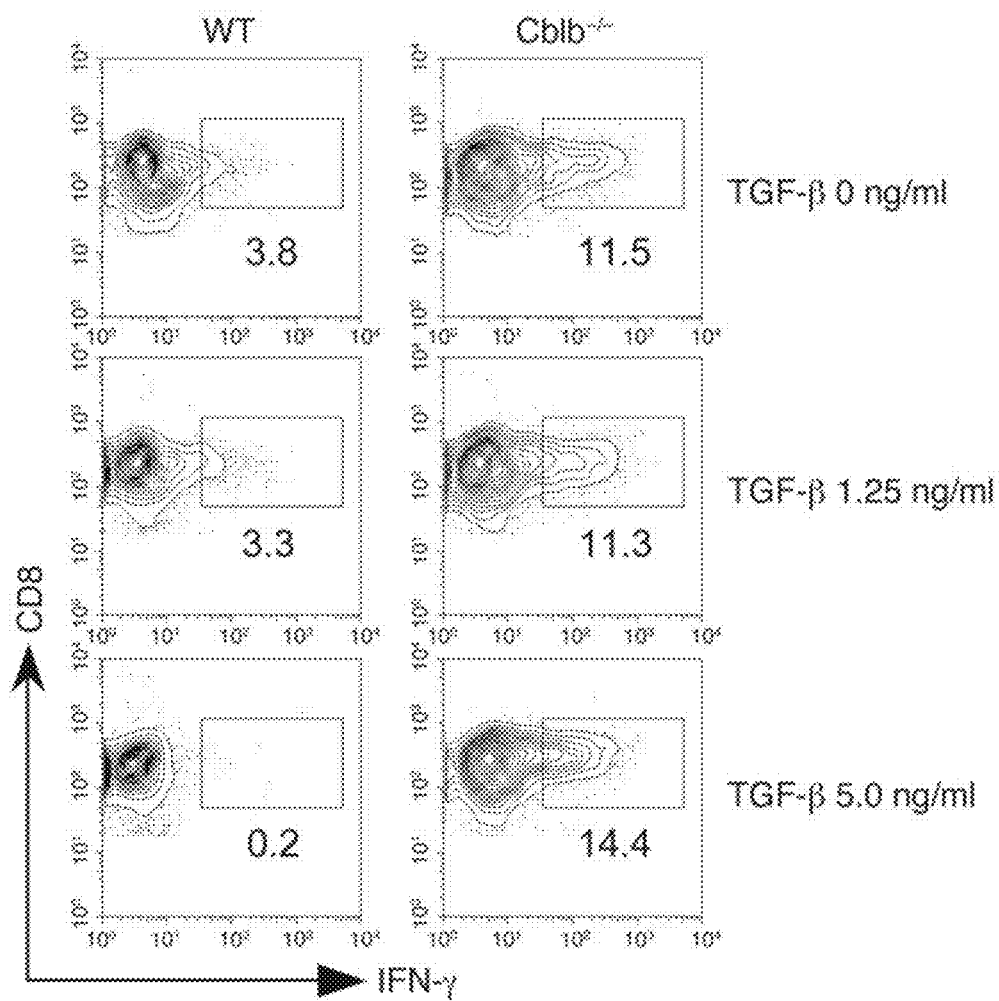
Figure 5:
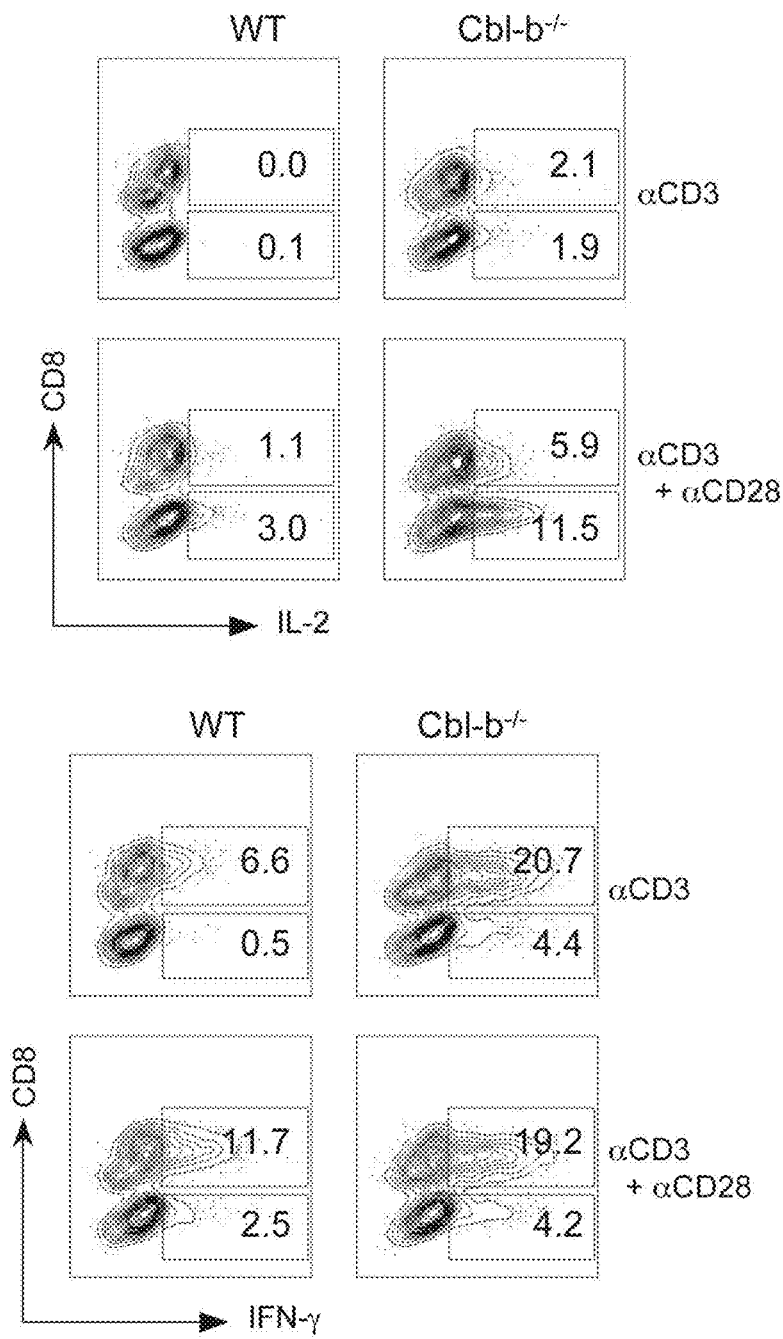
FIG. 5 shows IL-2 and IFN-γ production of Cbl-b$^{-/-}$ CD8$^+$ T cells in the presence of CD4$^+$ T cells. Total T cells from wildtype (WT) or Cbl-b$^{-/-}$ mice were stimulated with plate-bound anti-CD3 antibody alone or anti-CD3 plus soluble anti-CD28 antibodies. IL-2 and INF-γ production was determined by intracellular staining and analyzed by flow-cytometry. Percentages of IL-2 and INF-γ-producing cells are indicated in the plots. The results show that IL-2 and INF-γ production by Cbl-b$^{-/-}$ CD8$^+$ T cells were significantly higher than that by WT CD8$^+$ T cells after anti-CD3 antibody stimulation even in the presence of CD4$^+$ T cells.
Figure 6A:
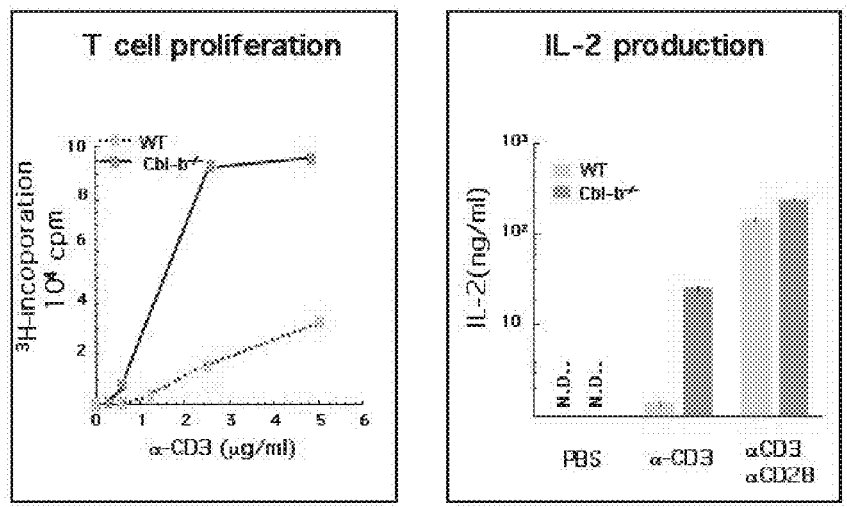
FIGS. 6A-6B show activation of Cbl-b$^{-/-}$ T cells abolishes the dependence on CD28-costimulation.
Figure 6B:
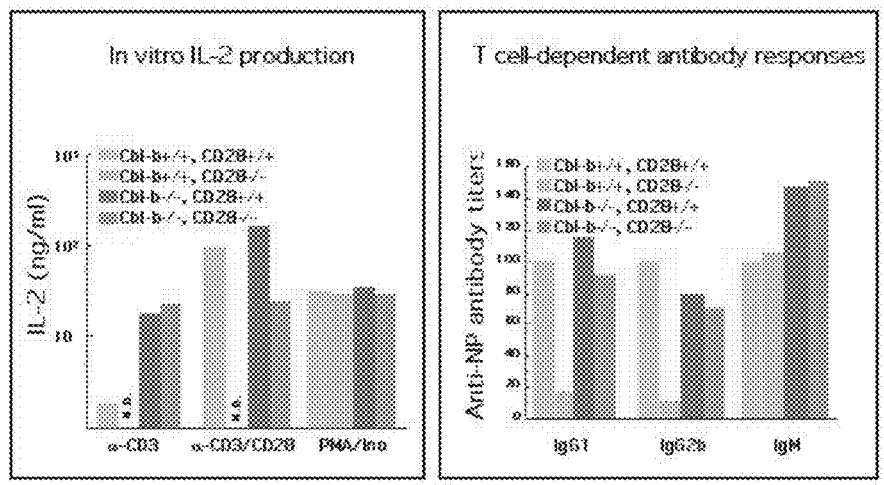
Figure 7A:
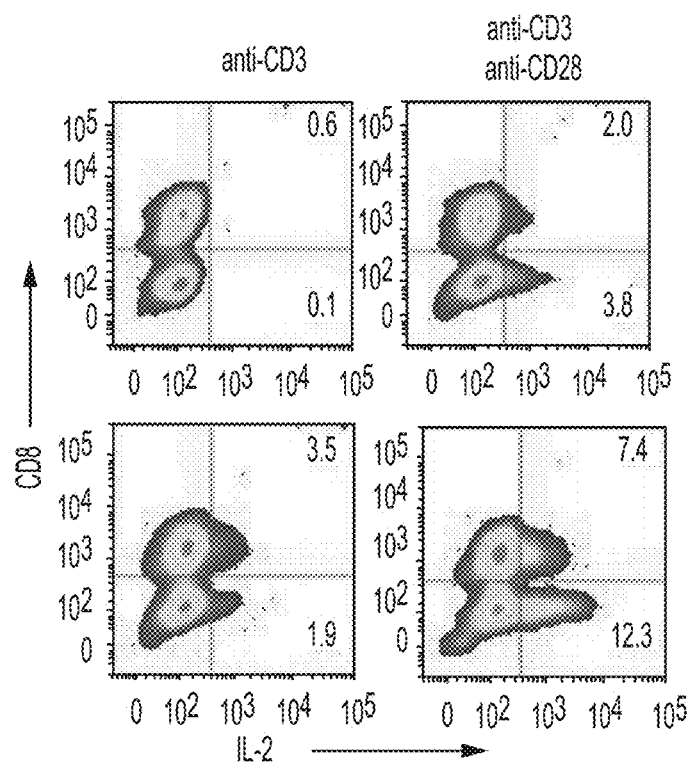
FIGS. 7A-7B show CD28-independent activation of Cbl-b$^{-/-}$ CD8$^+$ T cells. Lymph node T cells from C57BL/6 (B6) or Cbl-b$^{-/-}$ mice were purified by MACS, stimulated with either plate-bound anti-CD3 antibody (5 μg/ml) alone or in combination with soluble anti-CD28 antibodies (2 μg/ml). 20 hours later, 10 μg/ml brefeldin A was added into the culture to block cytokine secretion. Cells were cultured for additional 3 hours. After permeabilization, cells were stained with anti-CD8 (PE) and anti-IL-2 (FITC) (FIG. 7a) or anti-γ (FITC) (FIG. 7b) antibodies and then analyzed on a LSR II. Percentages of IL-2 and -γ positive cells CD8$^+$ or CD8$^-$ populations are indicated. Results are representatives of at least three independent experiments.
Figure 7B:
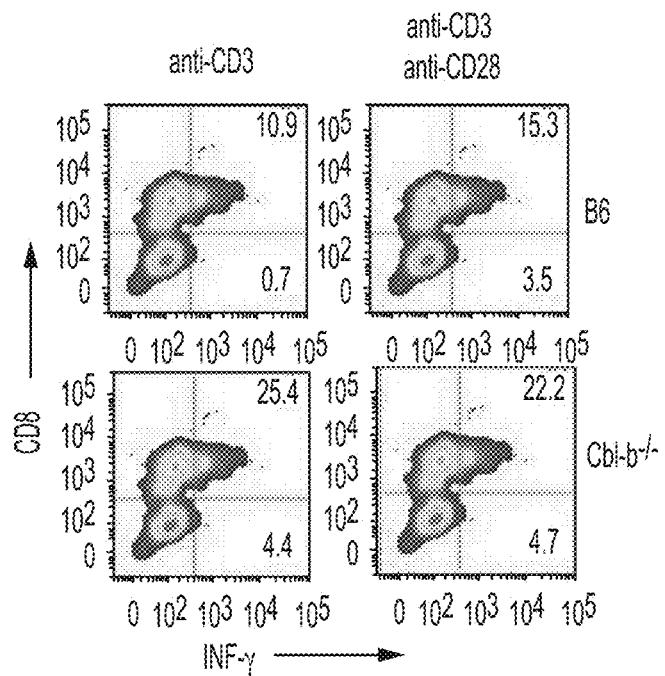
Figure 8A:
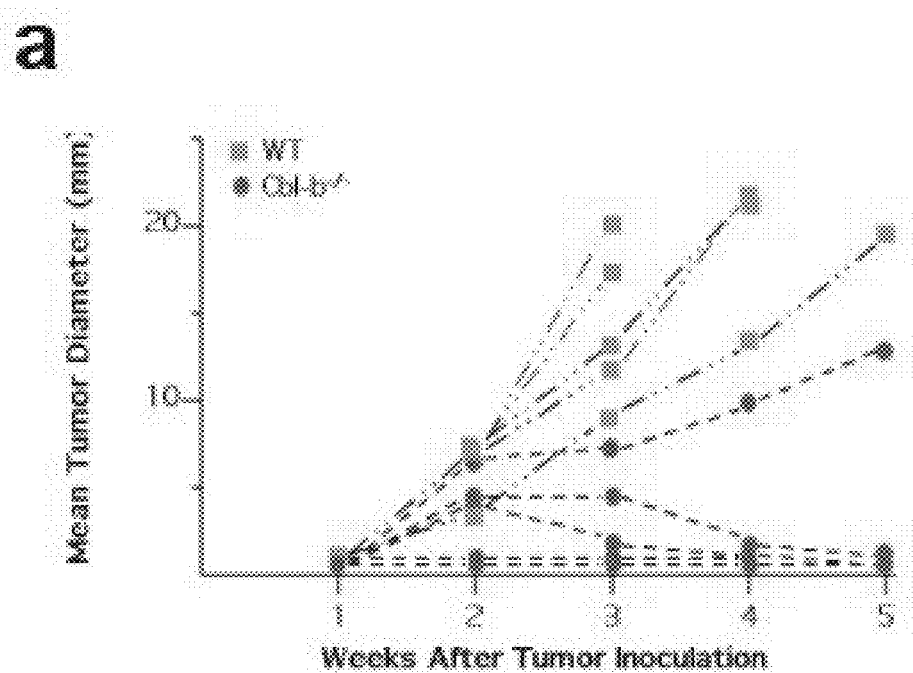
FIGS. 8A-8D show resistance of Cbl-b$^{-/-}$ mice to implanted E.G7, EL4 or B16 tumors.
Figure 8B:
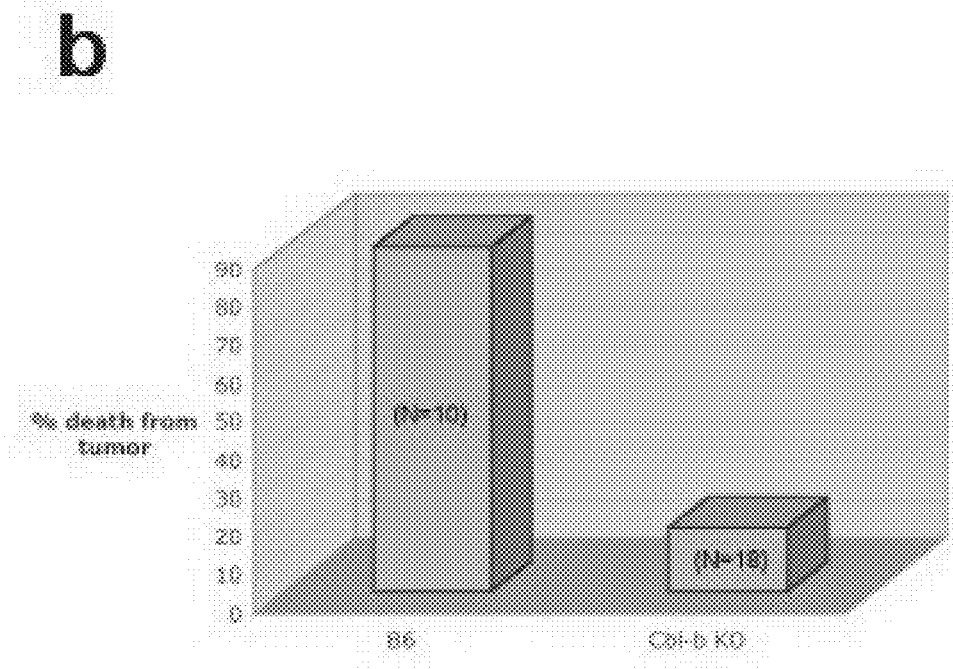
Figure 8C:
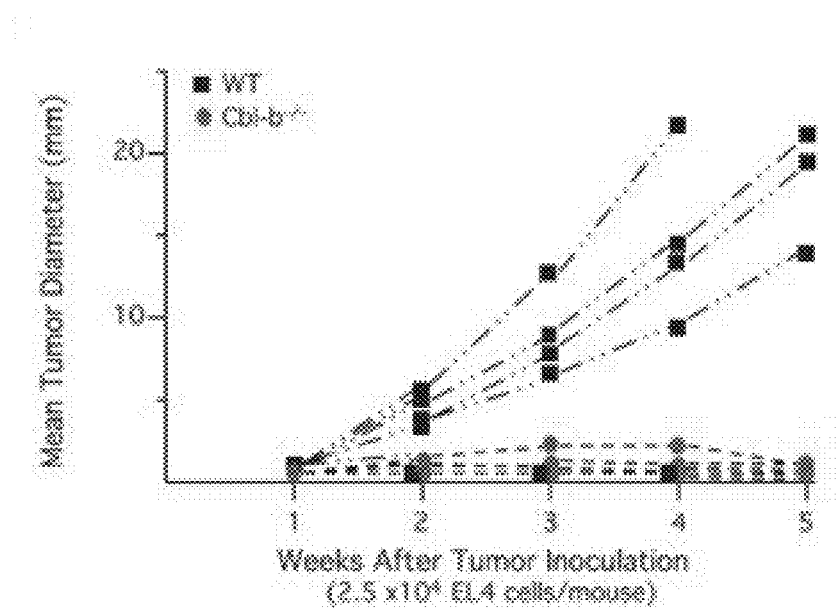
Figure 8D:
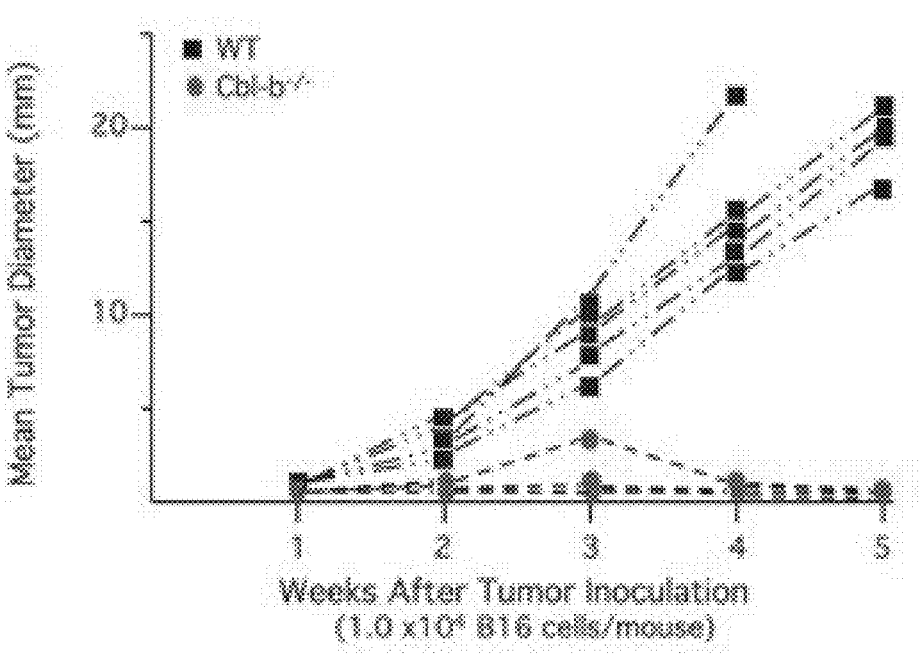
Figure 9A:
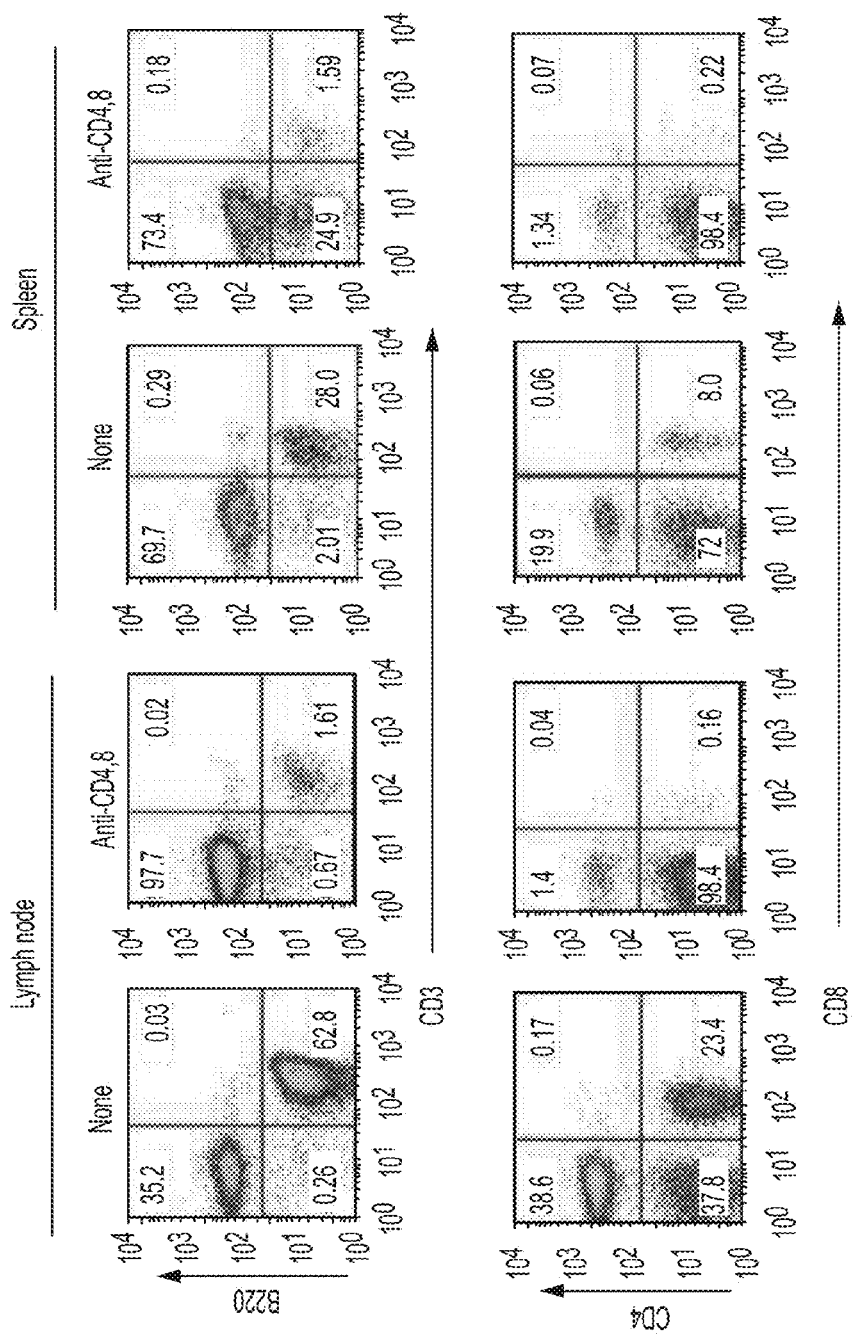
FIGS. 9A-9B show T cell-depleted Cbl-b$^{-/-}$ mice are susceptible to inoculated E.G7 tumors.
Figure 9B:
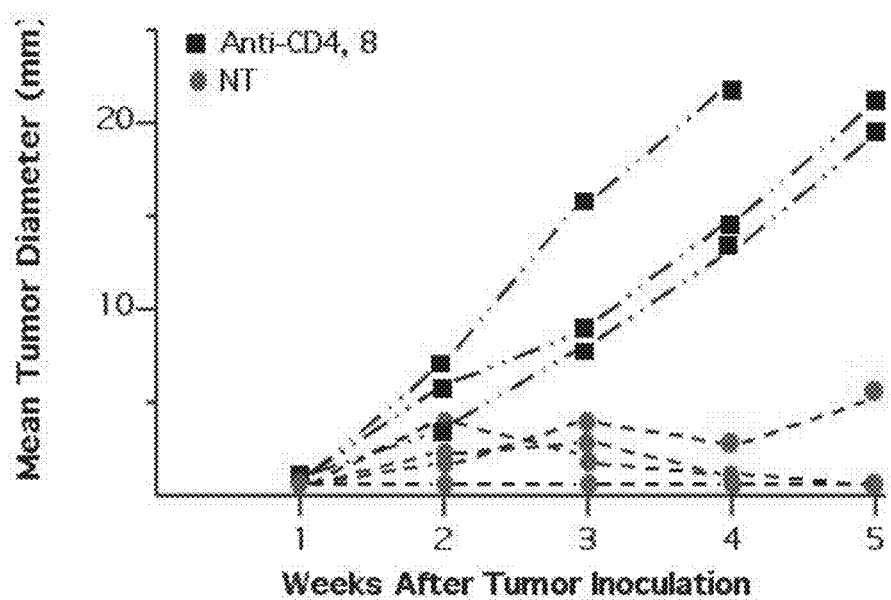
Figure 10A:
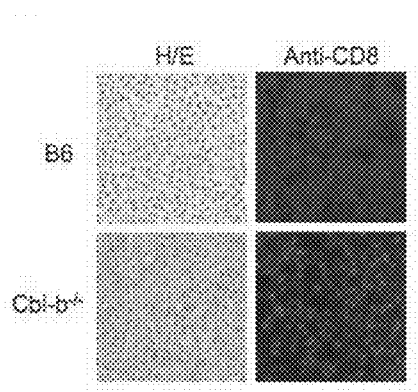
FIGS. 10A-10B show infiltration of CD8$^+$ cells in E.G7 tumor tissue. $1 \times 10^6$ E.G7 cells were inoculated subcutaneously into the flanks of Cbl-b$^{-/-}$ and wildtype mice.
Figure 10B:
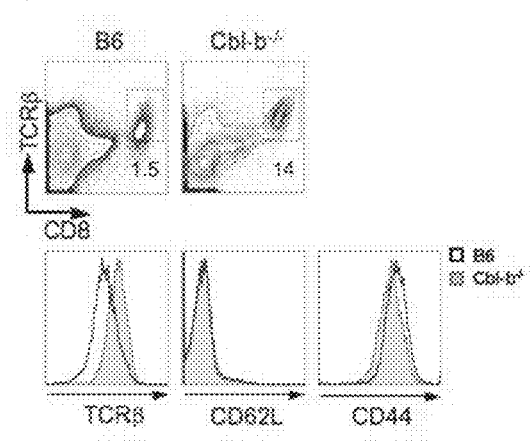
Figure 11:
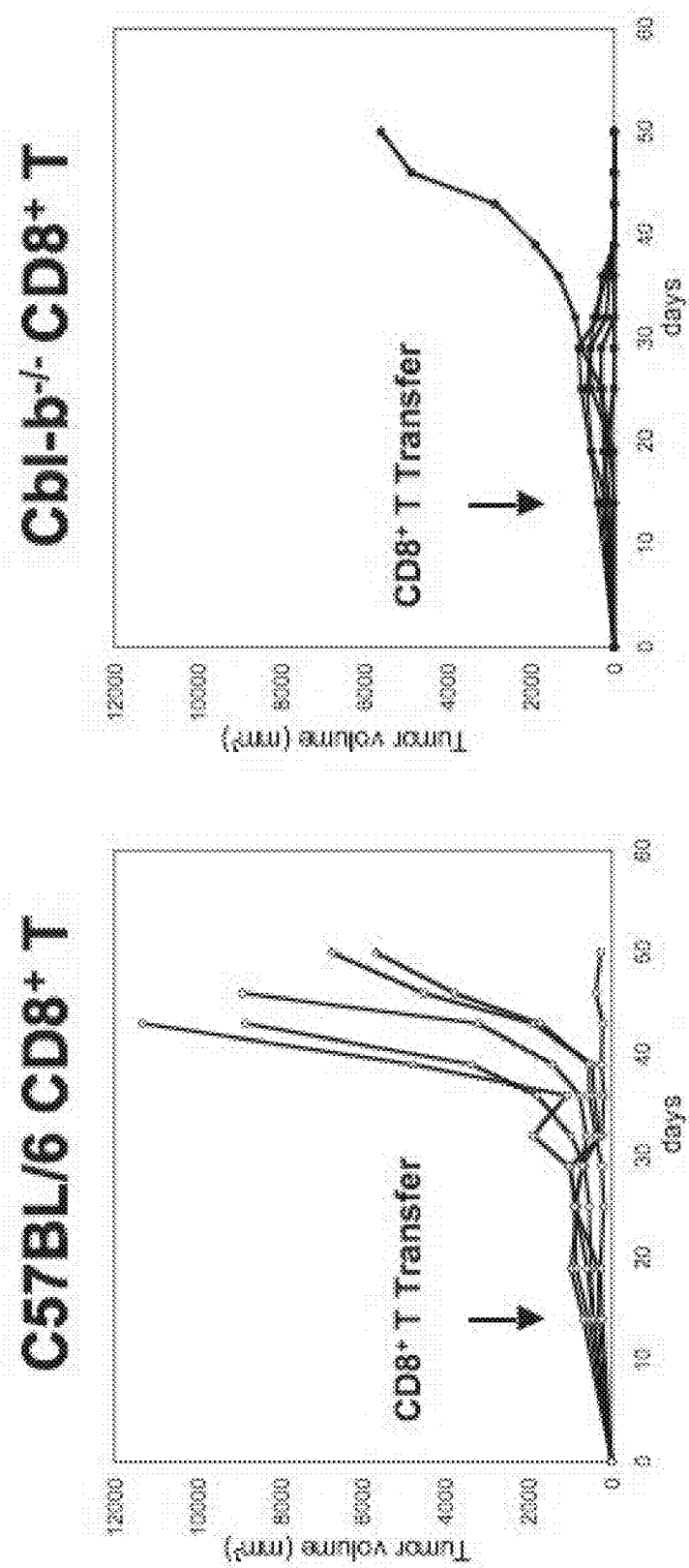
FIG. 11 shows rejection of the established E.G7 tumors by adoptively transferred Cbl-b$^{-/-}$ CD8$^+$ T cells. To generate E.G7 tumor-bearing mice, C57BL/6 mice (8-10 week-old) were inoculated subcutaneously with $10^6$ E.G7 cells, which produced subcutaneous tumors that were approximately $5 \times 5 \times 5$ mm$^3$ in volume in two weeks. Two weeks after the inoculation, $3 \times 10^6$ purified CD8$^+$ T cells from either wildtype C57BL/6 or Cbl-b$^{-/-}$ mice by i.v. injection were transferred. CD8$^+$ T cells were purified by MACS and were more then 95% pure. In the following weeks, tumor sizes were monitored with a microcaliper and documented as volume (mm$^3$). Shown are the statistics of the sizes of tumors from tumor-bearing mice that received wildtype (left) or Cbl-b$^{-/-}$ (right) CD8$^+$ T cells.
Figure 12A:
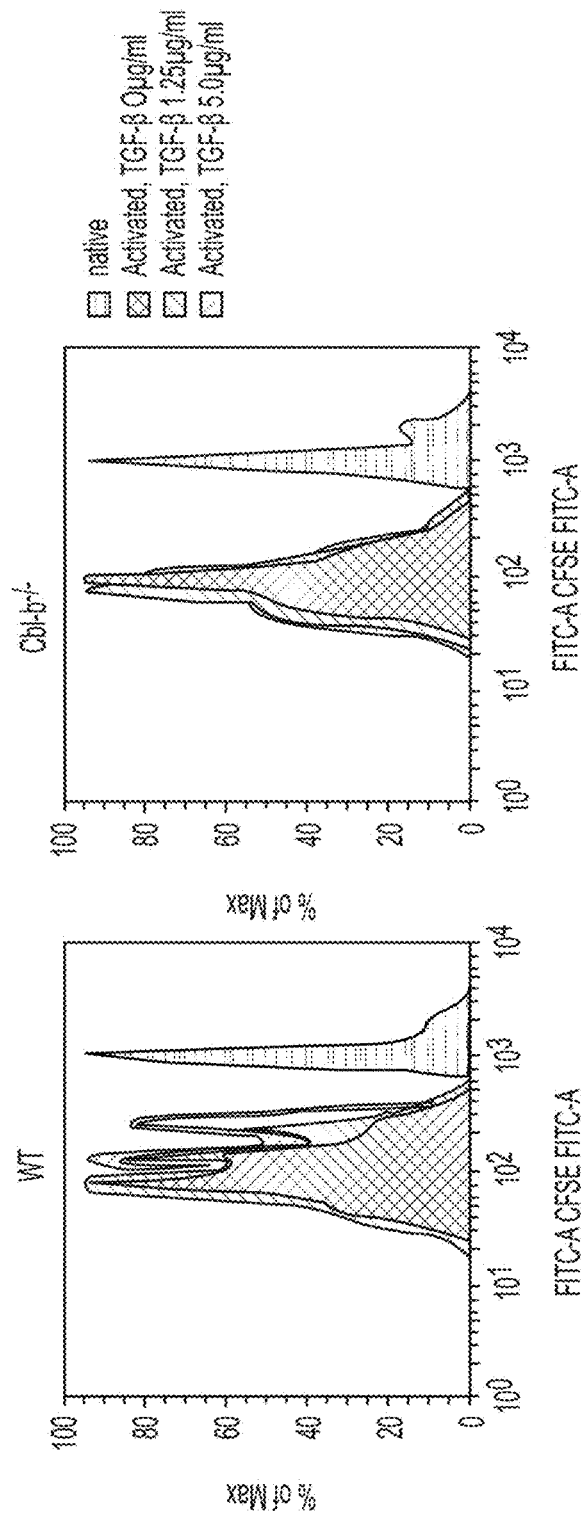
FIGS. 12A-12C show Cbl-b$^{-/-}$ CD8$^+$ T cells are resistant to TGF-beta suppression. CD8$^+$ T cells were purified from the lymph nodes of wildtype and Cbl-b$^{-/-}$ mice by MACS using a CD8 cell enrichment protocol according to manufacture's instruction (Miltenyi Biotec). To examine cell proliferation, cells were first labeled with CFSE according to manufacture's instruction (Molecular Probe). Labeled cells were stimulated with plate-bound anti-CD3 (5 μg/ml) and soluble anti-CD28 (2 μg/ml) in the absence or presence of different concentrations of TGF-beta. After 3 days of culture, cells were harvested, stained with anti-CD8 (PE) antibody, and then analyzed on a LSR II. Intracellular staining of IFN-gamma was performed as described herein.
Figure 12B:
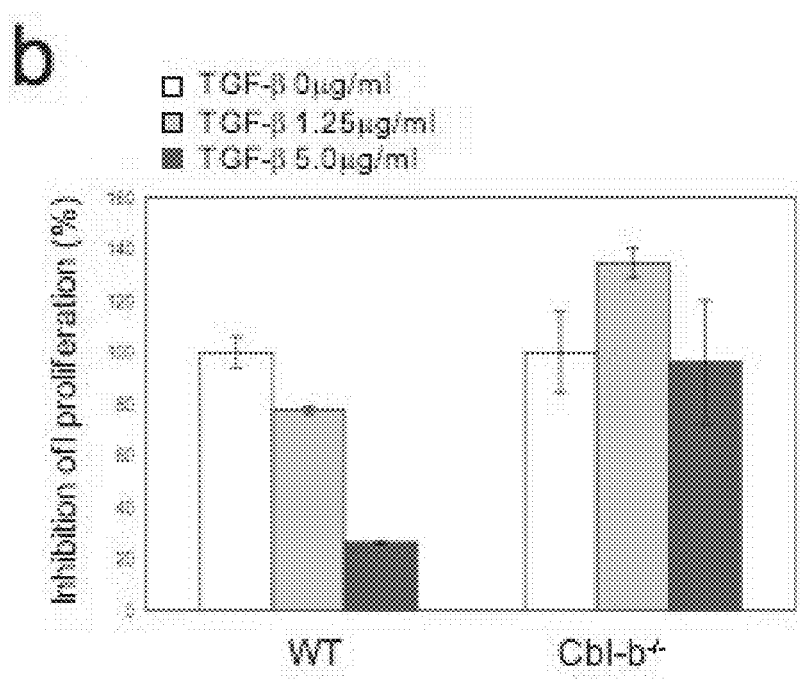
Figure 12C:
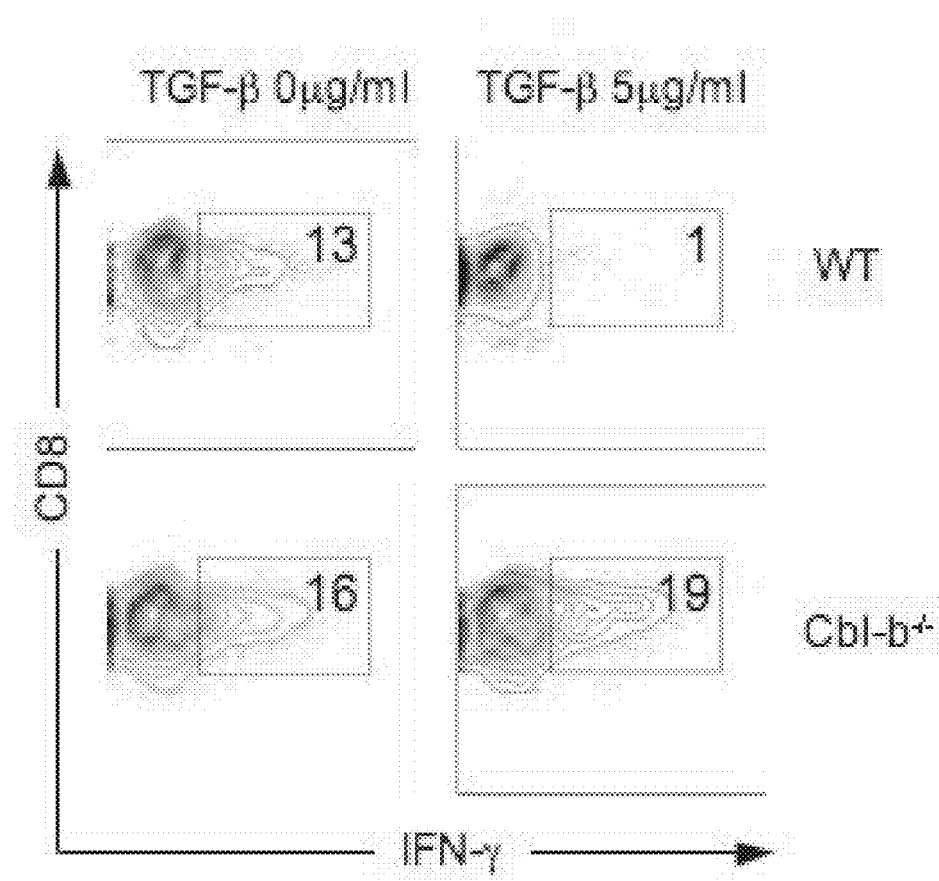
Figure 13A:
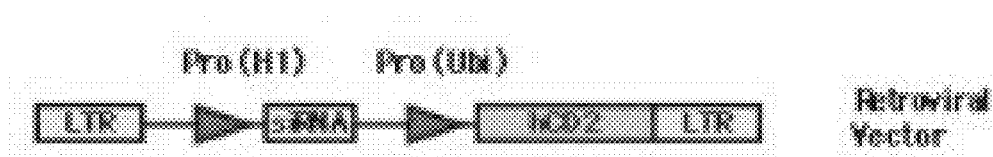
FIGS. 13A-13C show knockdown Cbl-b expression by siRNA and retroviral infection of cultured primary T cells.
Figure 13B:
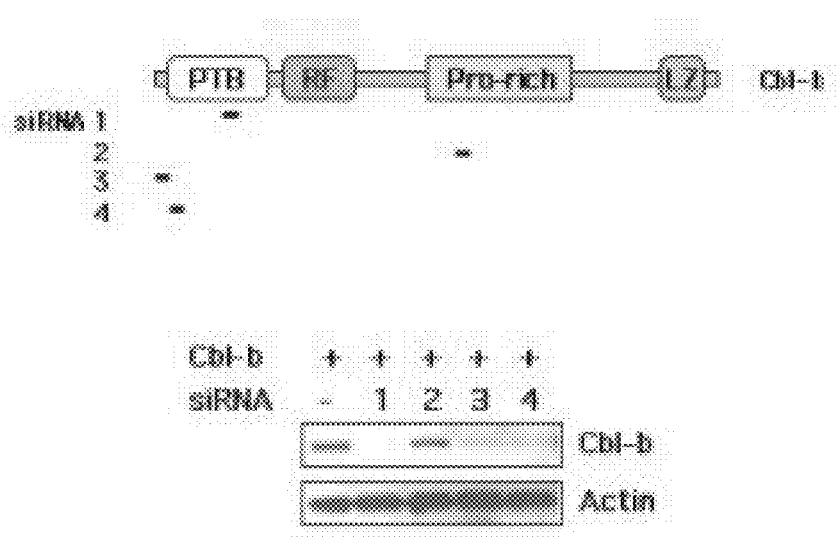
Figure 13C:
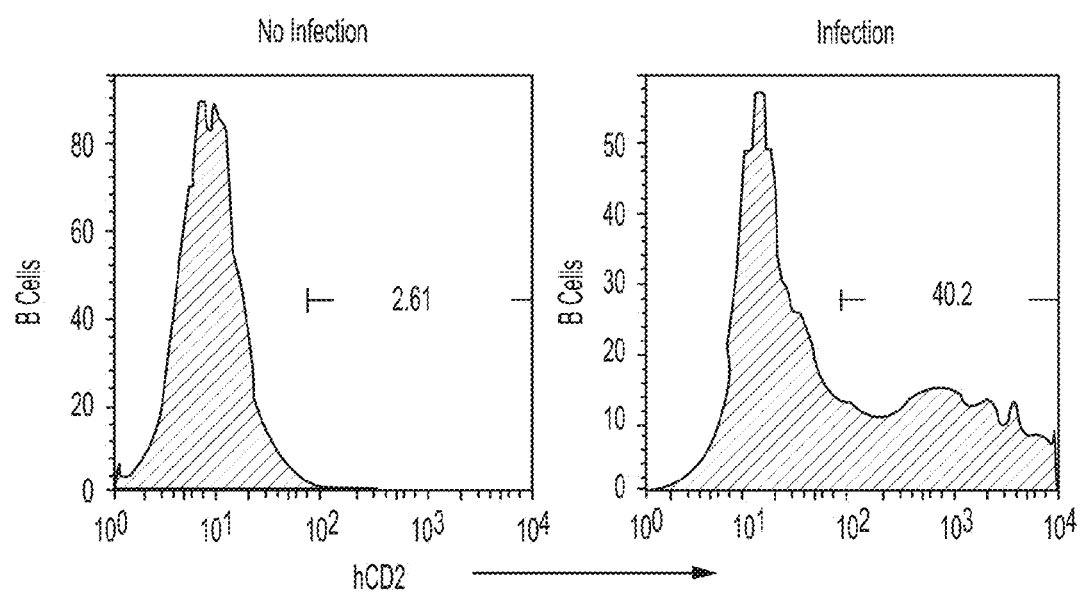

Inactivation of Cbl-b by any suitable method largely by-passes the requirement for CD28 costimulation in cytokine responses of CD8$^+$ T cells. Cultures containing both CD8$^+$ and CD4$^+$ T cells were stimulated, the production of IFN-γ but not IL-2 by wildtype CD8$^+$ T cells was markedly enhanced; however, the production of IFN-γ by Cbl-b$^{-/-}$ CD8$^+$ T cells was comparable to that by purified Cbl-b$^{-/-}$ CD8$^+$ T cells (FIG. 5), suggesting that CD4$^+$ T-cell help does not have an additive effect on the IFN-γ response of Cbl-b$^{-/-}$ CD8$^+$ T cells. Consistent with the effects observed on IL-2 responses, anti-CD3 antibody alone induced significantly greater proliferation of purified Cbl-b$^{-/-}$ CD8$^+$ T cells than that of wildtype T cells (FIG. 1b). Additionally, while the proliferative response of wildtype CD8$^+$ T cells was markedly enhanced when cells were costimulated with anti-CD3 and anti-CD28, reaching a level equivalent to the response of Cbl-b$^{-/-}$ CD8$^+$ T cells stimulated by anti-CD3 alone, the proliferation of Cbl-b$^{-/-}$ CD8$^+$ T cells was not dramatically elevated by CD28 costimulation (FIG. 1b). In other aspects, the invention provides that ablation of Cbl-b activity renders CD8$^+$ T cells capable of responding to TCR stimulation without a requirement for CD28 costimulation and CD4$^+$ T-cell help. FIG. 1c shows that while presence of TGF-β markedly suppressed the proliferation and IFN-γ production of WT CD8+ T cells, the same TGF-β exerted little effect on Cblb–/– CD8+ T cells (FIG. 1C). This result indicates that susceptibility to TGF-β suppression is compromised in Cblb–/– CD8+ T cells.

Rejection of Transplanted Tumors in Cbl-b$^{-/-}$ Mice

Loss of the dependence on CD28 signaling for Cbl-b$^{-/-}$ CD8$^+$ T-cell activation suggested that Cbl-b$^{-/-}$ T cells can be activated by tumor cells in the absence of costimulatory ligands. Cbl-b$^{-/-}$ mice mount an efficient immune response against tumor cells lacking expression of B7 costimulatory molecules. Cbl-b$^{-/-}$ mice are resistant to inoculated murine EL4 and E.G7 thymomas. EL4 cells are derived from a T-lineage lymphoma that developed in a C57 black mouse treated with 9, 10-dimethyl-1, 2-benzanthracene. EL4 cells represent a tumor model with weak immunogenicity (Gorer, P. A. 1950. Studies in antibody response of mice to tumor inoculation. *Br J Cancer* 4:372-379). E.G7 cells are EL4 transfectants that express a transgene encoding chicken ovalbumin (OVA) and, therefore, are considered to be highly immunogenic tumors in which the OVA serves as the tumor-specific antigen (Moore, M. W., F. R. Carbone, and M. J. Bevan. 1988. Introduction of soluble protein into the class I pathway of antigen processing and presentation. *Cell* 54:777-785.) Neither EL4 nor E.G7 lymphomas express cell surface B7.1 or B7.2. Both EL4 and E.G7 lymphomas grow progressively in C57BL/6 mice after subcutaneous inoculation, while in contrast B7-transfected EL4 cells are rejected, demonstrating a critical role of costimulation in the anti-tumor response of wildtype mice (Yu et al., 1998).

Figure 2A:
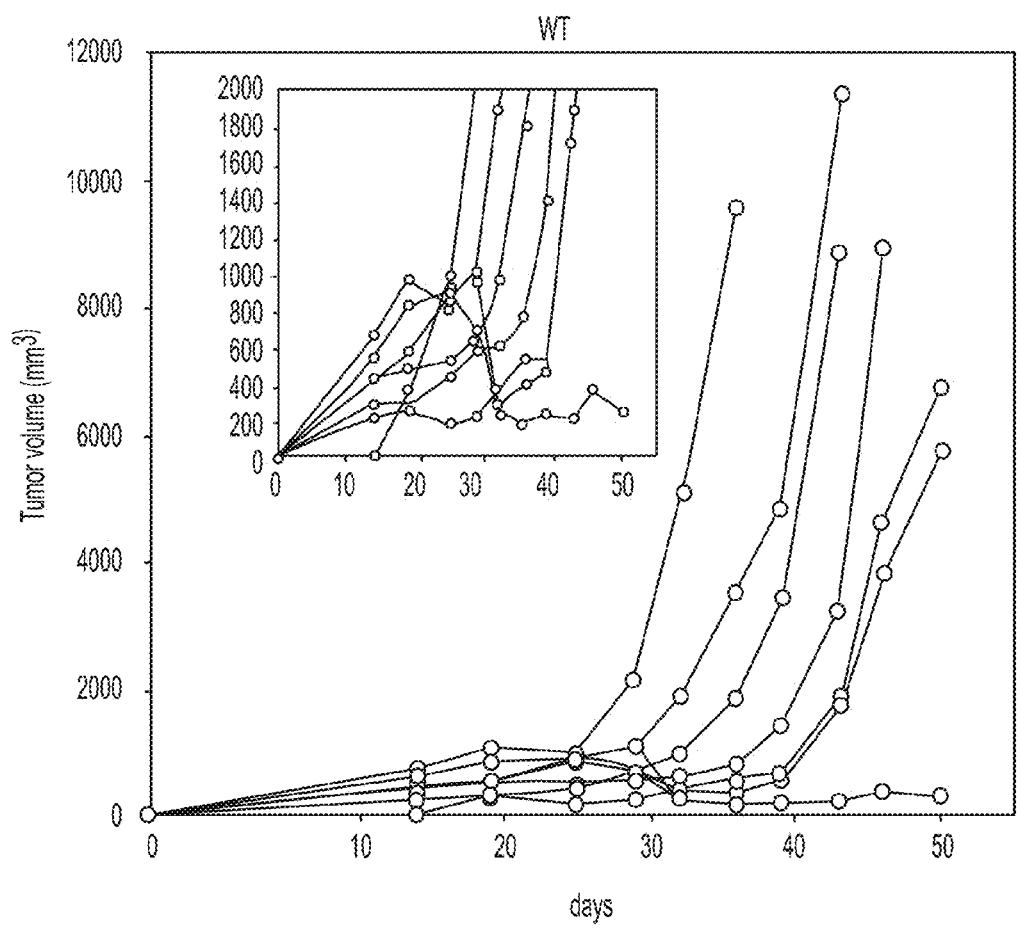
FIGS. 2A-2E show eradication of inoculated tumors in Cbl-b$^{-/-}$ mice.
Figure 2A:
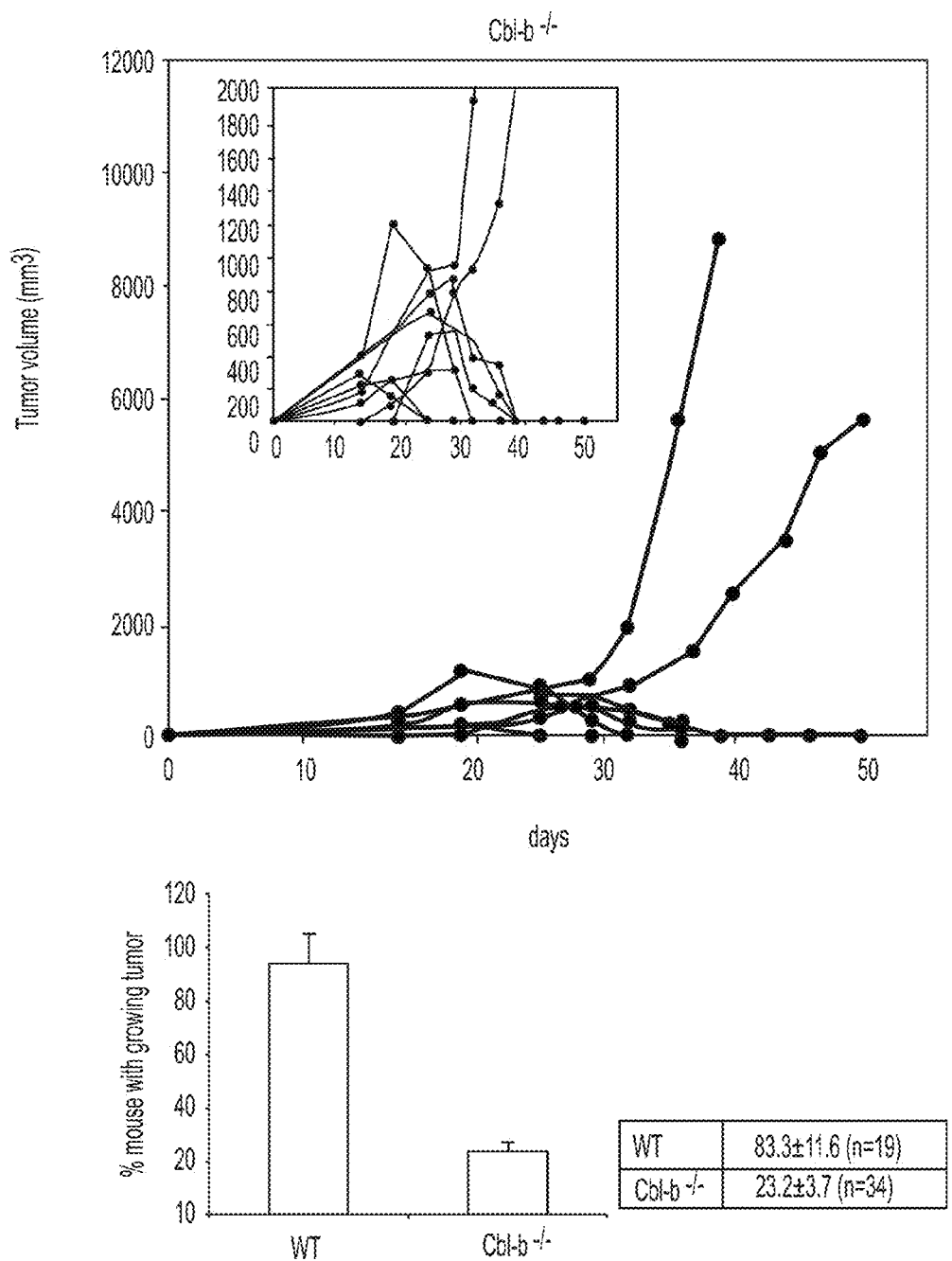

E.G7 cells ($1 \times 10^6$ cells/mouse) were injected into the flanks of wild-type C57BL/6 and Cbl-b$^{-/-}$ mice and then tumor growth was monitored (FIG. 2a). Tumors grew progressively in 83% of wildtype mice (n=19). Only 23% of Cbl-b$^{-/-}$ mice developed tumors, whereas the rest either did not develop tumors or exhibited tumor regression after initial growth (n=34). Thus Cbl-b$^{-/-}$ mice reject E.G7 tumors.

Figure 2B:
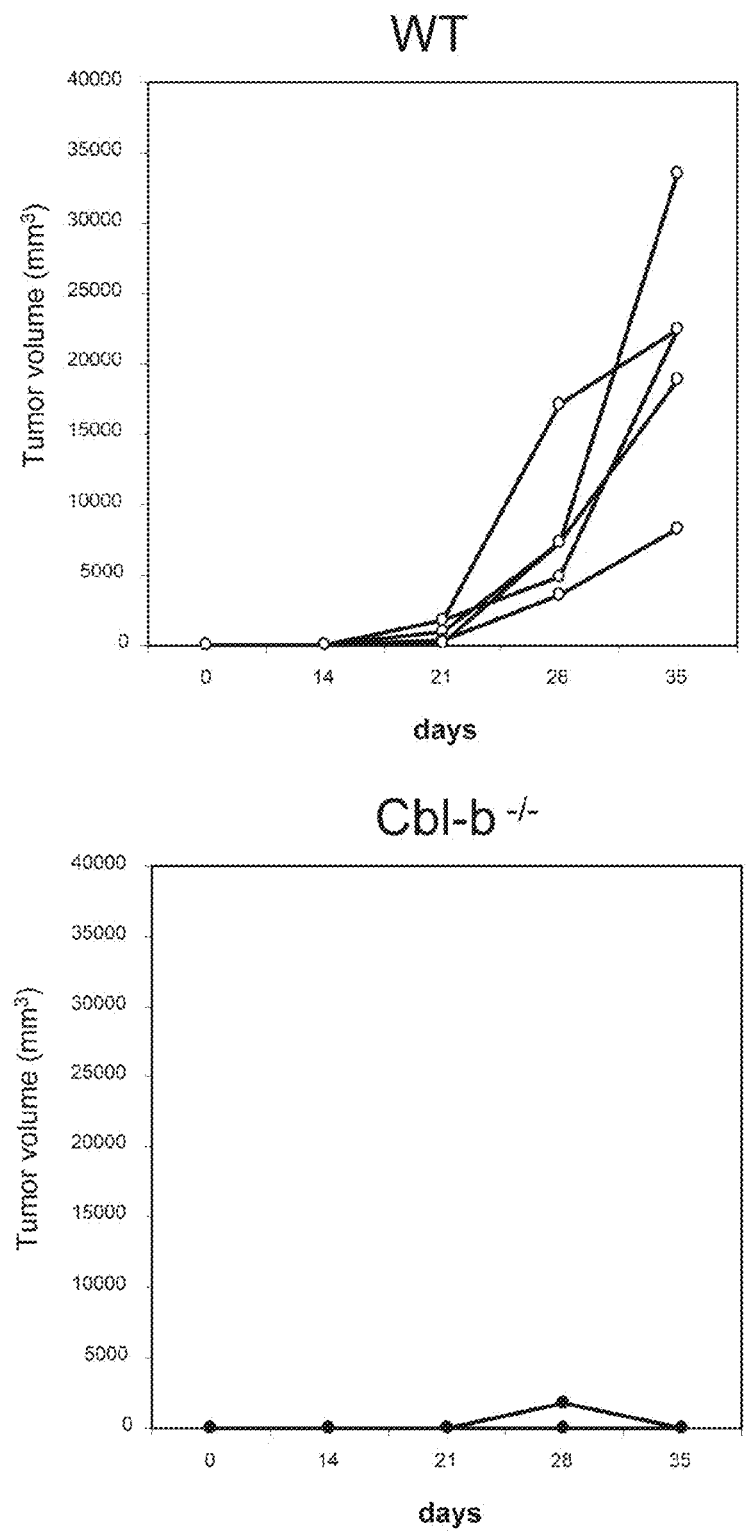
Figure 2C:
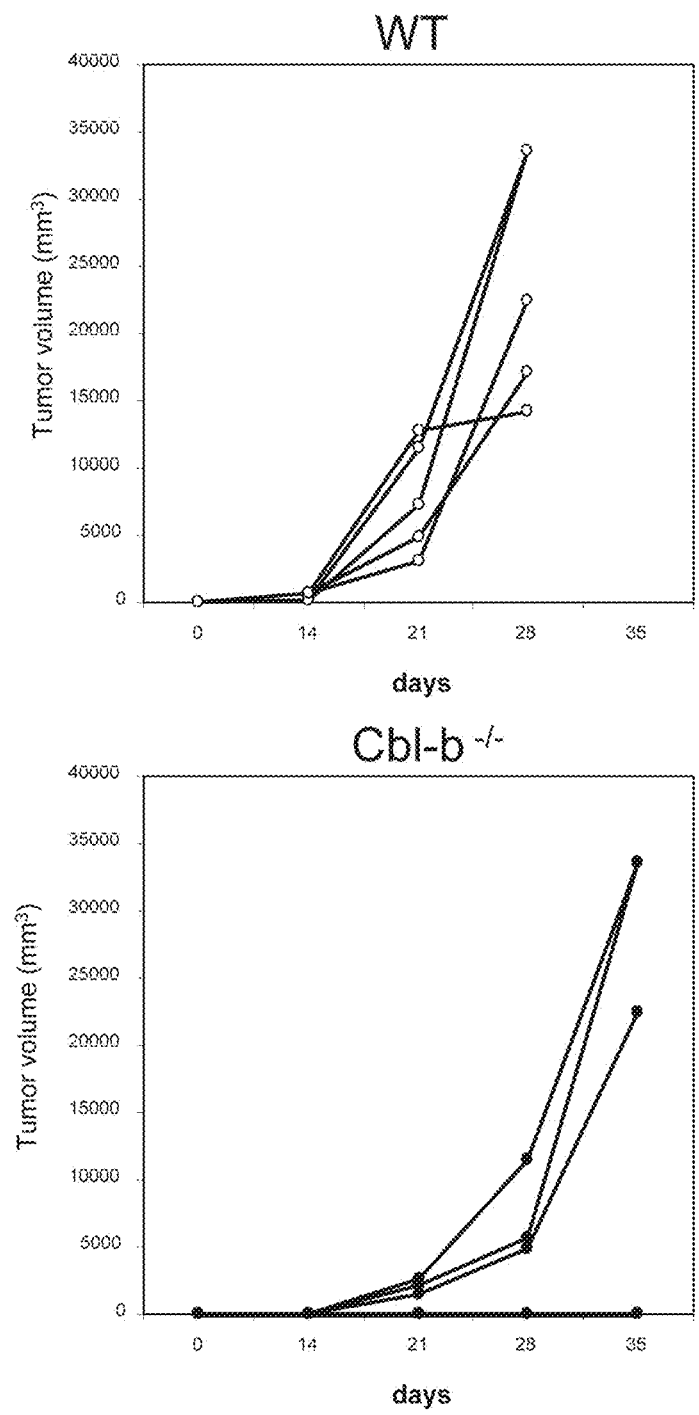
Figure 2D:
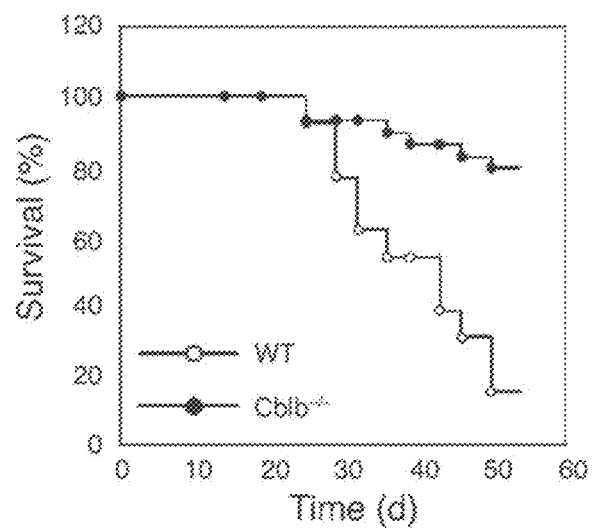
Figure 2E:
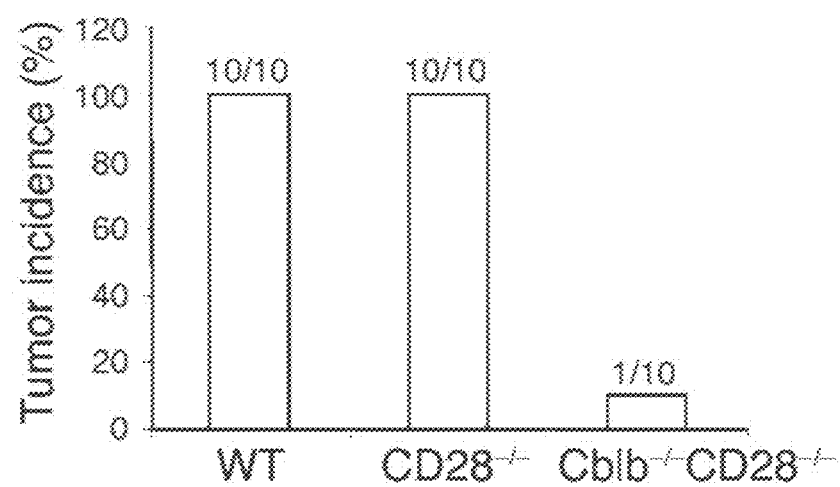

A low dose of EL4 cells ($5 \times 10^4$ cells/mouse) was injected into the flanks of wild-type C57BL/6 and Cbl-b$^{-/-}$ mice and then tumor growth was monitored. Tumors grew rapidly in and killed 85% (17/20) of wild-type mice. The same dose of tumor was completely rejected in Cbl-b$^{-/-}$ mice (FIG. 2b). Inoculation of mice with a high dose of EL4 cells ($2.5×10^5$ cells/mouse) resulted in tumor growth in all wild-type mice (n=10). The same high dose of EL4 cells ($2.5×10^5$ cells/mouse) grew at a much slower rate in seven and did not grew at all in three Cbl-b$^{-/-}$ mice (FIG. 2c). Thus, ablation of Cbl-b confers the ability to reject or attenuate the growth of tumors that express either strong or weak tumor antigens in vivo. FIG. 2e shows that tumor rejection was independent of CD28 because Cblb–/–CD28–/– double-mutant mice also efficiently rejected the inoculated EL4 tumors (FIG. 2e).

TABLE 1

Restoration of c-Cbl Cbl-b dKO thymocyte development by c-Cbl

| | | Total Thymocytes | CD4+CD8+ (%) | CD4+ | CD8+ | CD4+/CD8+ (Ratios) |
|---|---|---|---|---|---|---|
| Exp. 1 | | ($35 × 10^6$) | | | | |
| | GFP− | 42% | 61 | 15 | 12 | 1.2 |
| | GFP+ | 38% @ | 82 | 12 | 3 | 4.0 |
| Exp. 2† | | ($60 × 10^6$) | | | | |
| | GFP− | 48% | 55 | 16 | 18 | 0.88 |
| | GFP+ | 21% @ | 87 | 10 | 3 | 3.33 |
| | | ($100 × 10^6$) | | | | |
| | GFP− | 58% | 51 | 17 | 20 | 0.85 |
| | GFP+ | 18% @ | 80 | 14 | 4 | 3.5 |

@: Cells expressing intermediate level of GFP were not included.
†Results from two independent recipient mice.

Figure 3B:
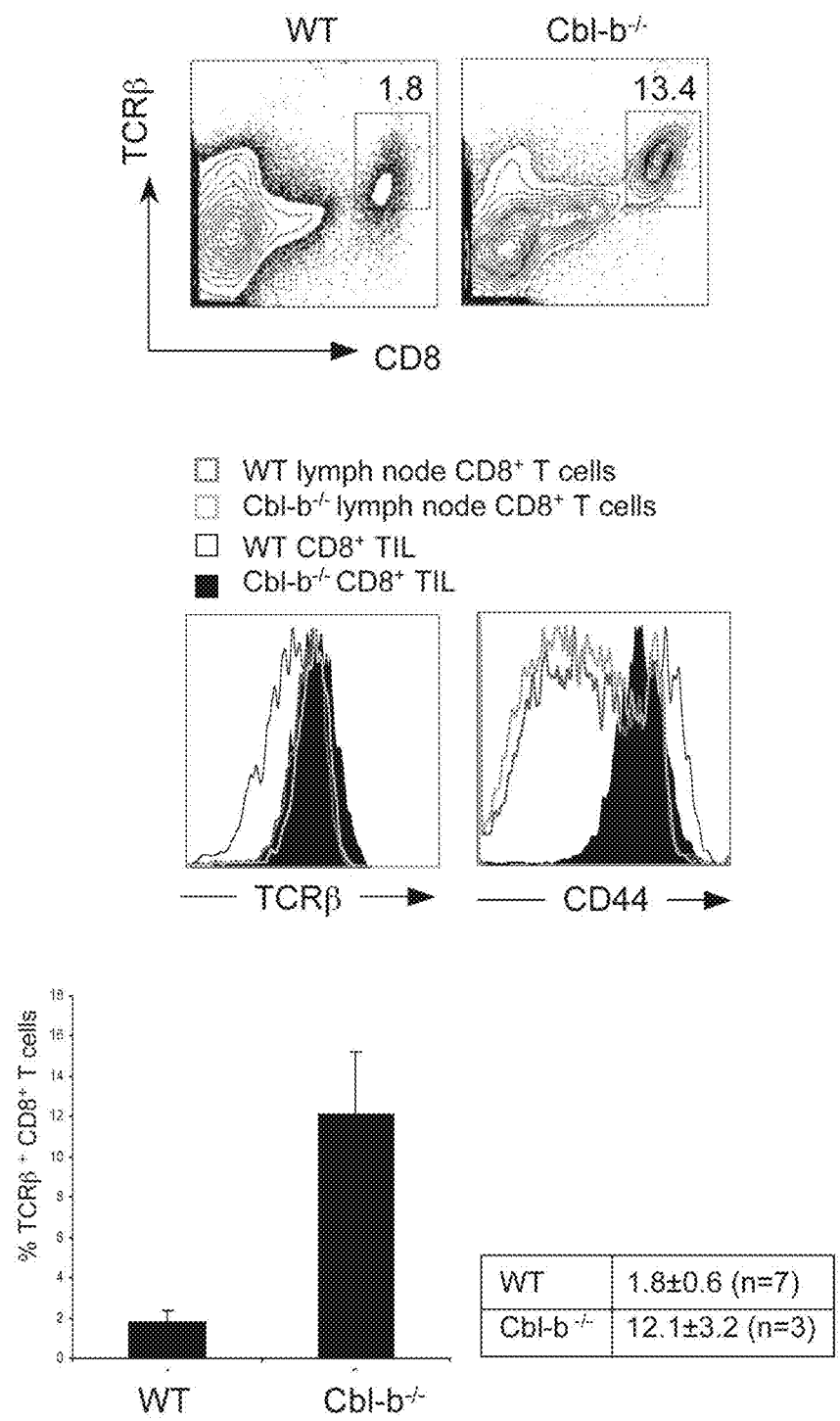

Cbl-b$^{-/-}$ CD8$^+$ T cells efficiently eradicate syngenic tumors. Cbl-b$^{-/-}$ CD8$^+$ T cells respond to antigen stimulation independent of CD28 costimulation and CD4$^+$ T cell help. Resistance of Cbl-b$^{-/-}$ mice to inoculated tumors is primarily mediated by CD8$^+$ T cells. In certain embodiments, infiltration of CD8$^+$ T cells in tumor tissues was examined by immunohistology (FIG. 3a). About $10^6$ E.G7 cells were inoculated into the flanks of C57BL/6 mice and Cbl-b$^{-/-}$ mice by subcutaneous injection. Seven days after inoculation, there were no detectable CD8$^+$ cell infiltrates in tumor tissues in either wild-type or Cbl-b$^{-/-}$ mice. Two weeks after inoculation, a marked increase of CD8$^+$ leukocyte infiltrates was found in tumors in Cbl-b$^{-/-}$ but not wildtype mice. The CD8$^+$ infiltrates remained abundant in the regressing tumors in Cbl-b$^{-/-}$ mice 19 days after inoculation (FIG. 3a); where, infiltration was minimal in tumors in wild-type mice. Flow cytometric analysis revealed that, unlike CD8$^+$ infiltrates in tumors in wild-type mice, which downregulated surface TCRβ, CD8$^+$ infiltrates in tumors from Cbl-b$^{-/-}$ mice expressed TCRαβ receptors at a level comparable to that on naive lymph node T cells (FIG. 3b). These CD8$^+$ T cells also expressed a high level of CD44 (FIG. 3b), suggesting that they were activated CD8$^+$ T cells.

Figure 3C:
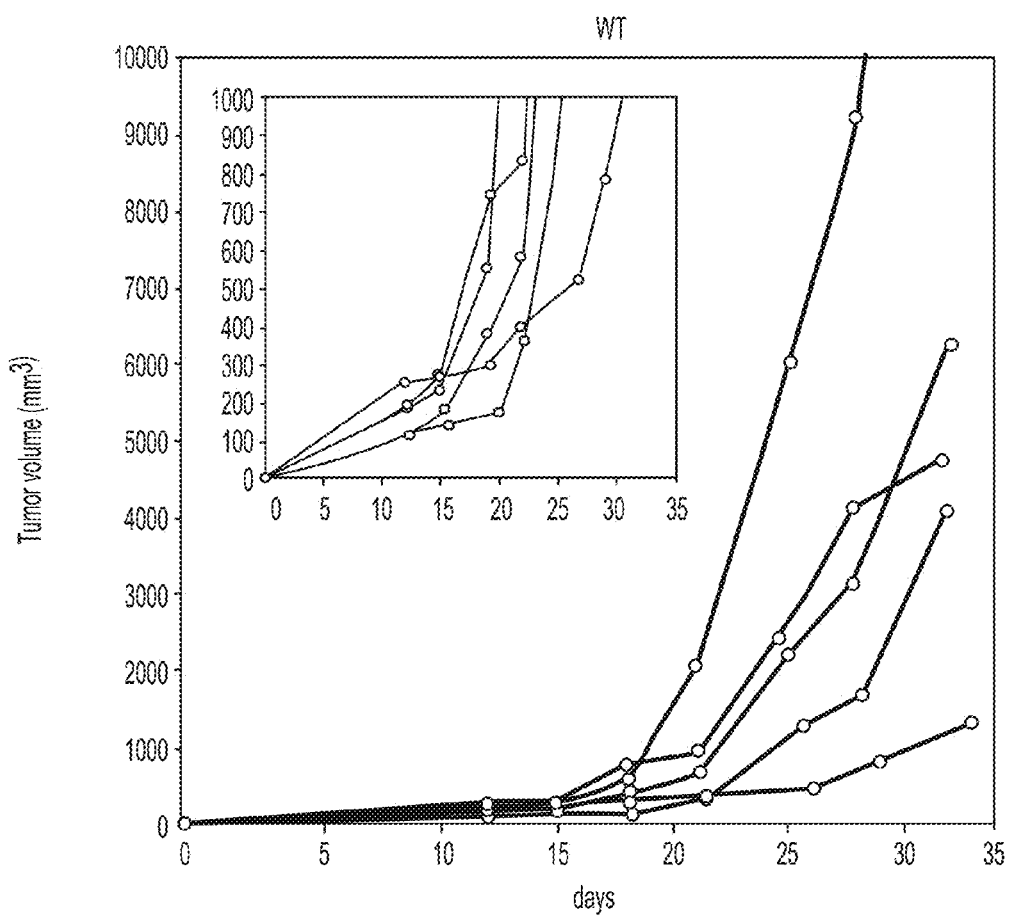
Figure 3C:
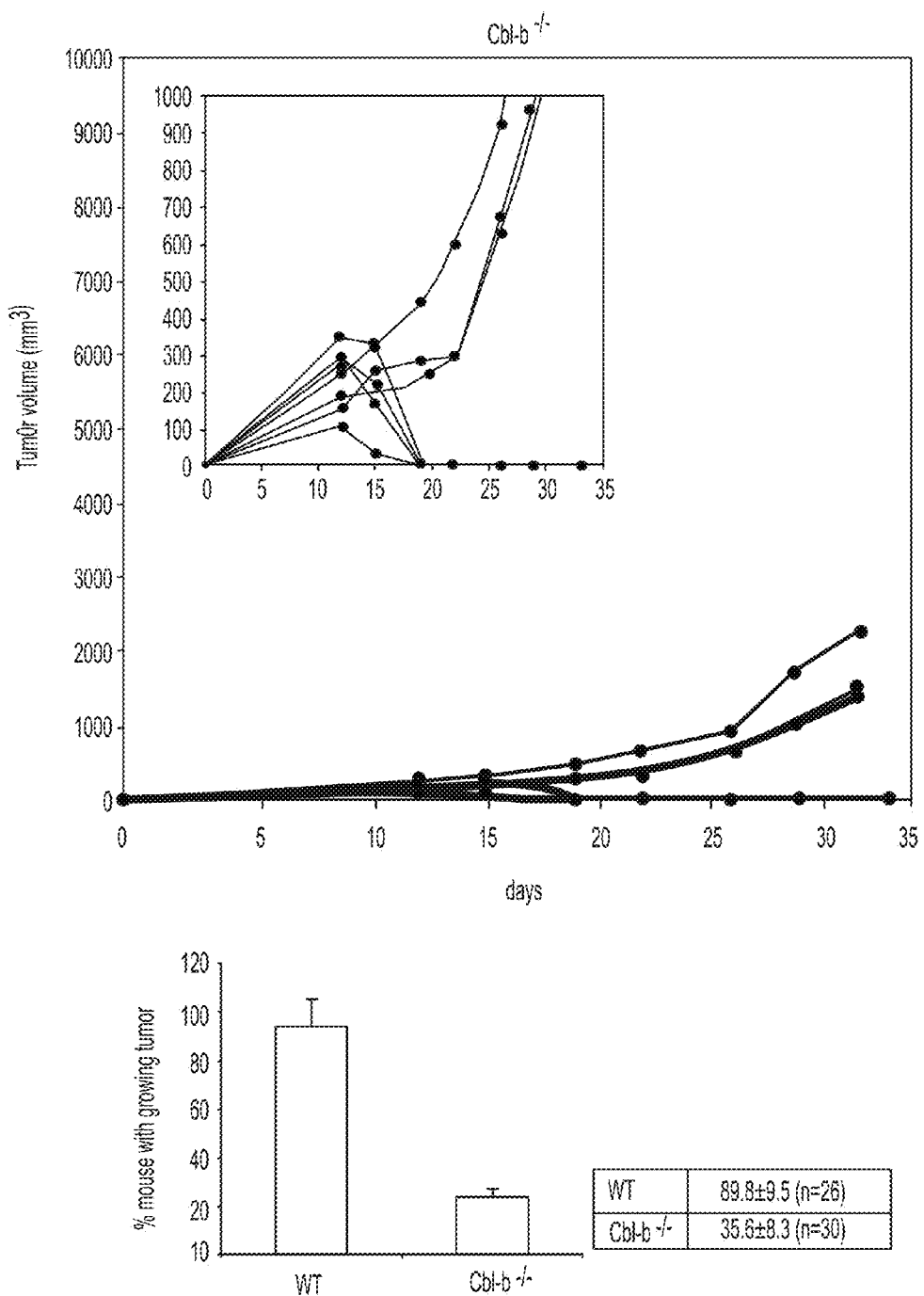
Figure 3D:
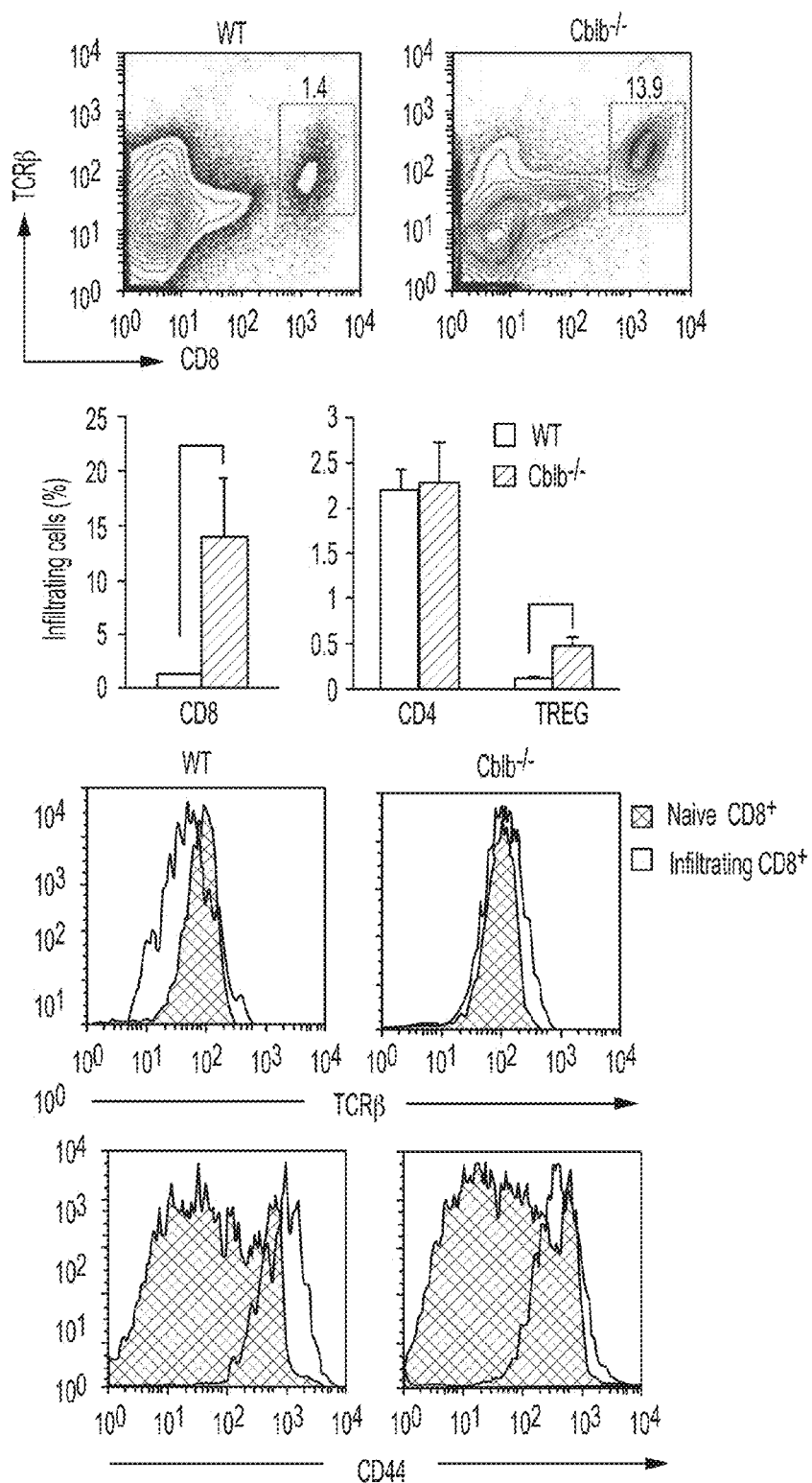

Cbl-b$^{-/-}$ CD8$^+$ T cells are responsible for the eradication of tumors. Purified wildtype or Cbl-b$^{-/-}$ CD8$^+$ T cells ($3×10^6$ cells/mouse) were transferred into E.G7 tumor-bearing mice by intravenous injection, and tumor growth was monitored. The established E.G7 tumors, which were inoculated 8 days before CD8$^+$ T cell transfer, were efficiently eradicated within 4-5 weeks in 65% (20/30) and tumors grew at a much slower rate in the rest of the mice that received Cbl-b$^{-/-}$ CD8$^+$ T cells. At least 90% (23/26) of mice that received wild-type CD8$^+$ T cells had rapid tumor growth (FIG. 3c). In certain aspects, the invention provides that Cbl-b$^{-/-}$ CD8$^+$ T cells are sufficient to mount an efficient immune response against established tumors. FIG. 3d shows that flow cytometric analysis revealed that unlike CD8$^+$ infiltrates in tumors in WT mice, which downregulated surface TCRβ, CD8$^+$ infiltrates in tumors from Cbl-b$^{-/-}$ mice expressed TCRαβ receptors at a level comparable to that on naive lymph node T cells (FIG. 3d). These CD8$^+$ T cells also expressed a high level of CD44 (FIG. 3d), suggesting that they were activated. In addition to CD8$^+$ T cells, tumors in both WT and Cblb$^{-/-}$ mice also contained CD4$^+$ T cell and CD4$^+$ FoxP3$^+$ Treg infiltrates (FIG. 3d). There were significantly more Treg infiltrates in tumors in Cbl-b$^{-/-}$ mice than in WT mice (P<0.005).

Figure 3E:
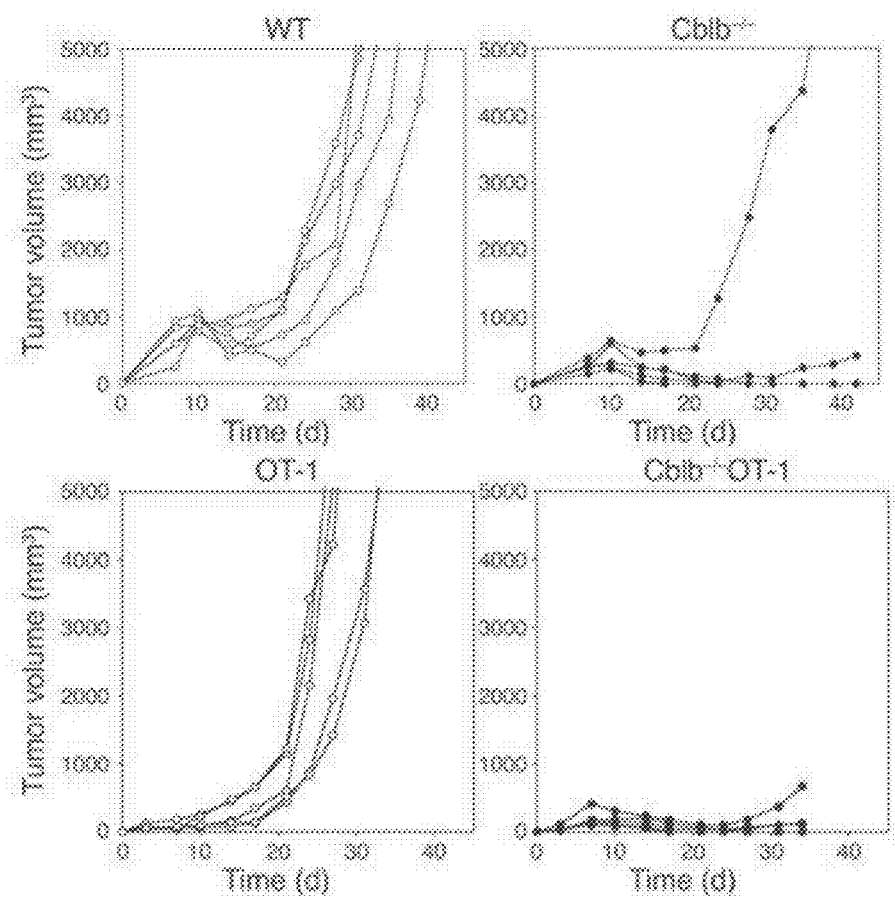
Figure 3F:
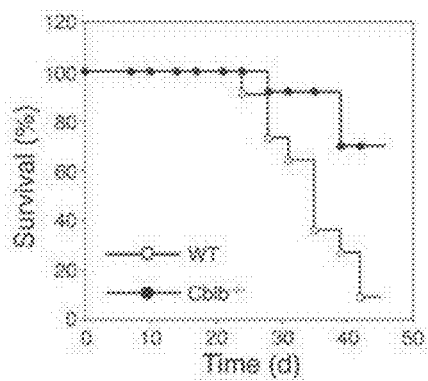

To determine whether Cblb$^{-/-}$ CD8$^+$ T cells were responsible for the eradication of tumors, purified WT or Cblb$^{-/-}$ CD8$^+$ T cells (3×106 cells per mouse) were transferred into E.G7 tumor-bearing mice by i.v. injection and tumor growth was monitored. It was observed that established E.G7 tumors, which were inoculated 7 days before CD8$^+$ T cell transfer, were efficiently eradicated within 4-5 weeks or grew at a much slower rate in mice that received Cblb$^{-/-}$ CD8$^+$ T cells compared with mice that received WT CD8$^+$ T cells (FIG. 3e, left panels). In total, 70% of mice (n=13) adoptively transferred with Cblb$^{-/-}$ CD8$^+$ T cells eradicated tumors and survived. By contrast, more than 90% of mice (n=11) that received WT CD8$^+$ T cells had rapid tumor growth and died (FIG. 3e, right panel). To determine whether the observed rejection of E.G7 tumors was mediated by tumor-specific CD8$^+$ T cells, Cblb$^{-/-}$ mice were crossed to OT1 TCR transgenic mice, which expressed a transgenic TCR recognizing an OVA peptide in context of H-2Kb. The majority of CD8+ T cells developed in OT1 mice express this TCR transgene and are thus capable of recognizing OVA peptide expressed by E.G7 tumor. It was found that adoptive transfer of purified WT OT1 CD8$^+$ T cells ($3×10^6$ cells per mouse) into E.G7 tumor-bearing mice (n=5) failed to prevent any tumor growth. By contrast, transfer of Cbl-b$^{-/-}$ OT1 CD8$^+$ T cells into the tumor-bearing mice resulted in complete regression of the tumors in all of the mice (n=5) (FIG. 3e). Taken together, these data indicate that Cbl-b$^{-/-}$ CD8$^+$ T cells can elicit an efficient immune response against established tumors in a WT host that is otherwise incapable of tumor rejection.

Figure 4:
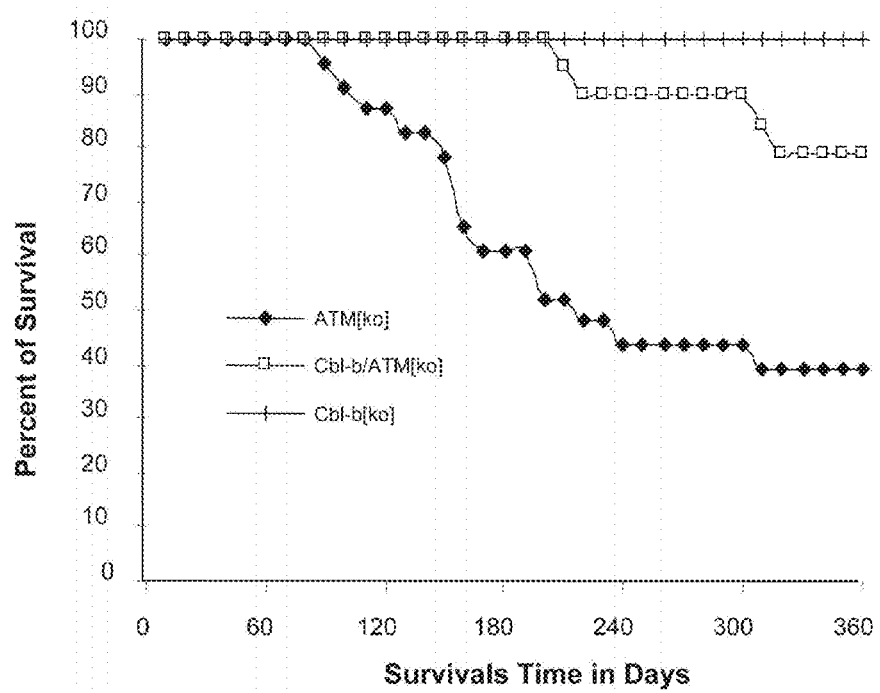
FIG. 4 shows Kaplan-Meier analysis of tumor incidence in Cbl-b$^{-/-}$ ATM$^{-/-}$ double mutant mice. Thymic lymphoma-free survival is plotted versus time in days for Cbl-b$^{-/-}$, ATM$^{-/-}$ (n=25) and Cbl-b$^{-/-}$ ATM$^{-/-}$ (n=21) mice. Cbl-b$^{-/-}$ ATM$^{-/-}$ double mutant mice exhibited reduced incidence of spontaneous lymphoma.

Ablation of Cbl-b prevents spontaneous tumors in ATM$^{-/-}$ mice. Effective recognition and elimination of transplanted E.G7 and EL4 tumors by Cbl-b$^{-/-}$ CD8$^+$ T cells indicates that the Cbl-b$^{-/-}$ mutation facilitates efficient surveillance and protection against spontaneous tumors. In certain embodiments, Cbl-b$^{-/-}$ mice were crossed to ATM$^{-/-}$ mice, and the incidence of T cell lymphomas in and the life span of the resulting double mutant mice were analyzed. Consistent with previous findings (Barlow, C., S. Hirotsune, R. Paylor, M. Liyanage, M. Eckhaus, F. Collins, Y. Shiloh, J. N. Crawley, T. Ried, D. Tagle, and A. Wynshaw-Boris. 1996. Atm-deficient mice: a paradigm of ataxia telangiectasia. Cell 86:159-171), approximately 50% of ATM$^{-/-}$ mice died by 6-7 months of the age, and the majority of these mice developed T cell lymphoma (FIG. 4). In contrast, no lymphomas were observed in Cbl-b$^{-/-}$ ATM$^{-/-}$ double mutant mice (n=21 mice) by 6-7 months of age, and lymphomas occurred in less than 10% (2/21) of mice by 9 months of age. In certain aspects, the invention provides that ablation of Cbl-b function delays and/or prevents the onset of at least some spontaneous tumors.

Eradication of E.G7 tumors by adoptively transferred Cbl-b$^{-/-}$ CD8$^+$ T cells may appear less efficient than eradication of E.G7 tumors in Cbl-b$^{-/-}$ mice. In certain instances, this can be due to the relatively fewer Cbl-b$^{-/-}$ CD8$^+$ T cells in the adoptively transferred mice than Cbl-b$^{-/-}$ mice ($3×10^6$ versus $>1-2×10^7$/mouse). In other instances, Cbl-b$^{-/-}$ CD4$^+$ T cells and/or antigen presenting cells such as dendritic cells may interact with Cbl-b$^{-/-}$ CD8$^+$ T cells in tumor rejection. Experiments using different combination of monoclonal tumor-specific CD8$^+$ and CD4$^+$ T cells and purified APCs as donor cells may help to clarify this issue.

Germline ablation of Cbl-b in ATM$^{-/-}$ mice resulted in a marked reduction of spontaneous tumors, and a consequently increased life span. Given the observation that Cbl-b$^{-/-}$ CD8$^+$ T cells can mount efficient immune responses to transplanted E.G7 and EL4 tumors, the reduced incidence of lymphomagenesis in Cbl-b$^{-/-}$ ATM$^{-/-}$ double mutant mice may result from the improved immune surveillance of Cbl-b$^{-/-}$ CD8$^+$ T cells against the spontaneous tumors that arise in these mice. Because tumorigenesis is a very complex process, another possibility is that the germline Cbl-b$^{-/-}$ mutation decreases tumorigenesis per se, rather than enhancing rejection of tumors arising in Cbl-b$^{-/-}$ ATM$^{-/-}$ mice. Systemic inhibition of Cbl-b function is an effective approach to reduce the incidence of tumors.

Immunogenic Tumor-Bearing Animal Models

In the past decades, tumor-bearing animal models have been widely used to dissect the molecular and cellular mechanisms involved in tumor-immune responses. Many of these models are generated by adoptive transfer of various tumor cells into the MHC-matched syngenic animals. The following tumors are non-limiting examples of animal models that can be used in various embodiments of the present invention. Other tumor models can also be suitable for use in various embodiments of the invention.

E.G7 and EL4 tumor cells and OT1 TCR transgenic (Tg) mice: EL4 cells are B7 negative H-2$^b$ tumor line derived from T-lineage lymphoma from a C57BL/6 mouse treated with 9, 10-dimethyl-1, 2-benzanthracene. These cells express only native and perhaps some mutated self-antigens, thus representing a model of tumors with weak antigenicity. The E.G7 tumor cell line is a derivative of EL4 that expresses a chicken ovalbumin (Ova) transgene. It displays the immunodominant epitope of Ova on its surface, identified as the eight-residue peptide Ova 257-264 (SIINFEKL (SEQ ID NO: 2))(41). Because Ova is not expressed in murine cells, it serves as a tumor-specific antigen. Thus, E.G7 represents a tumor model that mirrors strong antigenic tumors such as virus transformed cells. Both EL4 and E.G7 cells, when inoculated subcutaneously in C57BL/6 mice, progressively develop into local solid tumors in a dose dependent manner, and eventually kill the recipient mice beyond 4-weeks (42). In E.G7 tumor tissue, Ova-specific CTLs can be detected, however, they are anergic to tumor-antigen (Ova) stimulation (42). OT1 mice are TCR transgenic mice in which the transgene-expressing CD8$^+$ T cells express a Vβ8 and Vα2 TCR transgene and specifically recognize the Ova peptide (SIINFEKL (SEQ ID NO: 2)) in the context of K$^b$ class I MHC (43, 44). Inoculation of E.G7 cells into OT1 Tg mice also results in tumor growth, suggesting that the presence of high numbers of tumor-specific CTLs is not sufficient to reject the tumor. E.G7 cells can be used as a tumor model of cells that express tumor-specific antigen, and OT1 TCR Tg mice can be used as the source for monoclonal tumor-specific CD8$^+$ T cells.

B16 tumor cells and Pmel-1 TCR transgenic mice: The B16 melanoma is poorly immunogenic and highly aggressive in C57BL/6 mice (45). The B16 melanoma cells express the mouse homolog (pmel-17) of human gp100, an enzyme involved in pigment synthesis in normal melanocytes (34). In this tumor model gp100 represent non-mutated self-antigens that are usually expressed by the majority of tumor cells (34). Pmel-1 Tg mice are TCR transgenic mice in which the CD8$^+$ T cells express a TCR recognizing gp100 (gp100$_{25\text{-}33}$)-H-2D$^b$ complexes. Despite the increased number of antigen-specific CD8$^+$ T cells, B16 melanomas develop at the same growth rate in Pmel-1 Tg mice as that in wildtype C57BL/6 mice, because essentially all gp100-specific H-2D$^b$-restricted CD8$^+$ T cells are anergic (34). The anergic state of gp100, H-2D$^b$-restricted CTLs can be reversed by inoculated melanomas expressing a B7 ligand (35), or by in vivo administration of high-dose IL-2 and vaccination with a variant gp100 peptide (34), resulting in complete and durable eradication of the tumor burdens. Since a gradual, limited vitiligo caused by autoimmunity against normal melanocytes also occurs in most of the Pmel-1 Tg mice where tumor destruction is observed (34), this system allows investigation of potential side-effects of tumor immunotherapy, such as autoimmunity, caused by anti-tumor immune response against tumor-associated antigens that are also expressed by the normal tissue.

CD8$^+$ T Cells can be Efficiently Activated in the Absence of CD28 Costimulation Cbl-b$^{-/-}$ mice were generated by gene targeting (56). Cbl-b$^{-/-}$ mutation does not affect the development of major lymphoid organs. Development of both B and T lymphocytes in Cbl-b$^{-/-}$ mice appears to be normal. Cbl-b$^{-/-}$ mice can be highly susceptible to autoimmune diseases. Cbl-b$^{-/-}$ mutation does not affect antigen-induced B-cell activation. In contrast, activation of Cbl-b$^{-/-}$ CD4$^+$ T cells no longer required CD28 costimulation, in striking contrast to the wild-type T cells for which the CD28 costimulation was necessary to induce a productive response, such as rigorous cell proliferation and IL-2 production. To determine whether Cbl-b$^{-/-}$ mutation substitutes CD28 costimulation in immune response, Cbl-b$^{-/-}$ mice were crossed to CD28$^{-/-}$ mice, and in vitro T-cell proliferation and in vivo T-cell-dependent anti-NP-antibody responses in Cbl-b$^{-/-}$ CD28$^{-/-}$ double mutant mice were examined (59). While CD28$^{-/-}$ T cells can not mount any detectable proliferation upon anti-CD3 antibody stimulation, Cbl-b$^{-/-}$ CD28$^{-/-}$ T cells proliferate normally under the same condition. While CD28$^{-/-}$ mice failed to produce any detectable serum anti-NP antibodies, Cbl-b$^{-/-}$ CD28$^{-/-}$ double mutant mice elicit normal anti-NP antibody responses of different Ig isotypes. The anti-NP antibody responses in Cbl-b$^{-/-}$ mice were not enhanced as compared to that elicited in wild-type mice, suggesting that Cbl-b$^{-/-}$ mutation merely results in substitution of CD28 signaling rather than a general enhancement of T-dependent responses during T cell activation.

Thus in the absence of Cbl-b, activation of CD4$^+$ T cell is CD28 independent. Activation of Cbl-b$^{-/-}$ CD8$^+$ T cells is not CD28 dependent. In certain embodiments, the production of IL-2 and IL-gamma in anti-CD3 antibody-stimulated Cbl-b$^{-/-}$ CD8$^+$ T cells is measured by intracellular staining followed by FACS analysis (61). While the production of these cytokines by wild-type CD8$^+$ T cells clearly requires CD28 costimulation, Cbl-b$^{-/-}$ CD8$^+$ T cells stimulated by anti-CD3 antibody alone produce levels of IL-2 and IL-gamma as high as the levels in anti-CD3 and anti-CD28 costimulated wildtype CD8$^+$ T cells. Thus Cbl-b$^{-/-}$ CD8$^+$ T cells can be activated efficiently in the absence of CD28 costimulation.

Cbl-b$^{-/-}$ Mice Efficiently Rejected Inoculated Tumors with Strong or Weak Antigenicity Most immunogenic tumors do not express ligands for costimulatory molecules. This has been considered to be one of the mechanisms by which tumors break immune surveillance and diminish the effectiveness of tumor immunotherapy. Because Cbl-b$^{-/-}$ T cells do not require CD28 costimulation for activation, Cbl-b$^{-/-}$ mice are resistant to E.G7, EL4, or B16 tumor implantation. E.G7 tumor cells are chicken-ovalbumin (Ova)-expressing EL4 cells, a thymoma cell line derived from C57BL/6 mice. This cell line has is used as a model of strong antigenic tumors that express a tumor-specific antigen, since chicken Ova is not expressed in normal mice. In contrast to E.G7, EL4 and B16 melanoma cells are derived directly from primary tumors, thus representing tumors that express either weak tumor-specific or only self-antigens. To avoid allogenic responses against the implanted tumors, Cbl-b$^{-/-}$ mice were backcrossed to C57BL/6 mice syngenic to these tumors for 12 generations. Inoculation of E.G7 cells ($10^6$/mouse) subcutaneously into the flank of the wildtype C57BL/6 mice results in a rapid growth of solid tumors, indicating that these mice cannot mount an immune response against the inoculated E.G7 tumor. In contrast, inoculation of the same amount of E.G7 cells into Cbl-b$^{-/-}$ mice results in much lower incidences of tumors. In some Cbl-b$^{-/-}$ mice the tumors grew initially, and then regressed one to two weeks later. Because B7s are not expressed on E.G7 cells (36), this result thus indicates that ablation of Cbl-b can render animal resistance to the inoculated strong antigenic tumors that do not express B7s.

To determine whether Cbl-b$^{-/-}$ mice mount immune responses against tumors that express weak or self-antigens, the susceptibility of Cbl-b$^{-/-}$ mice to implanted EL4 and B16 tumors was examined. While wild-type control mice developed tumors after inoculation with low numbers of EL4 ($2.5 \times 10^4$) or B16 ($1.0 \times 10^4$) cells/mouse, Cbl-b$^{-/-}$ mice that received the same numbers of the tumor cells did not develop any tumor during the same period. Inoculation of high doses of EL4 ($1.25 \times 10^5$) or B16 ($1.25 \times 10^5$) cells resulted in tumor growth in both wildtype and Cbl-b$^{-/-}$ mice. The impaired ability of Cbl-b$^{-/-}$ mice to reject the high dose of tumor cells might reflect the facts that the frequency of tumor specific T cells in natural T cell repertoire is too low to override the rapid growth of tumor cells. This possibility can be quantitatively assessed for example by using tumor-specific T cells from TCR transgenic mice. Thus Cbl-b$^{-/-}$ mice elicit immune responses against tumors expressing either strong or weak tumor antigens.

Rejection of Implanted E.G7 Tumors is Mediated by T Cells

Previous experiments have shown that rejection of immunogenic tumors is primarily mediated by T cells. Consistent with this result, immunohistological and flow-cytometry studies revealed that E.G7 tumor tissues were infiltrated by large numbers of CD8$^+$ cells. To determine the role of T cells in E.G7 tumor rejection in Cbl-b$^{-/-}$ mice, we examined the growth rate of E.G7 tumors in T cell-depleted Cbl-b$^{-/-}$ mice. Depletion of T cells was achieved by repeated intravenous injection of anti-CD4 and anti-CD8 antibodies (100 μs/mouse/injection). This treatment eliminated the majority of CD4$^+$ and CD8$^+$ T cells from both the spleen and lymph node of the treated mice. To determine whether T cell-depleted Cbl-b$^{-/-}$ mice were able to mount an efficient anti-tumor response, $1 \times 10^6$ E.G7 cells we inoculated into Cbl-b$^{-/-}$ mice and then the growth of the tumors was monitored weekly. In contrast to the non-treated Cbl-b$^{-/-}$ mice, in which tumors were rejected, all three T-cell depleted Cbl-b$^{-/-}$ mice bore tumors bigger than 20 mm in diameters by the end of 5 weeks after the inoculation. Thus CD8$^+$ T cells are responsible for tumor rejection in Cbl-b$^{-/-}$ mice.

Massive Infiltration of CD8$^+$ T Cells in E.G7 Tumor Tissue

Tumor mass often contains large numbers of CD8$^+$ T cell infiltrates. These infiltrates usually are not responsive to tumor antigen stimulation, despite the fact that the infiltrates are enriched for tumor specific CTLs. To determine whether E.G7 tumor tissues contain infiltrated CD8$^+$ T cells, E.G7 cells were inoculated subcutaneously into the flank of Cbl-b$^{-/-}$ and C57BL/6 mice. Tumor-infiltrating CD8$^+$ T cells in tumor tissue sections were identified by immunohistological staining using anti-CD8 antibody. In tumors collected at about $20^{th}$ day after the inoculation, CD8$^+$ (CD8α$^+$) cells are detected in tumor samples from both tumor-bearing wild-type and Cbl-b$^{-/-}$ mice, with significantly more CD8$^+$ infiltrates in tumors from the Cbl-b$^{-/-}$ mice.

To quantitatively determine whether the observed CD8α$^+$ cells were CD8$^+$ T cells, tumor tissues was digested with collagenase to generate single cell suspension. CD8$^+$ cells in the tumor tissues were then analysis by flow cytometry after staining the cells with anti-TCRβ, CD8α$^+$, CD44 and CD62L antibodies. The CD8$^+$ cells in tumor tissues expressed TCRβ chain, indicating that they were indeed CD8$^+$ T cells. In addition, in agreement with immunohistological analysis, tumor tissue from Cbl-b$^{-/-}$ mice contained in average 10 times more CD8$^+$ T cells. These Cbl-b$^{-/-}$ T cells also exhibited phenotypes of activated T cells, including a high level of CD44 and a low level of CD62L. In contrast, although CD8$^+$ T cells from tumors of wildtype mice also expressed similar levels of CD44 and CD62L, they expressed a low level of TCRβ, suggesting that these CD8$^+$ T cells from wild type mice are anergic cells. In certain aspects, the present invention provides that there is an extensive expansion of CD8$^+$ T cells in tumors of Cbl-b$^{-/-}$ mice. The CD8$^+$ T cells in tumor tissues can be used as the source of tumor specific CD8$^+$ CTLs, which can be used in adoptive transfer therapy.

Adoptive Transfer of Purified CD8$^+$ T Cells into E.G7 Tumor-Bearing C57BL/6 Mice Resulted in the Regression of Established Tumors Anti-tumor responses in Cbl-b$^{-/-}$ mice are mediated by CD8$^+$ T cells. Anti-tumor immune response against tumor cells can be elicited by adoptive transfer of CD8$^+$ T cells. The method can comprise providing and/or isolating purified CD8$^+$ T cells from Cbl-b$^{-/-}$ or wildtype mice, wherein in certain embodiments purification of CD8$^+$ T cells can be done by magnetic cell sorting (MACS), transferring the purified CD8$^+$ T cells ($3 \times 10^6$ cells/mouse) into E.G7 tumor bearing C57BL/6 mice by intravenous injection, and monitoring tumor growth weekly. Adoptive transfer of wild-type CD8$^+$ T cells into the tumor-bearing mice did not affect tumor growth. By contrast, 5 out 6 mice that received Cbl-b$^{-/-}$ CD8$^+$ T cells exhibited tumor regression four weeks after the transfer. The invention provides that Cbl-b$^{-/-}$ CD8$^+$ T cells are sufficient to mediate the anti-tumor responses. In certain embodiments, Cbl-b$^{-/-}$ CD8$^+$ T cells include CD8$^+$ T cells in which the activity of Cbl-b has been reduced by any suitable agent or method known in the art, including but not limited to knock-down by use siRNA, shRNA, transfection with a dominant negative form of Cbl-b, knock out of the genomic copy of Cbl-b, are sufficient to mediate the anti-tumor responses. A polypeptide, which is expected to function as dominant negative form against Cbl-b, is a polypeptide which contains only the PTB domain of Cbl-b, positions 1-377 in the amino acid sequence of Cbl-b.

Cbl-b$^{-/-}$ T Cells are Resistant to TGF-Beta Suppression

TGF-beta produced by tumors or regulatory cells is one of the mechanisms that can prevent T cell mediated anti-tumor immune surveillance. A previous report suggested that Cbl- $b^{-/-}$ CD4+ T cells were resistant to TGF-beta mediated suppression. To determine whether Cbl-b$^{-/-}$ CD8 T cells respond to antigen stimulation in presence of TGF-beta, in vitro anti-CD3-induced proliferation and IFN-gamma production of the purified CD8$^+$ T cells from wild-type and Cbl-b$^{-/-}$ mice in the presence or absence of TGF-beta were examined. Wild-type CD8$^+$ exhibited a TGF-beta dose dependent suppression of proliferation, as evidenced by a reduced diminishment of CFSE intensity in the presence of TGF-beta, the proliferation of Cbl-b$^{-/-}$ CD8$^+$ T cells was not affected even in the presence of the highest dose (5 µg/ml) of TGF-beta. The presence of TGF-beta (5 µg/ml) did not affect Cbl-b$^{-/-}$ CD8$^+$ T cells with respect to IFN-gamma production. By contrast, the production of IFN-gamma was completely suppressed in wildtype cells by the same concentration of TGF-beta. In certain aspects, the invention provides that Cbl-b deficient CD8$^+$ T cells, including but not limited to Cbl-b$^{-/-}$ CD8$^+$ T cells, respond to tumors even in the environment where TGF-beta is present.

Quantitating the Ability of Cbl-b$^{-/-}$ CTLs to Mount Efficient Responses Against Various Tumors Tumor cells may escape immune surveillance by several mechanisms, including weak antigenicity, lack of costimulatory signals, and prevention of T cell responses by TGF-beta, regulatory T cells, and tumor barrier. Cbl-b$^{-/-}$ mice efficiently reject strong antigenic tumor (E.G7). Cbl-b$^{-/-}$ CD8$^+$ T cells are responsible for the tumor rejection. In other aspects, the invention provides that weak antigenic tumors such as EL4 and B16 are rejected only when these tumors when are inoculated at low doses, suggesting that either the activation of tumor specific T cells by these tumors is less efficient or that there is a low frequency of tumor-specific CD8$^+$ T cells. Since Cbl-b$^{-/-}$ CD8$^+$ T cells are nevertheless activated by these tumors, adoptive transfer of a large number of tumor-specific Cbl-b$^{-/-}$ CD8$^+$ T cells may significantly augment immune responses against these tumors.

In certain aspects, the invention provides methods to quantitatively determine the efficiency of tumor antigen-specific Cbl-b$^{-/-}$ CD8$^+$ T cells in eradicating strong and weak antigenic tumors using TCR transgenic Cbl-b$^{-/-}$ CD8$^+$ T cells. To explore whether Cbl-b$^{-/-}$ CD8$^+$ T cells can respond to tumor under various suppressive conditions, determination can include whether Cbl-b$^{-/-}$ CD8$^+$ T cells can eliminate tumors that may prevent T cell responses through secreting TGF-beta, recruiting NKT cells, or tumor barrier using various tumor models. Results from these studies provide not only a quantitative measurement about the efficiency of tumor specific Cbl-b$^{-/-}$ CTLs against strong or weak antigenic tumors but also demonstrate that Cbl-b$^{-/-}$ CD8$^+$ T cells can be used to treat tumors with other negative regulation against immune responses.

Tumor Models and CD8$^+$ TCR-Transgenic Mice

Tumor cells can express "foreign" antigens such as viral components or mutated self-proteins that do not exist in healthy individuals. Adoptive transfer of CD8$^+$ T cells recognizing these antigens may elicit immune responses specifically against the tumor cells. However, in many cases tumor cells express only native non-mutated self-antigens (1). T cells that recognize these antigens are usually anergic, and immune responses against these antigens, if being elicited, could also damage the normal tissues. TCR transgenic (Tg) mouse models of tumors expressing either a "foreign" or a native tumor antigen can be used to recapitulate the situations of tumors that bear either a tumor-specific "foreign" antigen or a non-mutated "self" antigen. One advantage of using TCR transgenic T cells for our study is that the quantity of tumor antigen-specific T cells can be easily determined based on transgenic TCR expression.

Strong Antigenic Tumor and OT1 TCR Tg Mice

E.G7 tumors (MHC H-2$^b$) are EL4 thymomas expressing a transgene, chicken ovalbumin (Ova). In C57BL/6 (H-2$^b$) mice, E.G7 cells can be used as a tumor model that express a "foreign" antigen-Ova. The Ova-specific CD8$^+$ T cells can be obtained from OT1 TCR Tg mice (H-2$^b$), which specifically recognize an Ova peptide in the context of H-2K$^b$. Under normal circumstances non-immunized OT1 mice do not reject inoculated E.G7 tumors, and adoptive transfer of naïve OT1 CD8$^+$ T cells cannot eradicate established E.G7 tumors, suggesting that OT1 CD8$^+$ T cell response against E.G7 cells are suppressed. However, E.G7 tumor cells expressing a B7 transgene can be efficiently rejected by OT1 Tg mice even in the absence of Ova immunization, suggesting that costimulatory signals are critical for the priming and effector function of OT1 Tg T cells. Cbl-b$^{-/-}$ OT1 Tg mice (in C57BL/6 background) can be used to elucidate the efficiency of tumor-specific Cbl-b$^{-/-}$ CD8$^+$ T cells in the eradication of the established E.G7 tumors.

B16 Melanoma and Pmel-1 TCR Tg Mice

B16 melanoma is a weak-immunogenic tumor model. B16 expresses a native self-antigen, the melanocyte differentiation antigen gp100. Subcutaneous inoculation of B16 into C57BL/6 mice results in growth of solid tumor. CD8$^+$ T cells against B16 tumor can be obtained from Pmel-1 TCR Tg mice that express a TCR recognizing gp100 antigen in the context of H-2D$^b$ complexes. It has been found that in the absence of immunization, Pmel-1 mice do not reject the inoculated B16 melanoma due to T cell tolerance to self-antigen gp100. However, a robust response of tumor-rejection can be induced by either enforced expression of B7 on the tumor cells, or upon vaccination with a variant gp100 peptide and high-dose IL-2 administration. Cbl-b$^{-/-}$ Pmel-1 Tg mice were generated by breeding.

Adoptively Transferred Cbl-b$^{-/-}$ Tumor-Specific CD8$^+$ T Cells can Eradicate the Established Tumor Burden in Host Mice The development of Ova and gp100-specific CD8$^+$ T cells in Cbl-b$^{-/-}$ OT1 and Cbl-b$^{-/-}$ Pmel-1 mice can be examined by flow cytometry. T cells from wildtype OT1 and Pmel-1 Tg mice can be used as controls. OT1 and Pmel-1 TCR transgenic CD8$^+$ T cells can be identified by staining cells with a combination of anti-CD8 and anti-TCR Vβ8 and Vα2 or anti-TCR Vβ13 and Vα1 antibodies, respectively. The development of CD8$^+$ T cells should not be altered in Cbl-b$^{-/-}$ TCR Tg mice, because Cbl-b$^{-/-}$ mutation dose not have any measurable impact on the development of CD4$^+$ and CD8$^+$ T cells (55, 56).

In certain embodiments, it can be determined whether activation of Cbl-b$^{-/-}$ OT1 and Cbl-b$^{-/-}$ Pmel-1 Tg CD8$^+$ T cells require CD28 costimulation. CD8$^+$ T cells can be purified from the spleen and lymph nodes of Cbl-b$^{-/-}$ OT1 and Cbl-b$^{-/-}$ Pmel-1 mice using a MACS column according to CD8$^+$ T cell purification protocol (Miltenyi Biotec). The rates of cell proliferation and the levels of cytokines produced by the activated CD8$^+$ T cells, such as IL-2 and IFN-gamma, can be respectively determined by $^3$H-thymidine incorporation, flow cytometry, and ELISA after stimulating cells with anti-CD3 or anti-CD3 and anti-CD28 antibodies. Cbl-b$^{-/-}$ TCR Tg CD8$^+$ T cells proliferate vigorously and produce large amounts of cytokines, including IL-2 and IFN-gamma, in response to the anti-CD3 antibody stimulation alone. In contrast, a strong activation of wild-type OT1 and Pmel-1 Tg CD8$^+$ T cells strictly depends on CD28 costimulation. To determine whether Cbl-b$^{-/-}$ Ova and gp100-specific T CD8$^+$ T cells are resistant to TGF-beta suppression, proliferation and IFN-gamma production can be measured in the purified Cbl-b$^{-/-}$ TCR Tg CD8$^+$ T cells by CFSE labeling and intracellular staining, after cells are activated with anti-CD3 and CD28 antibodies in the presence of various concentration of TGF-beta. Cbl-b$^{-/-}$ TCR Tg CD8$^+$ T cells should exhibit a similar resistance to TGF-beta suppression as non-TCR transgenic Cbl-b$^{-/-}$ CD8$^+$ T cells.

CD8$^+$ T cells from Cbl-b$^{-/-}$ TCR Tg mice behave similarly to non-TCR Tg Cbl-b$^{-/-}$ T cells. TCT Tg Cbl-b$^{-/-}$ mice reject inoculated tumors more efficiently than non-TCR transgenic Cbl-b$^{-/-}$ mice. This can be determined by subcutaneous injection of various numbers of E.G7 or B16 ($1\times10^4$-$10^6$) cells/mouse into Cbl-b$^{-/-}$ OT1 or Cbl-b$^{-/-}$ Pmel-1 Tg mice, respectively. Growth of the injected tumors can be monitored as described herein. C57BL/6, Cbl-b$^{-/-}$, wildtype OT1 or Pmel-1 Tg mice will be used as controls. It can also be determined whether CD8$^+$ T cells are involved in tumor rejection by examining the frequency and the activation status of tumor infiltrating CD8$^+$ T cells in the regressing tumor tissues by immunohistology and flow cytometry.

To quantitatively determine the efficiency of Cbl-b$^{-/-}$ TCR CD8$^+$ T cells in the eradication of established tumors, various numbers of Cbl-b$^{-/-}$ OT1 or Pmel-1 TCR Tg CD8$^+$ T cells can be transferred intravenously into the corresponding tumor-bearing mice and the kinetics of regression of the established tumors can be monitored. To establish tumor-bearing mouse models, wildtype C57BL/6 mice (n=5-10 mice/group) can be subcutaneously inoculated with 1-3$\times10^6$ E.G7 or B16 tumors cells. Tumors growth can be followed closely until size of the tumors reaches 5$\times$5 mm$^2$ in diameter. To examine the efficiency of tumor-specific Cbl-b$^{-/-}$ CD8$^+$ T cells in the anti-tumor responses, various numbers (ranging from about $1\times10^3$ to about $10^7$) of CD8$^+$ T cells from Cbl-b$^{-/-}$ OT1 or Cbl-b$^{-/-}$ Pmel-1 Tg mice can be transferred into the tumor-bearing mice. CD8$^+$ T cells from wild-type, Cbl-b$^{-/-}$, OT1 or Pmel-1 Tg mice will be respectively used as controls. CD8$^+$ T cells can be purified by MACS (Miltenyi Biotec). Following adoptive transfer of CD8$^+$ T cells, tumor size can be measured with a microcalipers on weekly basis and the rates of tumor growth can be documented as described. Mice can be sacrificed once the tumors size reach 20$\times$20 mm$^2$ or bigger.

Effective tumor rejection by Cbl-b$^{-/-}$ CD8$^+$ T cells could result from more efficient priming or enhanced effector function, or both. This is an important aspect in elucidating how Cbl-b$^{-/-}$ CD8$^+$ T cells reject tumor cells because it can determine which type of cells can be in clinical cancer therapy. To determine whether Cbl-b$^{-/-}$ tumor-specific CD8$^+$ T cells are more efficiently activated by tumors in vivo, in vivo priming and activation of Cbl-b$^{-/-}$ CD8$^+$ T cells can be monitored in tumor-bearing mice by a CFSE labeling approach (67). In certain embodiments, purified naïve Cbl-b$^{-/-}$ TCR Tg CD8$^+$ ($1\times10^6$) T cells can be labeled with CFSE in vitro and transferred into the corresponding tumor-bearing Rag2$^{-/-}$ mice by i.v. injection. Rag2$^{-/-}$ mice can be suitable as tumor recipients because they do not have any lymphocytes, so that the donor T cells can be easily identified. Additionally, using Rag2$^{-/-}$ mice as recipients can exclude the effect of any help from CD4$^+$ T cells because Rag2$^{-/-}$ mice do not have CD4$^+$ T cells. To determine the activation and proliferation of the transferred CD8$^+$ T cells, single cell suspension from tumor tissues by collagenase digestion can be prepared and CFSE intensity (a parameter for cell division) can be examined in donor CD8$^+$ T cells by flow cytometry. Activation status of the infiltrated CD8$^+$ T cells can be determined based on cell surface activation markers such as CD69, CD44, CD25, and CD62L by flow cytometry. Increase in cell division as well as the total numbers of cells that express the activation markers in Cbl-b$^{-/-}$ CD8$^+$ T cells compared to the measured numbers in wildtype cells can indicate that Cbl-b$^{-/-}$ mutation enhances the priming of CD8$^+$ T cells by the tumor cells.

Cbl-b$^{-/-}$ mutation augments the effector function of CTLs. In certain instances, adoptive transfer of the same numbers of in vitro activated Cbl-b$^{-/-}$ TCR Tg CD8$^+$ T cells can lead to more efficient eradication of the established tumors compared to eradication of tumors by activated wildtype TCR Tg CD8$^+$ T cells. In vitro activated CD8$^+$ T cells can be obtained by stimulating purified Cbl-b$^{-/-}$ and wildtype OT1 or Pmel-1 CD8$^+$ cells with either plate-bound anti-CD3 antibody or APCs plus Ova or gp100 peptide (100 μM) in the presence of IL-2. Additionally, to directly measure whether effector Cbl-b$^{-/-}$ CD8$^+$ T cells are more potent killers than wildtype CD8$^+$ T cells, the cytotoxicity of activated Cbl-b$^{-/-}$ OT1 and Pmel-1 Tg CD8$^+$ T cells can be compared with that of the wildtype TCR Tg CD8$^+$ cells using corresponding tumors cells as the targets using in vitro cytotoxicity assay.

To determine whether Cbl-b$^{-/-}$ CD8$^+$ T cells provide a long-term protection, and mount an efficient memory response against tumors, the recurrence of tumors in E.G7 and B16 tumor inoculated Cbl-b$^{-/-}$ mice can be monitored for extended period of time, for example but not limited to up to 1.5 year. In certain embodiments, presence of tumor-specific CD8$^+$ memory CD8$^+$ T cells in tumor-regressed Cbl-b$^{-/-}$ mice can be determined by challenging the mice with the same tumor and then comparing the kinetics of tumor growth. The frequency of tumor specific CD8$^+$ memory T cells in the tumor-regressed mice can be determined by in vitro cytotoxicity assay using the corresponding tumor cells as the targets.

A combined vaccination and IL-2 administration has been shown to enhance B16 tumor eradication by Pmel-1 TCR Tg mice after pmel-17 peptide vaccination (34). To determine the effect of this procedure for Cbl-b$^{-/-}$ Pmel-1 Tg CD8$^+$ T cells-mediated tumor rejection, B16 tumor-bearing mice can be vaccinated and treated with IL-2 (100,000 U/mouse, from N. P. Restifo) after the adoptive transfer of Cbl-b$^{-/-}$ Pmel-1 Tg and wildtype Pmel-1 Tg CD8$^+$ T cells, and tumor regression can be monitored. Result from this experiment can demonstrate that a combined treatment of vaccine, IL-2, and Cbl-b$^{-/-}$ tumor-specific CTLs have an additive effect on tumor rejection.

Cbl-b$^{-/-}$ mice mount an efficient response against: implanted strong antigenic tumor (E.G7), and low doses of weak antigenic tumors (EL4 and B16). Adoptive transfer of purified and/or isolated Cbl-b$^{-/-}$ CD8$^+$ T cells is sufficient to eradicate established tumors, for example established E.G7 tumor. In other aspects, Cbl-b$^{-/-}$ CD8$^+$ T cells are potent tumor killers. The efficiency of tumor eradication could be enhanced with increased ratios of tumor-specific CD8$^+$ T cells versus the target tumor cells. In certain instances, Cbl-b$^{-/-}$ OT1 or pmel-1 Tg CD8$^+$ mice produce much stronger anti-tumor responses because these mice possess significantly more tumor-specific CD8$^+$ T cells than Cbl-b$^{-/-}$ non-TCR Tg mice. Cbl-b$^{-/-}$ CD8$^+$ T cells are responsible for eliciting an anti-tumor response, and adoptive transfer of Cbl-b$^{-/-}$ OT1 Tg or Cbl-b$^{-/-}$ pmel-1 Tg CD8$^+$ T cells into the corresponding tumor-bearing mice can efficiently eradicate the established tumors. The maximal size and regression kinetics of tumor burden that can be eradicated by the adoptively transferred Cbl-b$^{-/-}$ OT1 Tg or Cbl-b$^{-/-}$ pmel-1

Tg CD8+ T cells can be determined. In other embodiments, the minimal numbers of adoptively transferred antigen-specific CD8+ T cells required for the tumor regression can be determined. Furthermore, it can be determined whether increased numbers of CD8+ T cells leads to more rapid regression of tumor burden.

It is possible that rejection of the low dose B16 tumor in Cbl-b$^{-/-}$ mice is mediated by CD8+ T cells that recognize other high affinity tumor antigen than gp100 which exhibits a low affinity to the Pmel-1 TCR. In certain embodiments, the adoptive transfer of the purified Cbl-b$^{-/-}$ Pmel-1 CD8+ T cells into B16 tumor bearing mice cannot elicit a strong anti-tumor response. In this case, B16 tumor bearing mice that receive either wildtype or Cbl-b$^{-/-}$ Pmel-1 CD8+ T cells can be immunized with a vaccine encoding a variant form of gp100 in the absence or presence of a high dose of IL-2. This variant gp100 provides a higher affinity epitope in the context of MHC H-2$^b$ to the Pmel-1 TCR, thus providing a better chance to activate Pmel-1 T cells. If the Cbl-b$^{-/-}$ mutation renders CD8+ T cells an advantage of activation by tumor cells over the wildtype T cells, mice that receive Cbl-b$^{-/-}$ T cells can reject B16 tumor more efficiently, even in the absence of IL-2 administration, than the mice that receive the wild-type cells.

In certain aspects, the invention provides methods to quantitatively assess the efficiency of Cbl-b$^{-/-}$ CD8+ T cells in the eradication of both strong and weak antigenic tumors. Contribution to the anti-tumor responses of wildtype CD4+ T cells and dendritic cells from the recipient mice cannot be excluded. To evaluate the role of CD4+ T cells and dendritic cells in Cbl-b$^{-/-}$ CD8+ T cell mediated tumor rejection, various numbers of wildtype or Cbl-b$^{-/-}$ CD4+ T cells can be cotransferred with Cbl-b$^{-/-}$ TCR Tg CD8+ T cell into tumor-bearing Rag2$^{-/-}$ mice, and growth of tumors can be monitored according. To assess the role of dendritic cells, conditional dendritic cell knock-out (CD11c-DTR) mice can be used as tumor-bearing host. Dendritic cells can be eliminated in these mice by diphtheria toxin (DT) injection right before the adoptive transfer of CD8+ T cells. If Cbl-b$^{-/-}$ CD4+ or Cbl-b$^{-/-}$ dendritic cells contribute to the anti-tumor response, certain embodiments of the methods for eliciting anti-tumor immune response can include dendritic cells in therapeutic adoptive transfer.

Autoimmune Consequence: Adoptive transfer of Cbl-b$^{-/-}$ CD8+ T cells could impose autoimmune consequence to the host. A risk of developing a severe autoimmune disease can be reduced by careful choice of the target antigen, or by transfer of mono- or oligo-clonal T cells that specifically recognize tumor antigens. For instance, Pmel-1 CD8+ T cells recognize gp100 peptide-H-2D$^b$ complex that is also expressed by normal melanocytes of the hosts. Adoptive transfer of Cbl-b$^{-/-}$ CD8+ T cells from Pmel-1 mice might results in the autoimmunity against normal host melanocytes, leading to vitiligo of melanocytes in the recipient mice, which is unlikely to be life-threatening. To evaluate the autoimmune consequence of the adoptive transfer of Pmel-1 CD8+ T cells, the correlation between the degree of vitiligo and efficiency of tumor eradication by simultaneously monitoring the depigmentation of recipient mice and tumor regression can be determined.

Cbl-b$^{-/-}$ CTLs can Eradicate Tumors that Prevent T Cell Response Through TGF-Beta or Tumor Barrier In certain aspects, the invention provides that Cbl-b$^{-/-}$ CD8+ T cells mount efficient immune responses against tumors that lack costimulatory signals. Since tumor cells may also prevent immune responses through other mechanisms, such as suppression by TGF-beta or prevention of T cell infiltration by tumor barriers, it can be determined whether Cbl-b$^{-/-}$ CD8+ T cells may overcome these negative regulatory mechanisms in tumor surveillance.

Adoptive Transfer of Cbl-b$^{-/-}$ CD8+ T Cells can Eradicate Tumors that Produce a High Level of TGF-Beta TGF-beta is a potent cytokine that suppresses T cell responses. It has been reported that tumor cells may escape immune surveillance by secreting TGF-beta directly or recruiting to tumor environment TGF-beta-producing immune cells such as CD4+ CD25+ regulatory T cells. Cbl-b$^{-/-}$ CD8+ T cells are resistant to TGF-beta mediated suppression. Cbl-b$^{-/-}$ T cells can eradicate tumors in the presence of a high level of TGF-beta.

To determine whether Cbl-b$^{-/-}$ CD8+ T cells mount immune response against tumors in the environment of TGF-beta such as TGF-beta producing tumor or presence of CD4+ CD25+ regulatory T cells, TRAMP-C2 cells can be used as a model. TRAMP-C2 is an early-passage murine prostate cancer cell line derived from TRAMP mice that spontaneously develops prostate cancer due to expression of prostate-specific simian virus (SV) 40 large T antigen. TRAMP-C2 cells produce spontaneously a high titer of TGF-beta both in in vitro culture and in transplanted mice. When transplanted into C57BL/6 mice by i.v. injection, 21 days after the transplantation mice develop multiple gross and microscopic pulmonary metastatic cancer, eventually leading to the death. TRAMP-C2 cells are resistant to activated tumor-specific CD8+ T cells in adoptive transfer experiment; however, they can be eliminated by tumor-specific CD8+ T cells that express a dominant negative form of TGF-beta type II receptor, indicating that T cells reject TRAMP-C2 tumor when TGF-beta signaling is impaired.

To determine whether Cbl-b$^{-/-}$ CD8+ T cells can respond to and eradicate TGF-beta-producing tumor, TRAMP-C2-specific CD8+ T cells can be generated. Adoptive transfer of these CD8+ T cells into TRAMP-C2-bearing mice can determine whether these TRAMP-C2-specific Cbl-b$^{-/-}$ CD8+ T cells can control lung metastasis of TRAMP-C2 cancer. Briefly, to generate TRAMP-C2-specific CD8+ T cells, Cbl-b$^{-/-}$ and wildtype C57BL/6 mice, both of which are CD45.2+, can be immunized with irradiated TRAMP-C2 cells (5×10$^6$/mouse) by subcutaneous injection every 14 days for total five immunizations. About two weeks later, CD8+ T cells can be purified from spleen of the immunized mice and stimulated with APCs, which are irradiated mouse splenic cells, loaded with TRAMP-C2 lysates (1×10$^6$ cells/ml). Cells can be cultured in the presence of IL-2 (50 U/ml) and anti-CD3 antibody (30 ng/ml), and culture media can be changed every 3 days. CD8+ cells can be expanded for 10 days before another round of stimulation. Titers of antigen-specific CD8+ in the final culture can be determined by in vitro cytotoxicity assay using TRAMP-C2 cells as target. To assess whether the activated TRAMP-C2-specific CD8+ T cells can eradicate the transplanted TRAMP-C2 cells, SJL (CD45.1+) mice can be challenged by i.v. administration with 5×10$^5$ TRAMP-C2 cells. About twenty days later, various numbers (1-10×10$^5$) of TRAMP-C2-specific Cbl-b$^{-/-}$ or wildtype CD8+ T cells can be adoptively transferred into the tumor bearing mice. Forty days after CD8+ T cell transfer, mice can be sacrificed, and lung from these mice can be collected for gross and histological examination. Infiltration of donor derived (CD45.2+) CD8+ T cells, as well as other recipient (CD45.1+) immune cells, can be identified by immunohistological analysis and quantified by flow cytometry. Apoptosis of tumor cells can be determined for example by TUNEL assay.

It has been shown that adoptive transfer of TGF-beta insensitive CD8+ T cells prevents pulmonary metastasis of TRAMP-C2 cancer. Prevention of the growth of TRAMP-2C tumor is a result of activation of TGF-beta insensitive CD8+ T cells that eradicate TRAMP-C2 cells by apoptosis. Cbl-b$^{-/-}$ CD8+ T cells are resistant to TGF-beta suppression. In certain aspects, the invention provides that adoptive transfer of TRAMP-C2 specific Cbl-b$^{-/-}$ CD8+ T cells can prevent metastasis of TRAMP-C2 cancer in the tumor-bearing mice. Immunohistological and flow cytometric analysis can reveal massive infiltration of Cbl-b$^{-/-}$ CD8+ T cells, as well as apoptosis of TRAMP-C2 cells in the lung. In contrast, adoptive transfer of wildtype CD8+ T cells cannot affect the progression of TRAMP-2C tumor. In certain embodiments, the invention provides methods to determine whether the transferred Cbl-b$^{-/-}$ CD8+ T cells provide long-term protection. Recurrence of TRAMP-2C tumor can be monitored in tumor-regressed mice for the rest of their life.

It is possible that the immunization scheme to generate TRAMP-C2 specific CTLs might produce Cbl-b$^{-/-}$ CD8+ T cells with a broad spectrum of specificity against self-antigens. As a consequence, adoptive transfer of these CD8+ T cells might cause a severe autoimmune disease. In certain embodiments, a modified protocol can be used to generate Cbl-b$^{-/-}$ CD8+ T cells that recognize only TRAMP-C2 specific antigen, or SV40 large T antigen. Splenic CD8+ T cells from TRAMP-C2 immunized Cbl-b$^{-/-}$ mice stimulate and expand in vitro with APCs loaded with SV40 large T peptides or protein, instead of the TRAMP-C2 cell lysate. This approach can generate a CD8+ CTL population that recognizes SV40 large T antigen in the context of MHC H-2$^b$. To ensure that the obtained CD8+ T cells are specific to TRAMP-2C cells, in vitro cytotoxicity of these cells against TRAMP-2C and other H-2$^b$ target cells that do not express SV40 large T antigen can be examined. Specific killing of TRAMP-2C cells but not the control cells suggests that the obtained CTLs are predominantly specific to SV40 large T antigen in the context of MHC H-2$^b$.

If TRAMP-2C tumors are not rejected by the transferred Cbl-b$^{-/-}$ CD8+ T cells, there are two possible explanations to be considered before a conclusion that Cbl-b$^{-/-}$ CD8+ T cells cannot overcome suppression by tumor-derived TGF-bets. First, it can be determined whether the failed tumor rejection is due to that insufficient numbers of tumor specific CD8+ T cells are used in the transfer experiment. In certain embodiments, up to 10 times more (1-5×10$^7$) CD8+ T cells can be transferred into the tumor-bearing mice and then tumor regression can be monitored. In previous work showing that TRAMP-2C cells are rejected by TGF-beta insensitive CD8+ T cells, the TGF-beta-insensitive CD8+ T cells used in the experiment are TRAMP-2C-specific CTLs that overexpress a dominant negative form of TGF-beta II receptor. It is possible that this dominant negative form of TGF-beta II receptor may exert other unknown effects on CD8+ T cells in addition to the TGF-beta insensitivity. To determine that, this TGF-beta receptor mutant can be over-expressed in TRAMP-2C-specific Cbl-b$^{-/-}$ CD8+ T cells, and these cells can be examined to determine whether they can reject TRAMP-2C tumor. Rejection of TRAMP-2C tumor by these transfectants is indicative that other alterations caused by the TGF-beta receptor expression, perhaps together with TGF-beta insensitivity, are responsible for the prevention of the TRAMP-2C metastasis.

Cbl-b$^{-/-}$ CD8+ T Cells can Eradicate Tumors Protected by Tumor Barrier

Murine models have shown that abundant, activated, tumor antigen-specific CTLs often fail to eradicate large solid tumors even when they can efficiently reject skin graft or less established tumors expressing the same antigens. Clinically, it has been documented that presence of high numbers of circulating tumor-specific CD8+ T cells is not correlated with T cell infiltration into the parenchyma of tumors and tumor regression. Studies indicate that tumor barriers composed of host infiltrating stroma may be one of the reasons that prevent efficient T cell priming and expansion both in lymphoid tissues and at tumor sites. Evidence to support this idea stems from the experiment in which recruitment of CD8+ T cells into tumor tissues by enforced expression of LIGHT/TNF SF-14, a member of the TNF family that induce expression of chemokine such as CCL21 in stromal barrier, results in tumor rejection. In certain aspects, the invention provides that Cbl-b$^{-/-}$ CD8+ T cells reject established E.G7 tumors. In other aspects, the invention provides that Cbl-b$^{-/-}$ CD8+ T cells can reject tumors that are protected by tumor barrier. This provides insight into the mechanisms by which Cbl-b$^{-/-}$ CD8+ T cells mount anti-tumor responses and shows that Cbl-b$^{-/-}$ CD8+ T cells can be used to treat large established tumors.

The Ag104 fibrosarcoma expressing murine H-2L$^d$ (Ag104L$^d$) is highly tumorigenic, with 100% outgrowth in C3H×C57BL/6 F1 (C3B6F1) mice after subcutaneous injection of 10$^4$ cells. The tumor-bearing mice usually die in 3-4 weeks after the inoculation. Transfer of 2C TCR Tg CD8+ T cells which recognize H-2L$^d$ cannot reject Ag104L$^d$ tumor due to lack of T cell infiltration through the tumor barrier. To determine whether Cbl-b$^{-/-}$ CD8+ T cells may circumvent Ag104L$^d$ tumor barrier, Cbl-b$^{-/-}$ mice can be crossed to 2C TCR Tg mice to generate Cbl-b$^{-/-}$ 2C TCR Tg mice. CD8+ T cells can be purified from Cbl-b$^{-/-}$ 2C TCR Tg and wild-type 2C TCR Tg mice, respectively, and these cells can be transferred into Ag104L$^d$ tumor-bearing mice by i.v. injection, and tumor regression monitored. Ag104L$^d$ tumor-bearing mice with tumor parenchyma can be obtained by subcutaneously inoculating 10$^4$ Ag104L$^d$ cells into C3B6F1 mice one week before T cell transfer. To directly examine whether Cbl-b$^{-/-}$ CD8+ T cells can infiltrate into and expand inside tumor tissue, the purified CD8+ T cells can be labeled by CFSE, the labeled cells transferred into Ag104L$^d$ tumor-bearing mice by i.v. injection, and the recipient mice then sacrificed at different time points (12, 24, 48, and 72 hours later) after the transfer. Infiltrating T cells in the tumor tissues can be quantified by histology and flow cytometry. Activation status of the infiltrated cells can be determined by flow cytometry based on the expression of cell surface activation markers such as CD44 and CD62L. To determine whether T cell activation status is correlated to the efficiency of infiltration, purified CD8+ T cells will be activated in vitro by anti-CD3 and anti-CD28 antibodies and cultured for 2-3 days in the presence of IL-2 (50 U/ml) before being subjected for CF SE labeling and the transfer. Apoptosis of Ag104L$^d$ cells in tumor tissue will be determined by a TUNEL assay. To control for the specificity of the CD8+ T cell infiltration, the infiltration of the transferred CD8+ T cells in other tissue, including lung, kidney, and liver can be examined by immunohistological analysis.

Ag104L$^d$ tumors are protected from immune system by tumor barrier. If adoptive transfer of Cbl-b$^{-/-}$ 2C TCR Tg CD8+ T cells eradicates established Ag104Ld tumor, this indicates that Cbl-b$^{-/-}$ CD8+ T cells can circumvent tumor barrier to elicit anti-tumor response. In certain embodiments, CFSE-labeled Cbl-b$^{-/-}$ 2C TCR Tg CD8+ T cells infiltrate and expand in tumor tissue, wherein CD8+ T cells are present at minimal levels and not expand in lung, kidney, and liver, and wildtype 2C TCR Tg CD8$^+$ T cells are excluded from tumor tissue. TUNEL analysis can reveal apoptosis of Ag104L$^d$ cells in tumor tissue from the mice that receive the Cbl-b$^{-/-}$ CD8$^+$ T cells, but not in mice that receive wildtype CD8$^+$ T cells.

It is possible that Cbl-b$^{-/-}$ CD8$^+$ T cells cannot reject established tumor Ag104L$^d$ tumor. This can be a result of either the failure of penetrating tumor barrier or inability of reacting to tumor stimulation. The first possibility can be verified by directly monitoring CF SE-labeled CD8$^+$ T cell infiltration in tumor tissue after the transfer. To examine the second possibility, the activation status and proliferation of tumor-infiltrating CD8$^+$ cells can be analyzed by flow cytometry. To assess whether the infiltrating CD8$^+$ T cells are functionally competent, the tumor-infiltrating CD8$^+$ T cells can be isolate by FACS sorting and then analyzed for cytotoxicity against Ag104Ld cells by an in vitro cytotoxicity assay.

In embodiments where Cbl-b$^{-/-}$ CD8$^+$ T cells can penetrate tumor barrier, the invention provides methods to determine the mechanisms that allow Cbl-b$^{-/-}$ T cells to circumvent the barrier. Since migration of T cells through tumor parenchyma is regulated by chemokines and cell adhesion molecules, it can be determined whether the Cbl-b$^{-/-}$ mutation alters the chemotaxis and adhesion of CD8$^+$ T cells.

Ablation of Cbl-b in Tumor-Infiltrating CTLs Restores their Killing Activity Against the Target Tumors Tumor burden often contains large numbers of CTL infiltrates. These CTLs recognize a broad spectrum of tumor-associated epitopes. Under normal situation, these infiltrating CTLs exist in a functional anergic state, as they rarely result in tumor eradication. Evidence suggests that the lack of costimulation signals from tumor cells attenuates or even anergizes the effector function of the CTLs. Cbl-b$^{-/-}$ T cells are resistant to anergy induction. Ablation of Cbl-b activity in tumor-infiltrating CTLs can convert Cbl-b deficient cells into "super killer" T cells that respond to a repertoire of diverse tumor-associated antigens independent of costimulatory signals. In certain embodiments, the activity of Cbl-b is reduced or eliminated by ablation of Cbl-b expression in tumor-infiltrating CTLs. In certain embodiments, Cbl-b expression is reduced by use of small interference RNA (siRNA). In other embodiments, Cbl-b expression is reduced by use of dominant negative Cbl-b variant, by administration of an agent which inhibits the activity of Cbl-b, or by deletion of Cbl-b at its genomic locus. Cbl-b ablated cells are relieved from their anergic state, and are responsive to tumors, and tumor antigens.

Adoptive transfer of Cbl-b siRNA-expressing tumor-infiltrating CTLs can result in eradication of the established tumors. Tumor-infiltrating CTLs are suitable for use in the adoptive transfer methods because these cells are enriched for tumor specific CD8$^+$ T cells, thus limiting the risk of autoimmune response that may associate with the transfer of T cells with a diverse TCR repertoire. In certain aspects, the invention provides methods to engineer "super killer" CTLs for clinic tumor therapy.

Ablation of Cbl-b in Tumor-Infiltrating CTLs by siRNA Abolishes their Anergic State to Antigen Stimulation The siRNA approach has been successfully used to knockdown or completely silence the expression of actively transcribed genes in primary lymphocytes in mice (68). In certain embodiments, Cbl-b expression in CTLs can be knockdown using siRNA approach. Four siRNA oligonucleotides, including the inhibitory RNA of SEQ ID NO: 1 (5'-CAGGAGTATGAGACAGAAG-3'), were synthesized and cloned respectively into a retroviral vector that contains a human CD2 gene (hCD2) as a reporter. In this vector, the expression of siRNA is driven by a RNA polymerase III (H1) promoter (69). To assess the efficiency of blocking Cbl-b expression by different siRNA, 10 μg of siRNA-expression vector DNA containing different Cbl-b siRNA oligonucleotides and 1 μg of Cbl-b-expressing vector DNA were co-transfected into 293T cells by Ca$^{++}$ precipitation. 48 hours later, the levels of Cbl-b expression in each transfected cell samples were determined by a Western blot analysis. Expression of one siRNA oligonucleotide, termed as siRNA 1, led to more than 95% of inhibition of Cbl-b expression. This result thus demonstrated that Cbl-b expression can be ablated by siRNA approach.

Vectors expressing siRNA directed to Cbl-b can be introduced and expressed into tumor-specific CTLs by retrovirus-mediated gene transfer. A step in this process is infecting in vitro cultured CTLs with a high efficiency. In certain embodiments, large numbers of virus-infected T cells in vitro can be generated by stimulation of primary T cells with plate-bound anti-CD3 (5 μg/ml) and soluble anti-CD28 (5 μg/ml) antibodies in the presence of IL-2 (50 U/ml) for 48 hours. Activated cells can be infected with a hCD2-based siRNA retroviral vector. Virus infected cells can be cultured for additional 5-10 days in the presence of IL-2. The efficiency of viral infection is determined by FACS based on the expression of cell surface hCD2. The method typically yields 30-50% of virus-infected (hCD2$^+$) T cells, wherein siRNA can be introduced into cultured CTLs to reduce the expression of a target gene, such as Cbl-b.

Ablation of Cbl-b in Tumor-Infiltrating CTLs Enhances their Responsiveness to Tumor-Antigen Stimulation It has been shown that both E.G7 and B16 tumor tissues contain substantial numbers of infiltrating CTLs. These CTLs are in an anergic state because they are unable to reject the tumors. To determine whether ablation of Cbl-b can render these tumor infiltrating CTLs responsive to tumor-antigen stimulation, CTLs can be isolated from the E.G7 or B16 tumor burden (17, 30). OT1 or Pmel-1 Tg mice can be inoculated subcutaneously with E.G7 or B16 tumors (1-3×10$^6$/mouse), respectively. OT1 and Pmel-1 Tg mice are suitable because they can have abundant tumor-specific CD8$^+$ T cells. Tumor tissue (when tumors reach to the sizes of 5-10 mm in diameter) can be surgically removed and cut into small pieces (2-3 mm in diameter) and treated with collagenase at 37° C. Dead cells can be removed by Ficoll gradient centrifugation. Tumor-infiltrating CTLs can be isolated by MACS enrichment protocol using antibodies against OT1 (Vβ8$^+$) or Pmel-1 (Vβ13$^+$) T cells. To ablate Cbl-b in the CTLs, purified T cells can be activated in vitro by anti-CD3 and anti-CD28 antibody costimulation in the presence of IL-2 (30 U/ml). 48 hours later, activated T cells can be infected with Cbl-b siRNA-expressing retroviral vector as described herein. Virus infected cells can be cultured for additional 5-10 days in the presence of IL-2. The efficiency of virus infection is be determined by FACS analysis. To determine the efficiency of ablation of Cbl-b by the siRNA in CTLs, Cbl-b siRNA-infected (hCD2$^+$) CTLs can be purified by MACS after staining the cells with anti-human CD2 antibody. The levels of Cbl-b protein in hCD2+ cells can be compared with that in wildtype cells (hCD2$^-$) by Western blot analysis.

To determine whether Cbl-b siRNA-expressing CTLs functionally resemble Cbl-b$^{-/-}$ CD8$^+$ T cells, retrovirus-infected (hCD2$^+$) and non-infected (hCD2$^-$) CTLs can be stimulated with different doses of plate-bound anti-CD3 antibody or a combination of anti-CD3 and anti-CD28 antibodies as described herein. The rates of cell proliferation can be determined by analyzing CSFE labeled cells or $^3$H-thymidine incorporation assay. The levels of cytokines such as IL-2 and IFN-gamma produced by the activated CTLs can be determined by an ELISA or by intracellular staining followed by FACS analysis. Resistance of hCD2$^+$ T cells to TGF-beta suppression can be examined as described herein. To quantitatively determine whether ablation of Cbl-b by siRNA enhances the killing activity of CTLs, an in vitro cytotoxicity assay can perform, using $^{51}$Cr-labeled corresponding E.G7 and B16 cells as the targets (71).

It is expected that Cbl-b siRNA-retrovirus infected (hCD2$^+$) CTLs will exhibit reduced expression of Cbl-b. Cbl-b siRNA-expressing CD8$^+$ T cells are expected to proliferate more vigorously and produce higher levels of IL-2 and IFN-gamma upon anti-CD3 stimulation than empty retroviral vector-infected or wildtype (hCD2$^-$) CTLs do, since ablation of Cbl-b will abolish the requirement of costimulation and lower the threshold of TCR signaling for activation. Additionally, the proliferation and IFN-gamma production by Cbl-b siRNA-expressing CD8$^+$ T cells will not be suppressed by TGF-beta and the cytotoxic activity of the Cbl-b siRNA-expressing CTLs should also be significantly enhanced. Further examination can include whether these Cbl-b-ablated CTLs can efficiently eradicate the established tumors.

This approach relies on the efficiently knockdown the endogenous Cbl-b in tumor-specific CTLs. A Cbl-b siRNA oligonucleotide of SEQ ID NO: 1 allows more than 95% inhibition of Cbl-b proteins in 293T cells. The expression of this siRNA in CTLs should efficiently ablate the endogenous Cbl-b. If the efficiency of Cbl-b ablation is less than 30-39%, 40-49%, 50-60% of inhibition, in CTLs by this siRNA, additional siRNA oligonucleotides can be designed and tested to identify siRNAs that would silence the expression of Cbl-b gene more efficiently in T cells. Currently, statistics shows that in mammalian systems approximately 25% of selected target siRNA sequences are functional (72). Thus, one or more siRNA sequences that may knockdown Cbl-b expression efficiently (more than 90%) can be identified when more siRNA sequences are tested. Functional assays, including but not limited to CD28 independent proliferation, IL-2 and IFN-gamma production, and TGF-beta insensitive suppression, can be used as markers to assess whether CD8$^+$ T cells expressing a particular siRNA can functionally mimic Cbl-b$^{-/-}$ CTLs. Since siRNA approach has been used to knockdown the expression of many genes in T cells and in mice, ablation of the expression of Cbl-b in CTLs can be accomplished by this approach.

An alternative approach that can be used to reduce Cbl-b function, is the expression of a dominant negative form of Cbl-b in CD8$^+$ T cells by retroviral transduction. A number of different Cbl-b protein variants, including mutations in tyrosine binding, ring finger (RF) and proline-rich domain, and several C-terminal tyrosine residues, can be made and tested to determine whether these protein variant create mutations that block Cbl-b function in T cells. Other Cbl-b protein variants can be made and tested to identify other dominant negative mutants of Cbl-b. Such dominant negative mutants of Cbl-b can be used to ablate Cbl-b function.

Adoptive Transfer of Cbl-b siRNA-Expressing Tumor-Infiltrating CTLs Eradicates Established Tumor.

Cbl-b$^{-/-}$ T cells may elicit an efficient anti-tumor immune response. Because tumor infiltrates isolated from tumor tissues are enriched for CTLs that have a broad spectrum of specificity against tumor antigens, inactivation of Cbl-b in these CTLs by Cbl-b siRNA provides a suitable approach to generate Cbl-b$^{-/-}$ tumor-specific CTLs in vitro. In certain embodiments, the invention provides that adoptive transfer of Cbl-b ablated tumor-infiltrating CTLs results in eradication of the established tumors. A method of adoptive transfer of Cbl-b ablated tumor-infiltrating CTLs can be used as a therapeutic tool to treat cancers in humans.

In non-limiting examples, tumor-infiltrating CTLs can be isolated from either OT1 or Pmel-1 Tg mice according to published protocols (17, 30), and Cbl-b can be ablated in these cells by siRNA using a retroviral vector as described herein. The TCR Tg mice are chosen because they have a high frequency of tumor-specific CD8$^+$ T cells. To determine whether Cbl-b-ablated tumor-specific CTLs may eradicate the established tumors, 1-10×10$^6$ Cbl-b siRNA-expressing CTLs isolated from either OT1 or Pmel-1 Tg mice, respectively, can be transferred into C57BL/6 mice that bear the corresponding established tumors, and then monitor the sizes of tumors. To determine whether the transferred CTLs can expand in vivo, the proliferation of the transferred cells can be examined by CSFE labeling assay. Infiltration of CTLs in tumor tissue can be determined by immunohistologic assay.

In non-transgenic mice, tumor-infiltrates can be enriched for tumor-specific CTLs. CTLs from these tumor burden should closely resemble that from human cancer tissues. To determine whether CTLs isolated from tumor tissues from wildtype tumor-bearing mice can be converted into the "super killer" CTLs against the corresponding tumors, CTLs can be isolated from tumor tissues of E.G7 or B16 tumor-bearing C57BL/6 mice by collagenase digestion, and FACS sorting. In certain embodiments, these cells can be expanded in vitro in the presence of IL-2 (50 U/ml), soluble anti-CD3 antibody and APCs (irradiated splenic cells) loaded with E.G7 or B16 lysate (10$^6$ cells/ml). Media can be changed every 10 days. This protocol has been shown to produce high numbers of anti-tumor specific CTLs (Ramarathinam et al., 1994). To ablate Cbl-b in these CTLs, for example by siRNA, these CTLs can be infected with Cbl-b siRNA expressing retroviral. Virus-infected cells can be purified by MACS after staining the cells with anti-hCD2. To test whether these cells can reject established tumor, Cbl-b ablated CTLs can be transferred (1-10×10$^6$ cells/mouse) into C57BL/6 mice that bear the corresponding tumors. Size and regression of the established tumors can be monitored as described herein.

To determine whether the tumor regression has lasting memory, tumor recurrence can be monitored for at least 1.5 years in those mice in which the tumor regressed. To determine whether the transferred CTLs develop into memory T cells, various doses of the same tumor cells can be reinoculated into the tumor regressed mice at different time points after the tumor regression, and then monitor tumor grow in the recipient mouse Wildtype mice can be inoculated with the same tumor as controls. To determine the frequency of tumor specific memory CTLs in tumor regressed mice, in vitro cytotoxicity assay can be performed using E.G7 and Pmel-1 cells as targets, respectively.

Various lines of evidence suggest that clinic tumors may prevent immune surveillance through TGF-beta and tumor barrier. In certain embodiments, the invention provides methods to determine whether TRAMP-2C and Ag104L$^d$ tumor-specific Cbl-b$^{-/-}$ CD8$^+$ T cells may circumvent these negative effects and mount an efficient anti-tumor response. Clinically, Cbl-b$^{-/-}$ T cells can be obtained by manipulation of mature CD8$^+$ T cells. Therefore, it can be determined whether Cbl-b siRNA-expressing CTLs can be used to eradicate TRAMP-2C and Ag104L$^d$ tumors in mice. TRAMP-2C reactive wildtype CD8$^+$ T cells from wildtype mice can be obtained by a repetitive immunization and in vitro stimulation approach as described herein. Ag104L$^d$ tumor reactive CD8$^+$ T cells can be obtained from Ag104Ld tumor-bearing mice according to a previous published protocols. In this protocol, Ag104L$^d$ tumor-bearing mice can be generated by subcutaneously injection of 106 Ag104L$^d$ into C57BL/6 mice. Two weeks later, soluble LIHGT (Yu, P. et al., 2004) can be injected into the Ag104L$^d$ tumor. This treatment has been shown to induce massive infiltration and expansion of Ag104L$^d$-specific CD8$^+$ T cells at the tumor site, which can be purified by flow cytometry and expanded in vitro by repetitive stimulation and IL-2 culture. When TRAMP-2C and Ag104L$^d$ tumor-reactive CD8+ T cells are obtained, Cbl-b activity can be knocked down in these cells, for example but not limited to by infection with Cbl-b siRNA retroviral vector. The ability and the efficiency of these cells to reject TGF-beta producing tumor or to penetrate tumor barrier can be determined according to the experimental design and methods as described herein.

Different Cbl-b siRNA-expressing CTLs can exhibit different degrees of anti-tumor activities. As a consequence, tumor specific CTLs expressing different Cbl-b siRNA may eradicate tumor with different efficiency. This can indicate that the same approach can be applied to human cancer therapy, using Cbl-b siRNA that can ablate Cbl-b expression in human T cells. Because Cbl-b$^{-/-}$ CTLs are resistant to TGF-beta suppression and adoptive transfer of Cbl-b$^{-/-}$ CD8$^+$ T cells rejects established E.G7 tumor, ablation of Cbl-b by siRNA in wildtype tumor-infiltrating CTLs can render these Cbl-b knock-down CTL cells capable of eradicating TRAMP-2C and Ag104L$^d$ tumor. This can also determine the profile of tumors that can be treated by Cbl-b ablated CTLs.

If expression of one particular siRNA in CTLs abolishes CD28 dependence for T cell activation, however fails to enhance tumor eradication, it can suggest that the frequency of tumor-specific CTLs in the adoptively transferred cells is important for an efficient tumor eradication. The frequencies of tumor-specific CTLs in tumor-infiltrating cells from wildtype mice can be determined by a limiting dilution assay using $^{51}$Cr-labeled tumor cells as the target (71). If tumor-specific CTLs in the transferred tumor-infiltrating T cells from wildtype mice are indeed lower as compared to that from the TCR Tg mice, it can be tested whether adoptive transfer of the increased numbers of CTLs from wildtype mice results in more efficient tumor rejection. If adoptive transfer of TCR Tg mouse-derived Cbl-b siRNA-expressing CTLs also fails to eradicate the established tumors, this can suggest that this particular siRNA might also knock-down the expression of other molecule(s), in addition to Cbl-b, that are critical for CTL to execute the anti-tumor function. A different Cbl-b siRNA sequence can be used to knock-down Cbl-b expression, because it is statistically unlikely that two different siRNA sequences cross suppress the expression of the same set of molecule(s).

Adoptive transfer of Cbl-b-ablated CD8$^+$ T cells from tumor infiltrates of wildtype mice might cause autoimmune disease if these CD8$^+$ T cells express a diverse TCR repertoire. This problem can be overcome by selectively expanding tumor specific CTL in vitro through repetitive stimulation of the tumor-specific CTLs with tumor specific antigen or antigens such as gp100 that are shared by tumor and less important cells.

Identification of Dominant Negative Form(s) of Cbl-b Using Mutagenesis Approach can Provide an Alternative Approach to Inhibit Cbl-b Function in CTLs.

In certain aspects, the function of Cbl-b ubiquitin ligase in CD28-dependent T cell activation and tumor rejection can be dissected. CD28 costimulatory signal is linked to PI-3 kinase and Vav signaling pathways (55, 56, 73). Both p85 of PI-3 kinase and Vav are ubiquitinated by Cbl-b, suggesting that Cbl-b regulates CD28 costimulatory signal through promoting ubiquitination of p85 and Vav (73, 74). Since the ubiquitin ligase function of Cbl-b is dependent on its RF-domain (75), it is likely that disruption of this domain can result in loss of CD28 dependence and sensitivity to TGF-beta suppression, and render T-cell responsiveness against tumors in the absence of the costimulation. In certain embodiments, the invention provides methods to determine whether expression of a RF-domain mutant Cbl-b in T cells permits T-cell activation independent of CD28 costimulation and TGF-beta suppression. Certain embodiments also provide methods to determine whether CTLs expressing a RF-domain mutant Cbl-b can mount immune responses against various tumors as Cbl-b$^{-/-}$ CTLs do. Results from this analysis can provide information for small compound drug design and screening that can benefit tumor immunotherapy. Since introduction of the Cbl-b$^{-/-}$ mutation into ATM$^{-/-}$ mice markedly diminishes the incidence of spontaneous tumors, and Cbl-b$^{-/-}$ mice do not develop spontaneous autoimmune disease, it is likely that a systemic suppression of Cbl-b function using such a compound can benefit tumor prevention.

Determining Whether Cbl-b's Ubiquitin Ligase Activity is Required for CD28 Dependent T Cell Activation The ubiquitin ligase activity of Cbl-b depends on the association of its RF domain with an E2 ubiquitin-conjugating enzyme. To inactivate the ubiquitination function of Cbl-b, mutant forms of Cbl-b can be generated in which mutants either the entire RF domain is deleted, or the key residues in the RF domain are substituted either alone or in combination to ensure elimination of the ubiquitin ligase activity. Since most of the available information on structure and ligase function of Cbl proteins come from the human c-Cbl, this information may serve as guidance for mutagenesis of murine Cbl-b. A mutant Cbl-b can be created which has the entire RF domain deleted, from amino acid 273 to amino acid 312 of murine Cbl-b (50). This mutant Cbl-b will be cloned into a bi-cistronic retroviral vector (70), its ubiquitination function and association with the known Cbl-b-binding molecules will be tested in the cultured T cells. If this mutation affects normal association of Cbl-b with other signaling molecules, point mutations such as Cbl-b(C376A), Cbl-b(W400A) and Cbl-b(C376A, W400A) can be generated by PCR-assisted mutagenesis. c-Cbl and Cbl-b share 98% sequence homology in their RF domains. Cbl-b(C376A) contains a mutation that replaces a key zinc-binding residue (cysteine 376) with an alanine. The equivalent mutation in human c-Cbl disrupts the formation of zinc-chelating loops that accommodate the most significant contact with UbcH7(75). For Cbl-b(W400A) (tryptophan 400 to alanine) mutation, the equivalent mutation in human c-Cbl maintains the zinc-binding capacity but poorly interacts with E2 ubiquitin-conjugating enzymes (76). For the mutant (Cbl-b(C376A) and (W400A)), a human c-Cbl equivalent has been shown to abolish its ubiquitin ligase activity completely both in vitro and in vivo (77). A FLAG tag can also be added to the C-termini of these mutants to allow specific detection. The mutant cDNA can be cloned into a bi-cistronic retroviral vector and their ubiquitination function and association with known signaling components, such as Zap70, Vav, and p85(78), can be tested first in cultured Cbl-b$^{-/-}$ T cells. Using this retroviral approach, activated primary T cells can be infected in vitro with more than 30-50% of efficiency.

Figure 14:
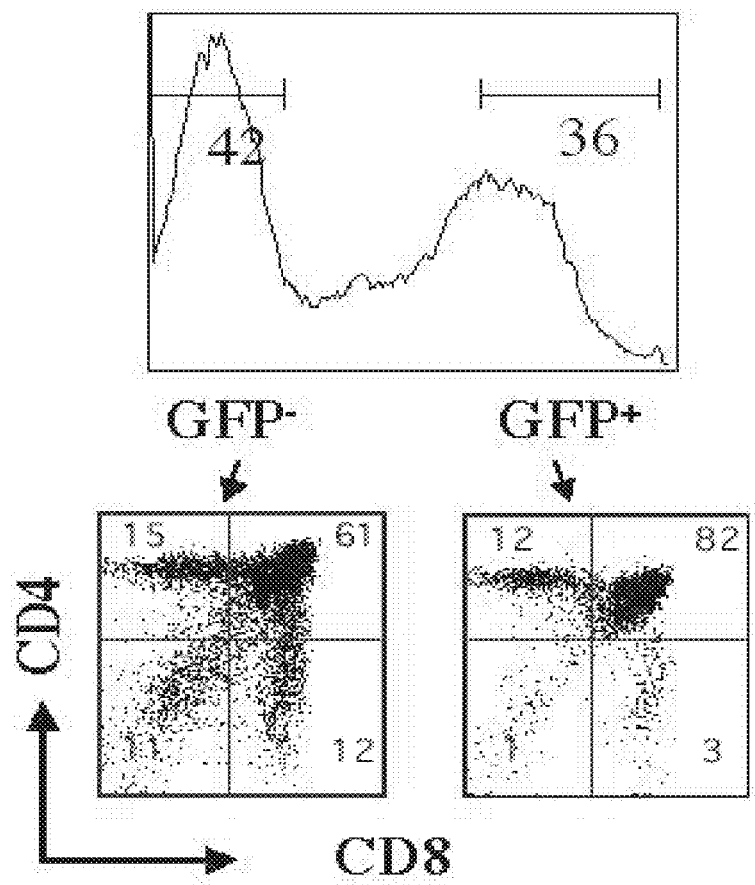
FIG. 14 shows restoration of the ratio of CD8$^+$ to CD4$^+$ T cells in c-Cbl and Cbl-b double knockout (c-Cbl Cbl-b dKO) thymocytes expressing a wildtype c-Cbl transgene. c-Cbl Cbl-b dKO thymocytes exhibited an increase in CD8$^+$ lineage cells (GFP$^-$ cells). To introduce a wildtype c-Cbl into hematopoietic stem cells, we cultured 5-FU-treated c-Cbl Cbl-b dKO BM cells for two days in the presence of mouse stem-cell factor (50 ng/ml), IL-3 (20 ng/ml) and IL-6 (50 ng/ml). Meanwhile, viral supernatants were prepared, and the cultured hematopoietic stem cells were infected according to a published protocol (70). Virus infected-stem cells (Ly9.1$^+$) were then transferred into the Rag2$^{-/-}$ (Ly9.1$^-$) mice to generate c-Cbl Cbl-b dKO Rag2$^{-/-}$ BM chimeras. One month later, development of the donor-derived thymocytes was assessed (Ly9.1$^+$) in the BM chimeras by FACS. Shown are gated Ly9.1$^+$ (donor-derived) cells. GFP$^-$ (dKO) and GFP$^+$ (transgenic c-Cbl-expressing) cells ware then gated and displayed, respectively, as dot-plots of the CD4 and CD8 staining. Percentages of each population are indicated. About 20-40% of retroviral-infected transgene-expressing thymocytes (GFP$^+$) can be obtained by this approach (Table 1). The transgene (WT c-Cbl)-expressing (GFP$^+$) thymocytes exhibited a normal ratio of CD4$^+$ to CD8$^+$ lineage cells with a consistent reproducibility (see Table 1), indicating that expression of a transgenic wildtype c-Cbl fully restored the ratio of CD4+ to CD8+ thymocytes.
Figure 15:
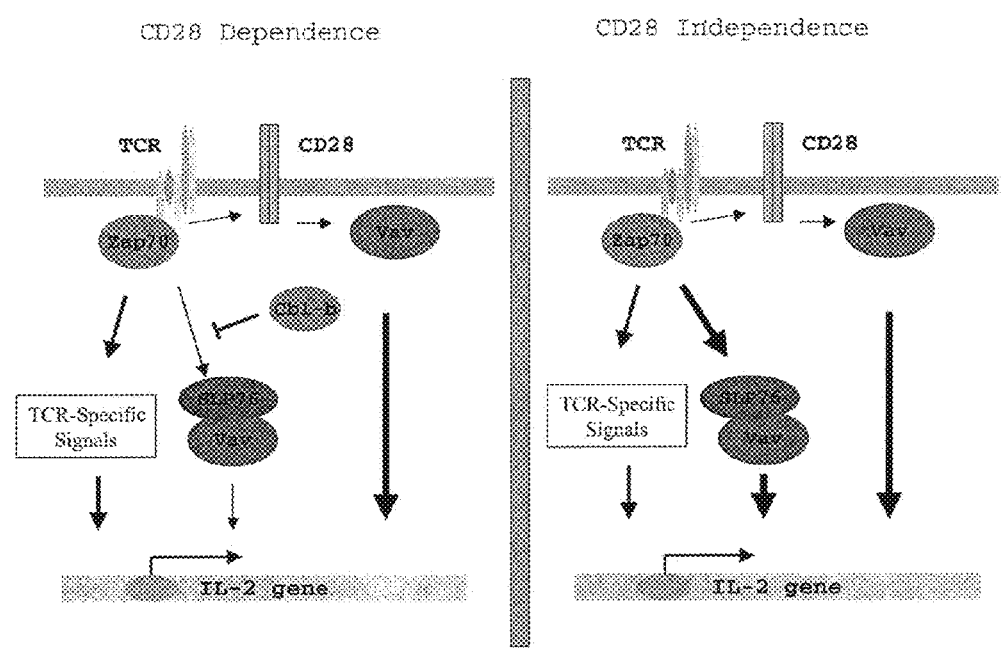
FIG. 15 shows hypothetic mechanisms of CD28 dependence of T cell activation. Activation of T cells, such as cell proliferation and IL-2 secretion, requires TCR specific signaling as well as costimulatory signaling mediated by CD28, the later mainly through Vav signaling pathway. Cbl-b may suppress specifically TCR-induced but not CD28-induced Vav activation. In the presence of Cbl-b, costimulation of CD28 is necessary to activate sufficient amount of Vav for T cell response, thus establishing CD28 dependence of T cell activation. However, in the absence of Cbl-b, CD28 costimulation is no longer needed because TCR stimulation alone can induce sufficient amount of Vav activity.
Figure 16A:
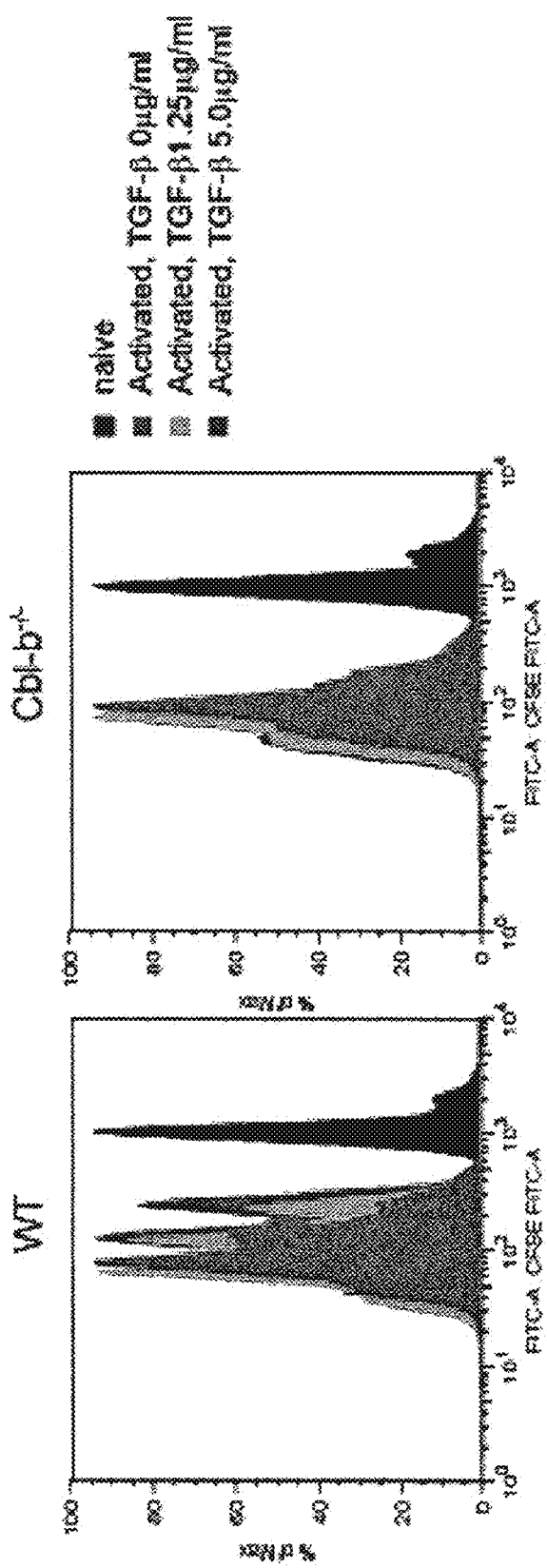
FIGS. 16A-16C show resistance of Cbl-b−/− CD8+ T cells to TGF-beta suppression. CD8+ T cells were purified using a CD8-enrichment column. Cells were then labeled with CFSE, stimulated with plate-bound anti-CD3 in the presence or absence of 5 ug/ml TGF-beta.
Figure 16B:
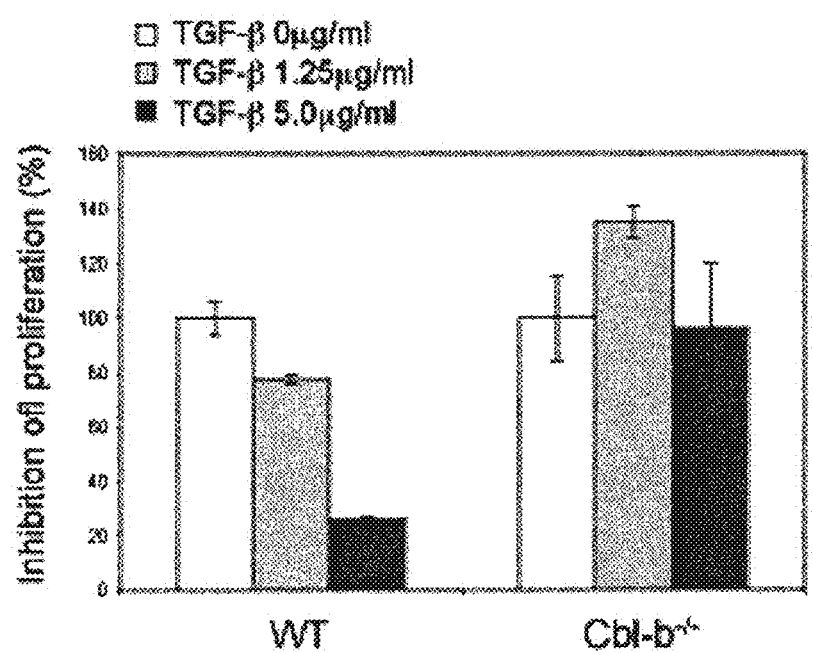
Figure 16C:
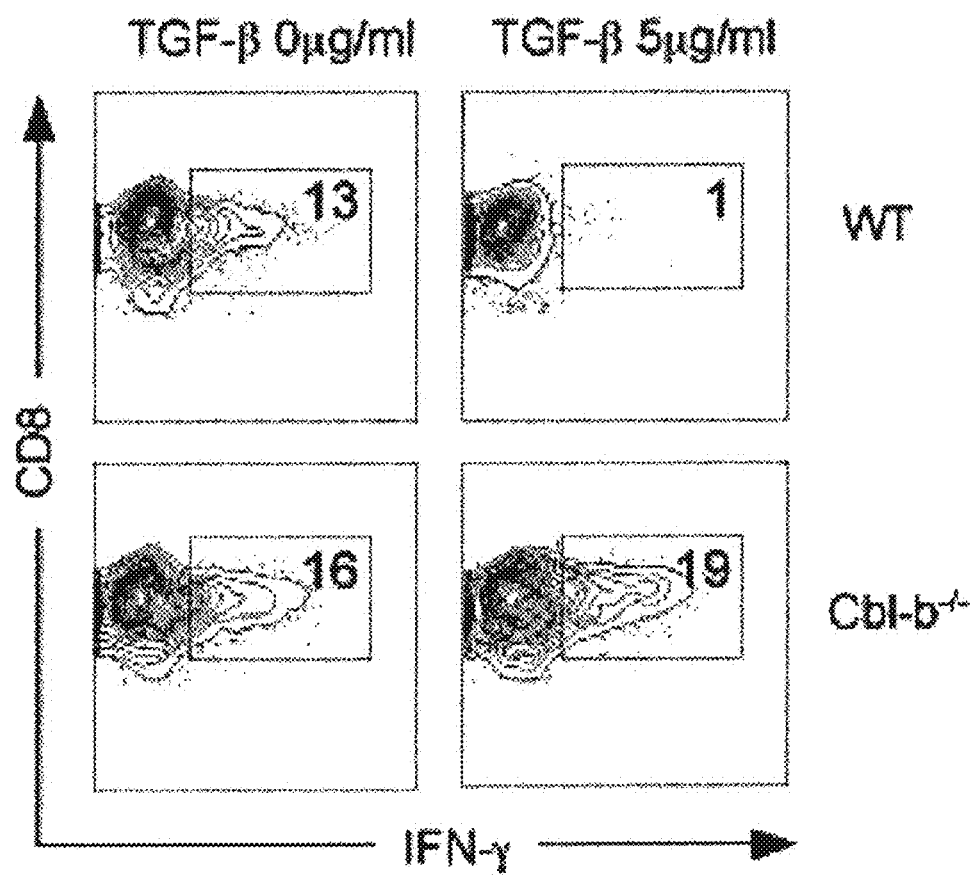
Figure 17:
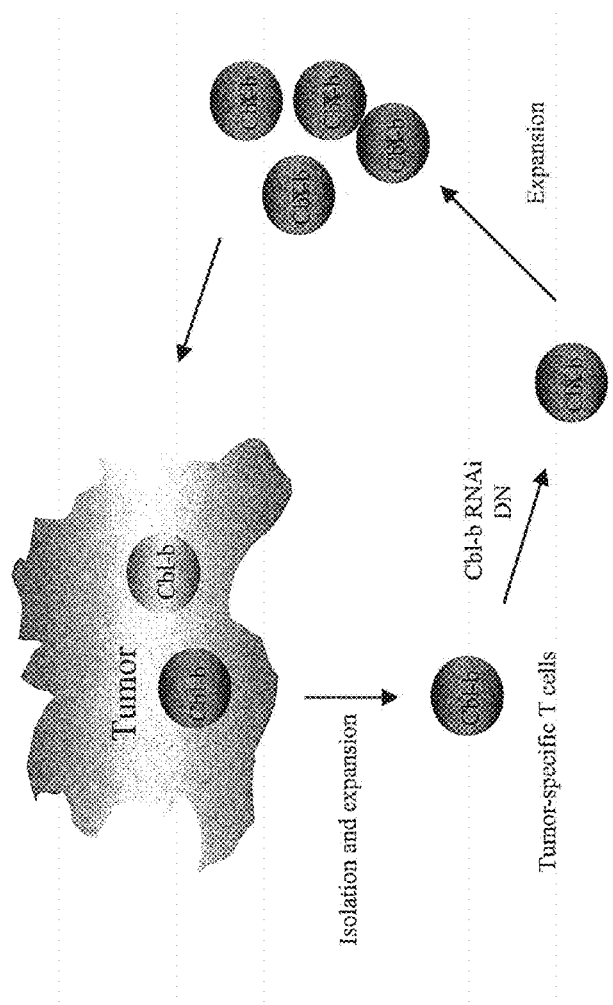
FIG. 17 shows one embodiment to generate Cbl-b−/− CD8+ T cells for tumor immunotherapy. Tumor tissues contain large amount tumor-infiltrating lymphocytes (TILs). These cells are enriched for tumor specific CD8+ cytotoxic T lymphocytes (CTLs). To isolate tumor specific CTLs, TILs can be activated in vitro by anti-CD3 and anti-CD28 stimulation in the presence of IL-2. To generate Cbl-b−/− CTLs, cell endogenous Cbl-b function can be ablated by expressing Cbl-b RNAi or a dominant negative form of Cbl-b using retroviral vector. Cbl-b ablated cells can be identified based on GFP expression, which is encoded by the same retroviral vector. Tumor specific Cbl-b-ablated CTLs can then be further expended in vitro using tumor-antigen or tumor cells as stimuli. Expanded cells can be used for the therapeutic adoptive transfer.

The impact of any one of these Ub-disabled Cbl-b mutants on the CD28 costimulatory signaling and T cell response to TGF-beta suppression can be determined as described herein. To exclude the possible interference of the endogenous wildtype Cbl-b, the Ub-disabled Cbl-b mutant can be introduced into Cbl-b$^{-/-}$ bone marrow (BM) stem cells, where infected stem cells can be transferred into Rag2$^{-/-}$ mice, and TCR-induced T-cell activation, IL-2 production, and TGF-beta suppression analyze in the presence or absence of CD28 costimulation, using T cells isolated from these chimeras. Ub-disabled Cbl-b can be introduced into c-Cbl Cbl-b dko BM stem cells by retroviral transduction using a hCD2 (or GFP)-based bi-cistronic retroviral vector. A wildtype Cbl-b transgene-expressing viral vector can be used as control. Certain embodiments use retrovirus-infected BM chimeras to demonstrate the function of c-Cbl in thymocyte development. The results shown in FIG. 14 demonstrate the feasibility of using such a system to express a transgene in hematopoietic stem cells.

After viral infection, retrovirus-transduced stem cells can be introduced into Rag2$^{-/-}$ recipient mice by i.v. injection to generate BM chimeras. Six to 8 weeks later, the development of the transgene-expressing T cells (hCD2$^+$ or GFP$^+$) in the recipient mice can be analyzed by FACS, using antibodies against CD4, CD8, and CD3. Since recipient mice are deficient in Rag2, T cells generated in these BM chimeras should be exclusively derived from the donor stem cells.

To investigate whether Ub-disabled Cbl-b affects CD28 costimulation and TGF-beta suppression, TCR-induced CD8$^+$ T cell proliferation in the presence or absence of different dose of TGF-beta, and cytokine (IL-2 and IFN-gamma) production can be determined by $^3$H-thymidine incorporation and ELISA, respectively. Ub-disabled (hCD2$^+$ or GFP$^+$) and Cbl-b$^{-/-}$ (hCD2$^-$ or GFP$^-$) CD8$^+$ can be purified from the BM chimeras by FACS or MACS sorting based on GFP or hCD2 expression.

An Ub-disabled Cbl-b protein can be overexpressed in wildtype CD8$^+$ T cells as a dominant negative suppressor for the endogenous Cbl-b function. This can be done by introducing and expressing Ub-disabled Cbl-b molecule into CD8$^+$ T cells from C57BL/6 mice by retroviral infection according to the method described herein. Virus infected cells can be purified by MACS. To determine whether the Ub-disabled Cbl-b-expressing CD8$^+$ T cells functionally mimic Cbl-b$^{-/-}$ CD8$^+$ T cells, the rates of proliferation and IL-2 and IFN-gamma production, as well as the resistance to TGF-beta suppression can be determined after TCR and CD28 stimulation. These embodiments can demonstrate whether a Ub-disabled Cbl-b can be used as a dominant negative form protein to ablate the function of T cell endogenous Cbl-b.

It is expected that expression of a wildtype Cbl-b in Cbl-b$^{-/-}$ T cells will fully restore T-cell dependence on CD28 costimulation for activation and TGF-beta sensitivity. If the ubiquitination function of Cbl-b is responsible for T-cell dependence on CD28 costimulation and TGF-beta sensitivity, a Ub-disabled Cbl-b-expressing CD8$^+$ T cells should proliferate and secrete IL-2 and IFN-gamma as efficiently as Cbl-b$^{-/-}$ T cells do. Additionally, anti-CD3-induced CD8$^+$ T cell proliferation will not be blocked by TGF-beta. Complete restoration of T-cell dependence on CD28 signal for the activation or TGF-beta sensitivity by Ub-disabled Cbl-b expression will suggest that other domains of Cbl-b and the corresponding associated proteins are responsible for these phenotypes of Cbl-b$^{-/-}$ T cells. Mutagenesis of other positions can identify these domains and molecules.

To determine the impact of the Ub-disabled Cbl-b on TCR signaling, the ubiquitination status of Cbl-b regulated signaling targets, for example but not limited to Vav and p85 PI-3 kinase, in the Ub-disabled Cbl-b mutant versus wildtype T cells can be, because signaling pathways involving Vav and p85 PI-3 kinase are altered in Cbl-b$^{-/-}$ T cells (55, 56, 73). If the activation, or phosphorylation of one of these signaling proteins in Ub-disabled Cbl-b-expressing T cells is similar to that in the wildtype cells, this can suggest that the ubiquitin ligase activity of Cbl-b is dispensable for the activation of this molecule. In contrast, if the ubiquitination function of Cbl-b is required for the activation of a particular signaling component, it can be expected that the phosphorylation status of this component in Ub-disabled Cbl-b-expressing cells will resemble that found in Cbl-b$^{-/-}$ T cells. In this case, it can be determined whether this particular signaling molecule is ubiquitinated in wildtype, and in Cbl-b$^{-/-}$ T cells. The kinetics of degradation of this molecule can be determined by Western blot hybridization.

One potential complication of this set of experiments is that the Ub-disabled Cbl-b partially complements the Cbl-b$^{-/-}$ phenotypes. This may suggest that either the expression level of the transgene is too low to fully compensate the Cbl-b function or that mechanisms other than ubiquitination are also involved in the regulation. To exclude the former possibility, costimulatory signaling can be analyzed in T cells from Ub-disabled Cbl-b knock-in mutant mice. Such a mouse model can be generated wherein in certain embodiments, the expression of Ub-disabled Cbl-b protein is driven by an endogenous Cbl-b promoter/enhancer at the endogenous locus. The expression of Ub-disabled Cbl-b protein is driven by an endogenous Cbl-b promoter/enhancer DNA sequence located at a position different from the endogenous locus. If T cells from such mice exhibit a partial restoration of the Cbl-b signaling, it can suggest that Cbl-b may use other mechanisms to regulate these signals. Further mutagenesis analysis of Cbl proteins can help to address this issue.

Inactivation of the ubiquitin ligase activity of Cbl-b or overexpression of a Ub-disabled Cbl-b in wildtype CD8$^+$ T cells enhances tumor rejection.

The role of the ubiquitination function of Cbl-b in tumor rejection can be studied using transgenic-T cells that express Ub-disabled Cbl-b protein variants, instead of or in addition to wildtype Cbl-b. T cells which express only Ub-disabled Cbl-b protein variants can mimic the situation where the ubiquitin ligase function of endogenous Cbl-b is blocked by an agent, for example but not limited to a small molecule drug. Ub-disabled Cbl-b protein variant can be expressed in wildtype CTLs by retroviral approach. In this case, the mutant Ub-disabled Cbl-b can be used as a dominant negative form to suppress the function of endogenous Cbl-b in T cells. These cells can potentially reject tumors as Cbl-b$^{-/-}$ CD8$^+$ T cells.

To determine whether Ub-disabled CD8+ T cells reject tumors, Cbl-b$^{-/-}$ OT1 and Pmel-1 TCR Tg mice can be generated. To obtain Ub-disabled Cbl-b-expressing naïve CD8$^+$ T cells, nucleic acid encoding Ub-disabled Cbl-b protein variants can be introduced into BM stem cells from these mice and generate BM chimera as described herein. To obtain Ub-disabled effector CD8$^+$ T cells, Ub-disabled naïve CD8+ T cells can be repetitively stimulated with CD3 and CD28, and expanded in the presence of IL-2. Ub-disabled Cbl-b-expressing naïve or effector T cells can be isolated from the above BM chimeras or from the in vitro cultured cells by MACS or FACS using hCD2 or GFP as cell surface markers. Once tumor-specific (OT1 or Pmel-1 TCR Tg) Ub-disabled Cbl-b-expressing naïve or effector T cells are generated, these cells can be transferred (1-10×10$^6$ cells/mouse) into corresponding tumor-bearing C57BL/6 mice by i.v. injection. Purified wildtype or Cbl-b$^{-/-}$ OT1 or Pmel-1 TCR Tg CD8+ T cells can be used as controls. Regression of tumors can be monitored as described herein. Whether the adoptively transferred Ub-disabled CD8+ T cells can generate long-term protection and immune memory against tumor can also be assessed. Whether Ub-disabled Cbl-b-expressing T cells can also eradicate tumors in the presence of TGF-beta or tumor barrier can be assessed by using TRAMP-2C and Ag104L$^d$ tumor model.

If the ubiquitin ligase function of Cbl-b is responsible for the inhibition of T-cell responsiveness against tumors in normal mice, it is expected that the Ub-disabled Cbl-b-expressing T cells can prevent the growth of the inoculated tumors similar to Cbl-b$^{-/-}$ T cells. This can suggest that in vivo inhibition of Cbl-b's ubiquitin ligase activity in T cells is sufficient to elicit anti-tumor immune responses against tumors. Identifying agents such chemical compounds that can antagonize the ubiquitin ligase activity of Cbl-b and examining whether treatment of mice with these agents enhances anti-tumor immune responses.

A systemic block of Cbl-b ubiquitin ligase function might have avert effect such as development of autoimmune diseases. However, the Cbl-b$^{-/-}$ mice do not exhibit any major abnormality in other tissues and nor do they develop spontaneous autoimmune diseases. Additionally, experiments show that Cbl-b$^{-/-}$ ATM$^{-/-}$ double mutant mice exhibit a markedly low incidence of spontaneous lymphomas as compared to the tumor-prone ATM$^{-/-}$ mice. These observations indicate that control of Cbl-b function by a chemical compound could be beneficial to both tumor immunotherapy and prevention.

If disruption of the ubiquitin ligase function of Cbl-b cannot confer T-cell responsiveness against tumors, or merely elicit a relatively weaker anti-tumor response compared to Cbl-b$^{-/-}$ T cells, it can suggest that other domain(s) of Cbl-b and the corresponding associated molecules are important in T cell immunity against tumor. Further mutagenesis studies as described herein may identify the domains that are linked to CD28 costimulatory signal. The ability of these mutants to confer T cell immunity to tumors will be examined using the above experimental setting.

It is possible that expression level of the Ub-disabled Cbl-b in T cells using the above approach is not comparable to that of the endogenous Cbl-b. The above described analyses can also be done using Ub-disabled Cbl-b knock-in mice.

In certain embodiments, the invention provides methods for determining the mechanisms by which Cbl-b$^{-/-}$ mice mount an efficient anti-tumor immune response and methods for modulating Cbl-b signaling pathway in T cells for tumor immunotherapy. In certain aspects, the invention provides that Cbl-b$^{-/-}$ mice are resistant to E.G7 tumor inoculation. Resistance to tumor inoculation is dependent on T cells. The invention also provides that Cbl-b$^{-/-}$ T cells respond to antigen stimulation independent of CD28 costimulation. In other aspects, the invention provides that Cbl-b can control CD28 costimulatory signal through its ubiquitin ligase function.

The invention further provides that Cbl-b$^{-/-}$ CTLs are necessary and sufficient to mount anti-tumor immune responses in animal models. In certain aspect, the invention provides that ablation of Cbl-b in tumor-infiltrating T cells, which are enriched for naturally generated tumor-specific CTLs, generates T cells can be used as the "super killers" to eradicate the established tumors. In other aspects, the invention provides that inactivation of Cbl-b's ubiquitin ligase activity can be sufficient to render T-cell responsiveness against tumors.

In certain embodiments, the invention provides methods that determine the mechanisms underlying the expansion of Cbl deficient T1 B cells in the context of B-cell tolerance. Analysis can include generation and maturation of T1 B cells in vivo. In other embodiments, the susceptibility of BCR-induced death of Cbl-dKO T1 B cells can be examined. Analysis can also include assessing the potential effect of T cells on the maturation and survival of Cbl-dKO T1 B cells.

In other embodiments, the invention provides methods to determine whether the expansion of Cbl-dKO T1 B cells causes the breakdown of B-cell tolerance. Because T1 B cells represent a developmental stage of B cells when they are susceptible to autoantigen-induced anergy or death, the accelerated maturation of Cbl-dKO B cells could shorten the developmental window during which B-cell tolerance can be induced by autoantigen.

REFERENCES

1. Houghton A N, Gold J S, Blachere N E. 2001. Immunity against cancer: lessons learned from melanoma. *Curr Opin Immunol* 13: 134-40
2. Rosenberg S A. 2001. Progress in human tumour immunology and immunotherapy. *Nature* 411: 380-4
3. Boon T, Cerottini J C, Van den Eynde B, van der Bruggen P, Van Pel A. 1994. Tumor antigens recognized by T lymphocytes. *Annu Rev Immunol* 12: 337-65
4. Pardoll D M. 1998. Cancer vaccines. *Nat Med* 4: 525-31
5. Rosenberg S A, Yang J C, Restifo N P. 2004. Cancer immunotherapy: moving beyond current vaccines. *Nat Med* 10: 909-15
6. Schuler G, Schuler-Thurner B, Steinman R M. 2003. The use of dendritic cells in cancer immunotherapy. *Curr Opin Immunol* 15: 138-47
7. Boon T, van der Bruggen P. 1996. Human tumor antigens recognized by T lymphocytes. *J Exp Med* 183: 725-9
8. Rosenberg S A. 1999. A new era of cancer immunotherapy: converting theory to performance. *CA Cancer J Clin* 49: 70-3, 65
9. Restifo N P, Esquivel F, Asher A L, Stotter H, Barth R J, Bennink J R, Mule J J, Yewdell J W, Rosenberg S A. 1991. Defective presentation of endogenous antigens by a murine sarcoma. Implications for the failure of an anti-tumor immune response. *J Immunol* 147: 1453-9
10. Berzofsky J A, Ahlers J D, Belyakov I M. 2001. Strategies for designing and optimizing new generation vaccines. *Nat Rev Immunol* 1: 209-19
11. Groh V, Wu J, Yee C, Spies T. 2002. Tumour-derived soluble MIC ligands impair expression of NKG2D and T-cell activation. *Nature* 419: 734-8
12. Chambers C A, Kuhns M S, Egen J G, Allison J P. 2001. CTLA-4-mediated inhibition in regulation of T cell responses: mechanisms and manipulation in tumor immunotherapy. *Annu Rev Immunol* 19: 565-94
13. Terabe M, Matsui S, Noben-Trauth N, Chen H, Watson C, Donaldson D D, Carbone D P, Paul W E, Berzofsky J A. 2000. NKT cell-mediated repression of tumor immunosurveillance by IL-13 and the IL-4R-STAT6 pathway. *Nat Immunol* 1: 515-20
14. Perdrizet G A, Ross S R, Stauss H J, Singh S, Koeppen H, Schreiber H. 1990. Animals bearing malignant grafts reject normal grafts that express through gene transfer the same antigen. *J Exp Med* 171: 1205-20
15. Ochsenbein A F, Klenerman P, Karrer U, Ludewig B, Pericin M, Hengartner H, Zinkernagel R M. 1999. Immune surveillance against a solid tumor fails because of immunological ignorance. *Proc Natl Acad Sci USA* 96: 2233-8
16. Singh S, Ross S R, Acena M, Rowley D A, Schreiber H. 1992. Stroma is critical for preventing or permitting immunological destruction of antigenic cancer cells. *J Exp Med* 175: 139-46
17. Ramarathinam L, Castle M, Wu Y, Liu Y. 1994. T cell costimulation by B7/BB1 induces CD8 T cell-dependent tumor rejection: an important role of B7/BB1 in the induction, recruitment, and effector function of antitumor T cells. *J Exp Med* 179: 1205-14
18. Mueller D L, Jenkins M K, Schwartz R H. 1989. Clonal expansion versus functional clonal inactivation: a costimulatory signalling pathway determines the outcome of T cell antigen receptor occupancy. *Annu Rev Immunol* 7: 445-80
19. Janeway C. 1989. Immunogenicity signals 1, 2, 3 . . . and 0. *Immunol Today* 10: 283-6
20. Lafferty K J, Prowse S J, Simeonovic C J, Warren H S. 1983. Immunobiology of tissue transplantation: a return to the passenger leukocyte concept. *Annu Rev Immunol* 1: 143-73
21. Weaver C T, Unanue E R. 1990. The costimulatory function of antigen-presenting cells. *Immunol Today* 11: 49-55
22. Allison J P, Hurwitz A A, Leach D R. 1995. Manipulation of costimulatory signals to enhance antitumor T-cell responses. *Curr Opin Immunol* 7: 682-6
23. Linsley P S, Brady W, Grosmaire L, Aruffo A, Damle N K, Ledbetter J A. 1991. Binding of the B cell activation antigen B7 to CD28 costimulates T cell proliferation and interleukin 2 mRNA accumulation. *J Exp Med* 173: 721-30
24. Ledbetter J A, Imboden J B, Schieven G L, Grosmaire L S, Rabinovitch P S, Lindsten T, Thompson C B, June C H. 1990. CD28 ligation in T-cell activation: evidence for two signal transduction pathways. *Blood* 75: 1531-9
25. Schwartz R H. 1992. Costimulation of T lymphocytes: the role of CD28, CTLA-4, and B7/BB1 in interleukin-2 production and immunotherapy. *Cell* 71: 1065-8
26. Chen L, Ashe S, Brady W A, Hellstrom I, Hellstrom K E, Ledbetter J A, McGowan P, Linsley P S. 1992. Costimulation of antitumor immunity by the B7 counter-receptor for the T lymphocyte molecules CD28 and CTLA-4. *Cell* 71: 1093-102
27. Greenberg P D. 1991. Adoptive T cell therapy of tumors: mechanisms operative in the recognition and elimination of tumor cells. *Adv Immunol* 49: 281-355
28. Melief C J. 1992. Tumor eradication by adoptive transfer of cytotoxic T lymphocytes. *Adv Cancer Res* 58: 143-75
29. Ceredig R, Allan J E, Tabi Z, Lynch F, Doherty P C. 1987. Phenotypic analysis of the inflammatory exudate in murine lymphocytic choriomeningitis. *J Exp Med* 165: 1539-51
30. Yu P, Lee Y, Liu W, Chin R K, Wang J, Wang Y, Schietinger A, Philip M, Schreiber H, Fu Y X. 2004. Priming of naive T cells inside tumors leads to eradication of established tumors. *Nat Immunol* 5: 141-9
31. Hanson H L, Donermeyer D L, Ikeda H, White J M, Shankaran V, Old L J, Shiku H, Schreiber R D, Allen P M. 2000. Eradication of established tumors by CD8+ T cell adoptive immunotherapy. *Immunity* 13: 265-76
32. Wick M, Dubey P, Koeppen H, Siegel C T, Fields P E, Chen L, Bluestone J A, Schreiber H. 1997. Antigenic cancer cells grow progressively in immune hosts without evidence for T cell exhaustion or systemic anergy. *J Exp Med* 186: 229-38
33. Sarma S, Guo Y, Guilloux Y, Lee C, Bai X F, Liu Y. 1999. Cytotoxic T lymphocytes to an unmutated tumor rejection antigen P1A: normal development but restrained effector function in vivo. *J Exp Med* 189: 811-20
34. Overwijk W W, Theoret M R, Finkelstein S E, Surman D R, de Jong L A, Vyth-Dreese F A, Dellemijn T A, Antony P A, Spiess P J, Palmer D C, Heimann D M, Klebanoff C A, Yu Z, Hwang L N, Feigenbaum L, Kruisbeek A M, Rosenberg S A, Restifo N P. 2003. Tumor regression and autoimmunity after reversal of a functionally tolerant state of self-reactive CD8+ T cells. *J Exp Med* 198: 569-80
35. Townsend S E, Allison J P. 1993. Tumor rejection after direct costimulation of CD8+ T cells by B7-transfected melanoma cells. *Science* 259: 368-70
36. Chen L, McGowan P, Ashe S, Johnston J, Li Y, Hellstrom I, Hellstrom K E. 1994. Tumor immunogenicity determines the effect of B7 costimulation on T cell-mediated tumor immunity. *J Exp Med* 179: 523-32
37. Wallin J J, Liang L, Bakardjiev A, Sha W C. 2001. Enhancement of CD8+ T cell responses by ICOS/B7h costimulation. *J Immunol* 167: 132-9
38. Liu X, Bai X F, Wen J, Gao J X, Liu J, Lu P, Wang Y, Zheng P, Liu Y. 2001. B7H costimulates clonal expansion of, and cognate destruction of tumor cells by, CD8(+) T lymphocytes in vivo. *J Exp Med* 194: 1339-48
39. Steinman R M. 2001. Dendritic cells and the control of immunity: enhancing the efficiency of antigen presentation. *Mt Sinai J Med* 68: 106-66
40. Morisaki T, Matsumoto K, Onishi H, Kuroki H, Baba E, Tasaki A, Kubo M, Nakamura M, Inaba S, Yamaguchi K, Tanaka M, Katano M. 2003. Dendritic cell-based combined immunotherapy with autologous tumor-pulsed dendritic cell vaccine and activated T cells for cancer patients: rationale, current progress, and perspectives. *Hum Cell* 16: 175-82
41. Kedl R M, Rees W A, Hildeman D A, Schaefer B, Mitchell T, Kappler J, Marrack P. 2000. T cells compete for access to antigen-bearing antigen-presenting cells. *J Exp Med* 192: 1105-13
42. Helmich B K, Dutton R W. 2001. The role of adoptively transferred CD8 T cells and host cells in the control of the growth of the E. G7 thymoma: factors that determine the relative effectiveness and homing properties of Tc1 and Tc2 effectors. *J Immunol* 166: 6500-8
43. Kelly J M, Steffy S J, Cose S, Turner S J, Fecondo J, Rodda S, Fink P J, Carbone F R. 1993. Identification of conserved T cell receptor CDR3 residues contacting known exposed peptide side chains from a major histocompatibility complex class I-bound determinant. *Eur J Immunol* 23: 3318-26
44. Hogquist K A, Jameson S C, Heath W R, Howard J L, Bevan M J, Carbone F R. 1994. T cell receptor antagonist peptides induce positive selection. *Cell* 76: 17-27
45. Finkelstein S E, Heimann D M, Klebanoff C A, Antony P A, Gattinoni L, Hinrichs C S, Hwang L N, Palmer D C, Spiess P J, Surman D R, Wrzesiniski C, Yu Z, Rosenberg S A, Restifo N P. 2004. Bedside to bench and back again: how animal models are guiding the development of new immunotherapies for cancer. *J Leukoc Biol* 76: 333-7
46. Rao N, Dodge I, Band H. 2002. The Cbl family of ubiquitin ligases: critical negative regulators of tyrosine kinase signaling in the immune system. *J Leukoc Biol* 71: 753-63
47. Liu Y C, Gu H. 2002. Cbl and Cbl-b in T-cell regulation. *Trends Immunol* 23: 140-3
48. Thien C B, Langdon W Y. 2001. Cbl: many adaptations to regulate protein tyrosine kinases. *Nat Rev Mol Cell Biol* 2: 294-307
49. Regnier D C, Kozak C A, Kingsley D M, Jenkins N A, Copeland N G, Langdon W Y, Morse H C, 3rd. 1989. Identification of two murine loci homologous to the v-cbl oncogene. *J Virol* 63: 3678-82
50. Keane M M, Rivero-Lezcano O M, Mitchell J A, Robbins K C, Lipkowitz S. 1995. Cloning and characterization of cbl-b: a SH3 binding protein with homology to the c-cbl proto-oncogene. *Oncogene* 10: 2367-77
51. Keane M M, Ettenberg S A, Nau M M, Banerjee P, Cuello M, Penninger J, Lipkowitz S. 1999. cbl-3: a new mammalian cbl family protein. *Oncogene* 18: 3365-75
52. Lupher M L, Jr., Andoniou C E, Bonita D, Miyake S, Band H. 1998. The c-Cbl oncoprotein. *Int J Biochem Cell Biol* 30: 439-44
53. Joazeiro C A, Wing S S, Huang H, Leverson J D, Hunter T, Liu Y C. 1999. The tyrosine kinase negative regulator c-Cbl as a RING-type, E2-dependent ubiquitin-protein ligase. *Science* 286: 309-12
54. Murphy M A, Schnall R G, Venter D J, Barnett L, Bertoncello I, Thien C B, Langdon W Y, Bowtell D D. 1998. Tissue hyperplasia and enhanced T-cell signalling via ZAP-70 in c-Cbl-deficient mice. *Mol Cell Biol* 18: 4872-82
55. Bachmaier K, Krawczyk C, Kozieradzki I, Kong Y Y, Sasaki T, Oliveira-dos-Santos A, Mariathasan S, Bouchard D, Wakeham A, Itie A, Le J, Ohashi P S, Sarosi I, Nishina H, Lipkowitz S, Penninger J M. 2000. Negative regulation of lymphocyte activation and autoimmunity by the molecular adaptor Cbl-b. *Nature* 403: 211-6
56. Chiang Y J, Kole H K, Brown K, Naramura M, Fukuhara S, Hu R J, Jang I K, Gutkind J S, Shevach E, Gu H. 2000. Cbl-b regulates the CD28 dependence of T-cell activation. *Nature* 403: 216-20
57. Naramura M, Kole H K, Hu R J, Gu H. 1998. Altered thymic positive selection and intracellular signals in Cbl-deficient mice. *Proc Natl Acad Sci USA* 95: 15547-52
58. Naramura M, Jang I K, Kole H, Huang F, Haines D, Gu H. 2002. c-Cbl and Cbl-b regulate T cell responsiveness by promoting ligand-induced TCR down-modulation. *Nat Immunol* 3: 1192-9
59. Roes J, Rajewsky K. 1991. *Cell* autonomous expression of IgD is not essential for the maturation of conventional B cells. *Int Immunol* 3: 1367-71
60. Umlauf S W, Beverly B, Lantz O, Schwartz R H. 1995. Regulation of interleukin 2 gene expression by CD28 costimulation in mouse T-cell clones: both nuclear and cytoplasmic RNAs are regulated with complex kinetics. *Mol Cell Biol* 15: 3197-205
61. Naramura M, Hu R J, Gu H. 1998. Mice with a fluorescent marker for interleukin 2 gene activation. *Immunity* 9: 209-16
62. Dudley M E, Wunderlich J R, Robbins P F, Yang J C, Hwu P, Schwartzentruber D J, Topalian S L, Sherry R, Restifo N P, Hubicki A M, Robinson M R, Raffeld M, Duray P, Seipp C A, Rogers-Freezer L, Morton K E, Mavroukakis S A, White D E, Rosenberg S A. 2002. Cancer regression and autoimmunity in patients after clonal repopulation with antitumor lymphocytes. *Science* 298: 850-4
63. Dudley M E, Rosenberg S A. 2003. Adoptive-cell-transfer therapy for the treatment of patients with cancer. *Nat Rev Cancer* 3: 666-75
64. Speiser D E, Miranda R, Zakarian A, Bachmann M F, McKall-Faienza K, Odermatt B, Hanahan D, Zinkernagel R M, Ohashi P S. 1997. Self antigens expressed by solid tumors Do not efficiently stimulate naive or activated T cells: implications for immunotherapy. *J Exp Med* 186: 645-53
65. Nestle F O, Alijagic S, Gilliet M, Sun Y, Grabbe S, Dummer R, Burg G, Schadendorf D. 1998. Vaccination of melanoma patients with peptide- or tumor lysate-pulsed dendritic cells. *Nat Med* 4: 328-32
66. Lee P P, Yee C, Savage P A, Fong L, Brockstedt D, Weber J S, Johnson D, Swetter S, Thompson J, Greenberg P D, Roederer M, Davis M M. 1999. Characterization of circulating T cells specific for tumor-associated antigens in melanoma patients. *Nat Med* 5: 677-85
67. Yu P, Spiotto M T, Lee Y, Schreiber H, Fu Y X. 2003. Complementary role of CD4+ T cells and secondary lymphoid tissues for cross-presentation of tumor antigen to CD8+ T cells. *J Exp Med* 197: 985-95
68. Rubinson D A, Dillon C P, Kwiatkowski A V, Sievers C, Yang L, Kopinj a J, Rooney D L, Ihrig M M, McManus M T, Gertler F B, Scott M L, Van Parijs L. 2003. A lentivirus-based system to functionally silence genes in primary mammalian cells, stem cells and transgenic mice by RNA interference. *Nat Genet* 33: 401-6
69. Brummelkamp T R, Bernards R, Agami R. 2002. A system for stable expression of short interfering RNAs in mammalian cells. *Science* 296: 550-3
70. Zou Y R, Sunshine M J, Taniuchi I, Hatam F, Killeen N, Littman D R. 2001. Epigenetic silencing of CD4 in T cells committed to the cytotoxic lineage. *Nat Genet* 29: 332-6
71. Ledbetter J A, Rouse R V, Micklem H S, Herzenberg L A. 1980. T cell subsets defined by expression of Lyt-1,2,3 and Thy-1 antigens. Two-parameter immunofluorescence and cytotoxicity analysis with monoclonal antibodies modifies current views. *J Exp Med* 152: 280-95
72. Singer O, Yanai A, Verma I M. 2004. Silence of the genes. *Proc Natl Acad Sci USA* 101: 5313-4
73. Fang D, Liu Y C. 2001. Proteolysis-independent regulation of PI3K by Cbl-b-mediated ubiquitination in T cells. *Nat Immunol* 2: 870-5
74. Miura-Shimura Y, Duan L, Rao N L, Reddi A L, Shimura H, Rottapel R, Druker B J, Tsygankov A, Band V, Band H. 2003. Cbl-mediated ubiquitinylation and negative regulation of Vay. *J Biol Chem* 278: 38495-504
75. Zheng N, Wang P, Jeffrey P D, Pavletich N P. 2000. Structure of a c-Cbl-UbcH7 complex: RING domain function in ubiquitin-protein ligases. *Cell* 102: 533-9
76. Freemont P S. 2000. RING for destruction? *Curr Biol* 10: R84-7

77. Levkowitz G, Waterman H, Ettenberg S A, Katz M, Tsygankov A Y, Alroy I, Lavi S, Iwai K, Reiss Y, Ciechanover A, Lipkowitz S, Yarden Y. 1999. Ubiquitin ligase activity and tyrosine phosphorylation underlie suppression of growth factor signaling by c-Cbl/Sli-1. *Mol Cell* 4: 1029-40

78. Tsygankov A Y, Teckchandani A M, Feshchenko E A, Swaminathan G. 2001. Beyond the RING: CBL proteins as multivalent adapters. *Oncogene* 20: 6382-402

79. Rosenberg, S. A. 1999. A new era of cancer immunotherapy: converting theory to performance. *CA Cancer J Clin* 49:70-73, 65.

80. Somasundaram, R., L. Jacob, R. Swoboda, L. Caputo, H. Song, S. Basak, D. Monos, D. Peritt, F. Marincola, D. Cai, B. Birebent, E. Bloome, J. Kim, K. Berencsi, M. Mastrangelo, and D. Herlyn. 2002. Inhibition of cytolytic T lymphocyte proliferation by autologous CD4+/CD25+ regulatory T cells in a colorectal carcinoma patient is mediated by transforming growth factor-beta. *Cancer Res* 62:5267-5272.

81. Yu, X., R. Abe, and R. J. Hodes. 1998. The role of B7-CD28 co-stimulation in tumor rejection. *Int Immunol* 10:791-797.

82. Jeon, M. S., A. Atfield, K. Venuprasad, C. Krawczyk, R. Sarao, C. Elly, C. Yang, S. Arya, K. Bachmaier, L. Su, D. Bouchard, R. Jones, M. Gronski, P. Ohashi, T. Wada, D. Bloom, C. G. Fathman, Y. C. Liu, and J. M. Penninger. 2004. Essential role of the E3 ubiquitin ligase Cbl-b in T cell anergy induction. *Immunity* 21:167-177.

83. Kronenberg, M., and A. Rudensky. 2005. Regulation of immunity by self-reactive T cells. *Nature* 435:598-604.

reduced Cbl-b activity compared to non-modified CD8+ T cells is included in a pharmaceutical composition.

2. The cells of claim 1, wherein the CD8+ T-cells are provided from peripheral blood, lymph organs, or tumor infiltrates.

3. The cells of claim 1, wherein the CD8+ T-cells are isolated from a subject.

4. The cells of claim 3, wherein the CD8+ T-cells are isolated from tumor infiltrates from the subject.

5. The cells of claim 4, wherein the CD8+ T-cells are polyclonal.

6. The cells of claim 1, 2, or 3, wherein the CD8+ T cells with reduced Cbl-b activity have been stimulated to proliferate.

7. The cells of claim 1, 2, or 3, wherein the CD8+ T cells with reduced Cbl-b activity have been stimulated to proliferate with tumor cells isolated from a subject, so as to increase the number of tumor specific CD8+ T cells with reduced Cbl-b activity.

8. The cells of claim 7, wherein the tumor specific CD8+ T cells with reduced Cbl-b activity have been contacted with an anti-CD3 antibody or incubated with IL-2 or a combination thereof in order to further increase the number of the tumor specific CD8+ T cells with reduced Cbl-b activity.

What is claimed is:

1. An isolated, substantially purified, population of cells comprising CD8+ T cells with reduced Cbl-b activity compared to non-modified CD8+ T cells, wherein the Cbl-b activity is reduced by one or more of: (i) contacting the CD8+ T cells with a chemical agent which inhibits Cbl-b expression or activity, (ii) introducing an siRNA, which targets Cbl-b in the CD8+ T cells, or (iii) knocking out the gene encoding Cbl-b, and wherein the isolated, substantially purified, population of cells comprising CD8+ T cells with 9. The cells of claim 1, 2, or 3, wherein the siRNA is SEQ ID NO: 1 (5'-CAGGAGTATGAGACAGAAG 3').

10. The cells of claim 1, wherein the pharmaceutical composition is used to treat cancer in a subject, or for immune rejection of a tumor in a subject.

11. The cells of claim 10, wherein the subject suffers from melanoma, lymphoma, or any solid tumors expressing MHC-I with an antigen that can be recognized by cytotoxic T lymphocytes.

* * * * *